US006894773B2

(12) United States Patent
Morioka et al.

(10) Patent No.: US 6,894,773 B2
(45) Date of Patent: May 17, 2005

(54) METHOD AND APPARATUS FOR ANALYZING THE STATE OF GENERATION OF FOREIGN PARTICLES IN SEMICONDUCTOR FABRICATION PROCESS

(75) Inventors: Hiroshi Morioka, Ebina (JP); Minori Noguchi, Yokohama (JP); Yoshimasa Ohshima, Yokohama (JP); Yukio Kembo, Yokohama (JP); Hidetoshi Nishiyama, Fujisawa (JP); Kazuhiko Matsuoka, Gunma-ken (JP); Yoshiharu Shigyo, Takasaki (JP)

(73) Assignee: Renesas Technology Corp., Tokyo (JP)

( * ) Notice: Subject to any disclaimer, the term of this patent is extended or adjusted under 35 U.S.C. 154(b) by 0 days.

(21) Appl. No.: 09/805,188

(22) Filed: Mar. 14, 2001

(65) Prior Publication Data

US 2001/0021015 A1 Sep. 13, 2001

Related U.S. Application Data

(63) Continuation of application No. 08/535,577, filed on Sep. 28, 1995, which is a continuation of application No. 08/046,720, filed on Apr. 16, 1993, now Pat. No. 5,463,459, which is a continuation-in-part of application No. 07/778,363, filed on Oct. 17, 1991, now Pat. No. 5,274,434, and a continuation-in-part of application No. 07/679,317, filed on Apr. 2, 1991, now Pat. No. 5,233,191.

(30) Foreign Application Priority Data

Apr. 17, 1992 (JP) .......................................... P04-98095

(51) Int. Cl.[7] .............................................. G01N 21/00
(52) U.S. Cl. .................................................... 356/237.5
(58) Field of Search ................................ 356/237, 239, 356/394, 336, 237.1–237.5, 338, 445, 337, 345; 250/559.4, 559.41, 559.45; 438/14, 16, 790, 905, 935, 706

(56) References Cited

U.S. PATENT DOCUMENTS

| | | | |
|---|---|---|---|
| 3,658,420 A | 4/1972 | Axelrod | |
| 3,771,880 A | 11/1973 | Bennett | |
| 3,930,155 A | 12/1975 | Kanomata et al. | |
| 4,332,833 A | 6/1982 | Aspnes et al. | |
| 4,376,583 A | 3/1983 | Alford et al. | |
| 4,378,159 A | 3/1983 | Galbraith | |
| 4,441,124 A | 4/1984 | Heebner et al. | |
| 4,441,268 A | 4/1984 | Sherman et al. | |

(Continued)

FOREIGN PATENT DOCUMENTS

| | | |
|---|---|---|
| JP | 59-65428 | 4/1984 |
| JP | 64-069023 | 3/1989 |
| SU | 1257725 | 9/1986 |

OTHER PUBLICATIONS

"Simultaneous Observations of Partially Oxidized . . . ", Komiya et al, J. Vac. Sci. Technology, vol. 12, No. 1, Jan./Feb. 1975.
"Scanning Laser Senses Wafer Defects", Electronics, Mar. 16, 1978, vol. 51, No. 6, pp. 48 and 50, Copy 356/237.

*Primary Examiner*—Tu T. Nguyen
(74) *Attorney, Agent, or Firm*—Antonelli, Terry, Stout & Kraus, LLP

(57) ABSTRACT

A processing method for semiconductor devices in a semiconductor fabrication line includes processing a substrate in a first processing apparatus, transferring the substrate processed in the first processing apparatus to a detecting apparatus without removal of the substrate from the semiconductor fabrication line while continuing fabrication of the semiconductor devices, detecting foreign particle defects on the substrate transferred to the detecting apparatus, and determining a foreign particle generation condition of the processing apparatus based on a data from the detecting.

27 Claims, 34 Drawing Sheets

U.S. PATENT DOCUMENTS

| | | | |
|---|---|---|---|
| 4,448,532 A | | 5/1984 | Joseph et al. |
| 4,571,685 A | * | 2/1986 | Kamoshida ................. 700/108 |
| 4,575,922 A | | 3/1986 | Nemiroff |
| 4,614,427 A | * | 9/1986 | Koizumi et al. ......... 356/237.1 |
| 4,744,666 A | * | 5/1988 | Oshida et al. .............. 356/401 |
| 4,806,774 A | | 2/1989 | Lin et al. |
| 4,856,904 A | | 8/1989 | Akagawa |
| 4,939,363 A | | 7/1990 | Bando et al. |
| 4,963,500 A | | 10/1990 | Cogan et al. |
| 5,004,307 A | | 4/1991 | Kino et al. |
| 5,028,778 A | | 7/1991 | Ninomiya et al. |
| 5,055,679 A | | 10/1991 | Ninomiya et al. |
| 5,172,000 A | * | 12/1992 | Scheff et al. ............... 250/550 |
| 5,274,434 A | | 12/1993 | Morioka et al. |
| 5,276,498 A | | 1/1994 | Galbraith et al. |
| 5,861,952 A | * | 1/1999 | Tsuji et al. ................. 356/349 |

* cited by examiner

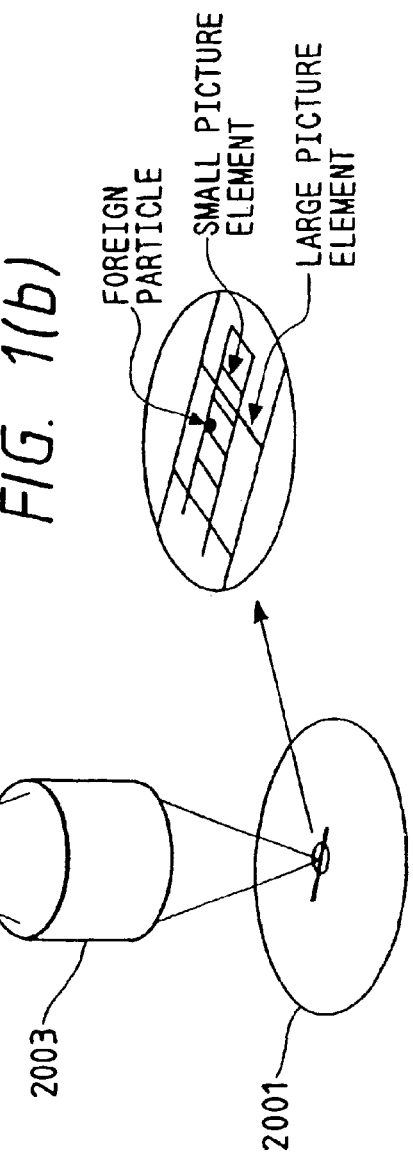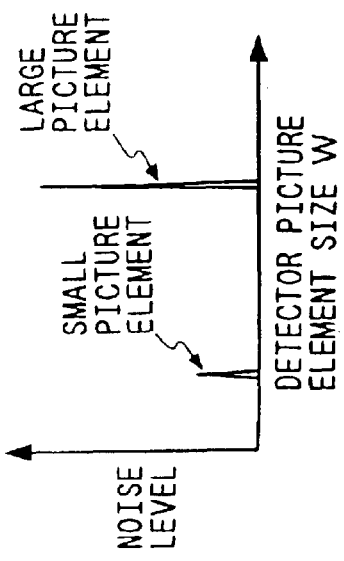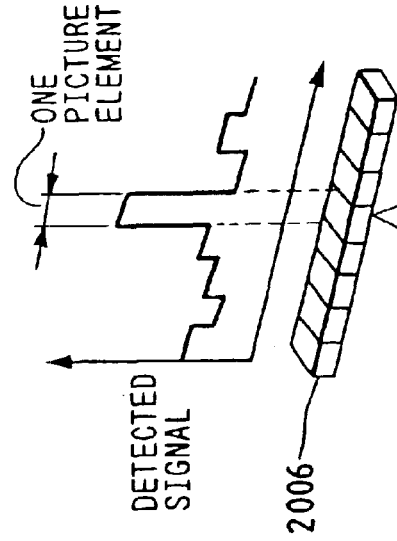

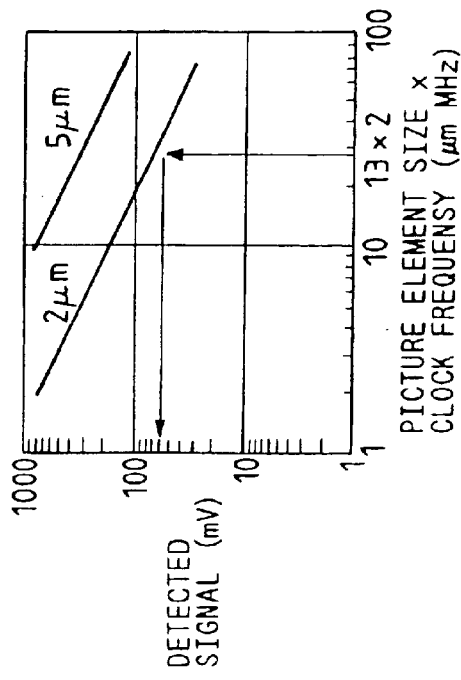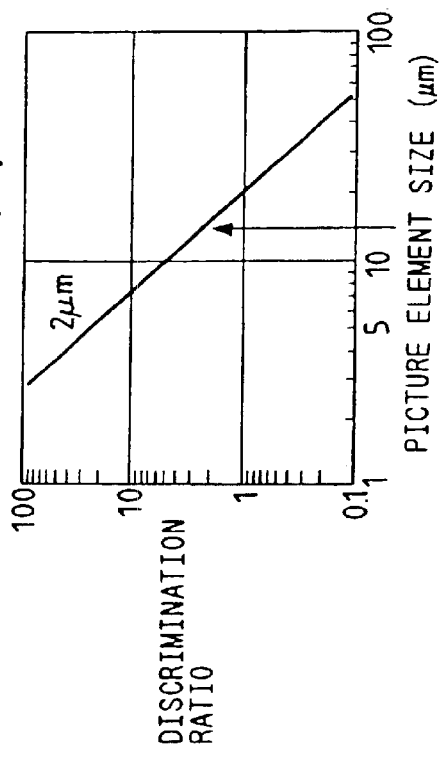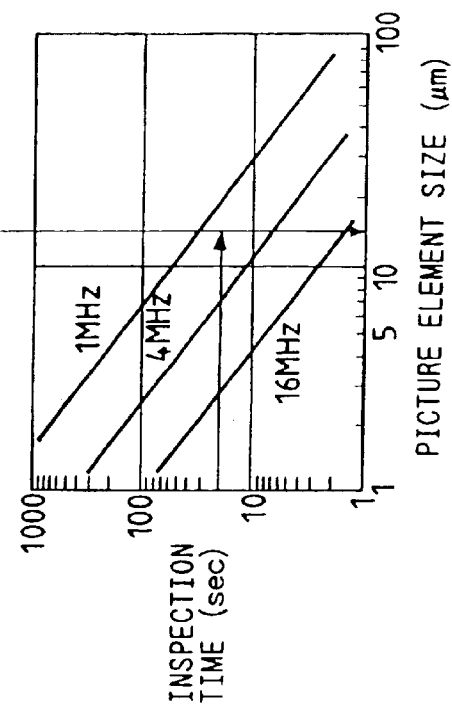

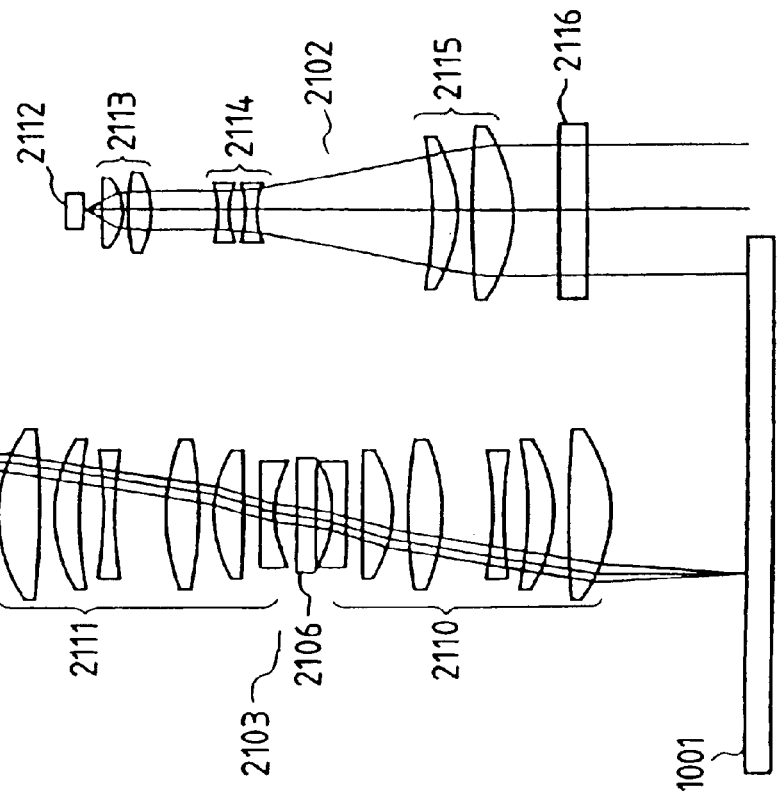
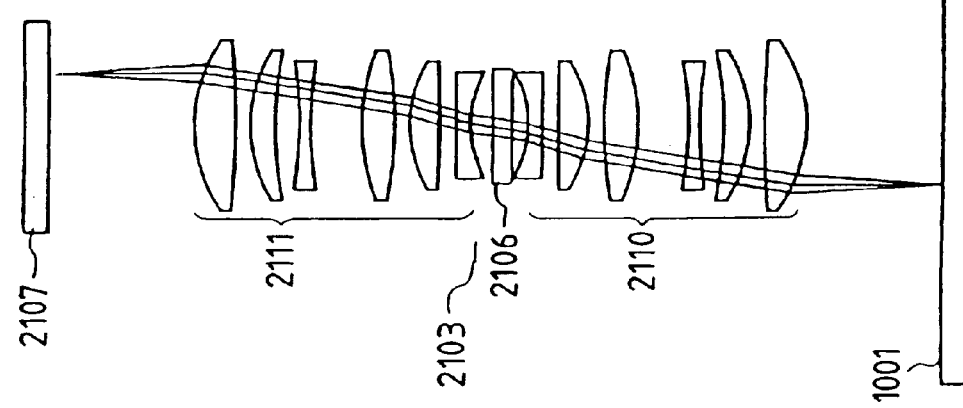
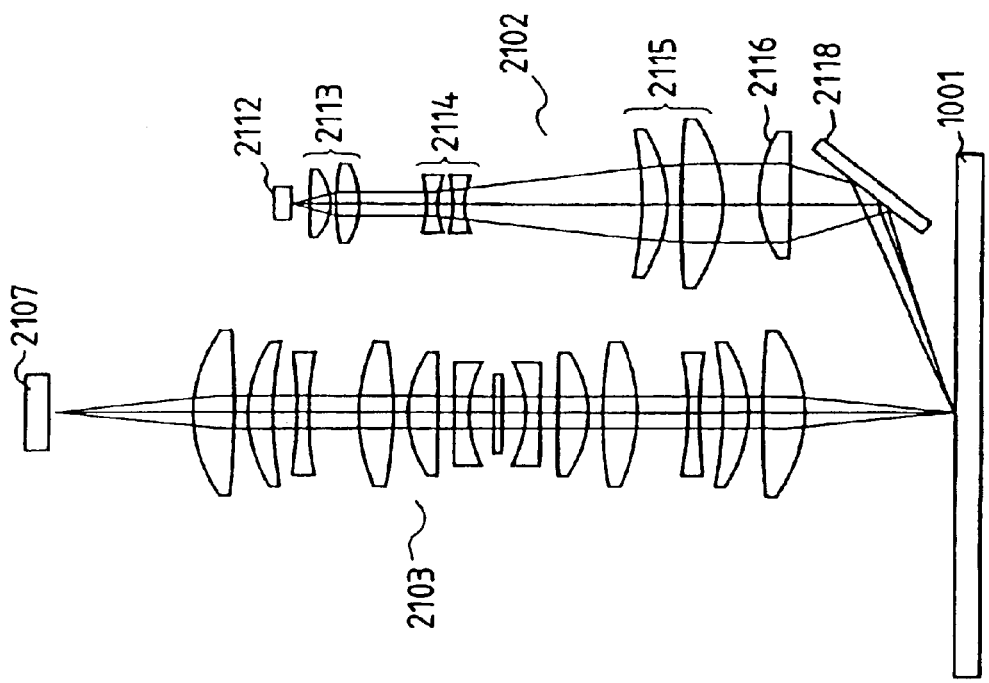

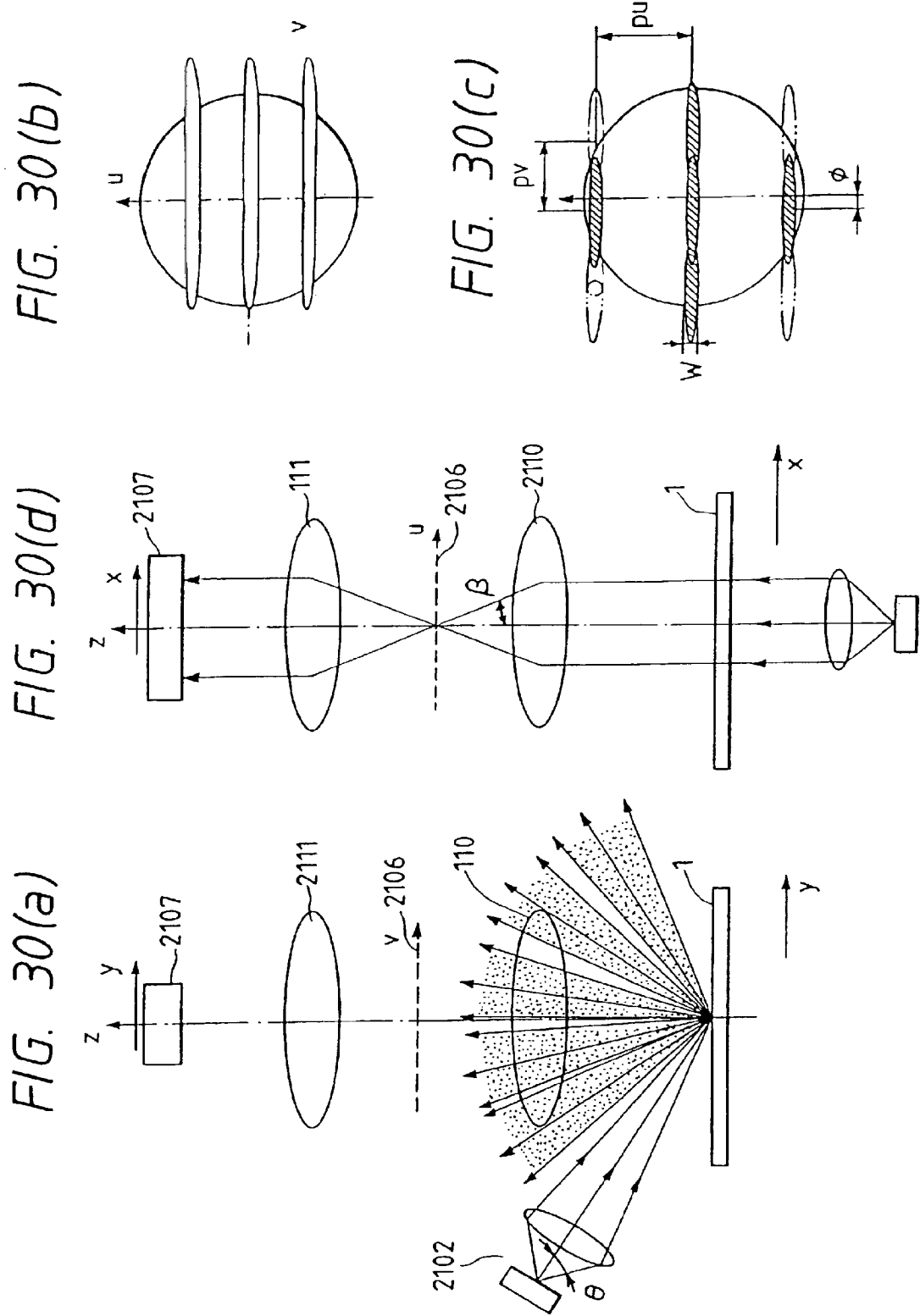

FIG. 31(a)

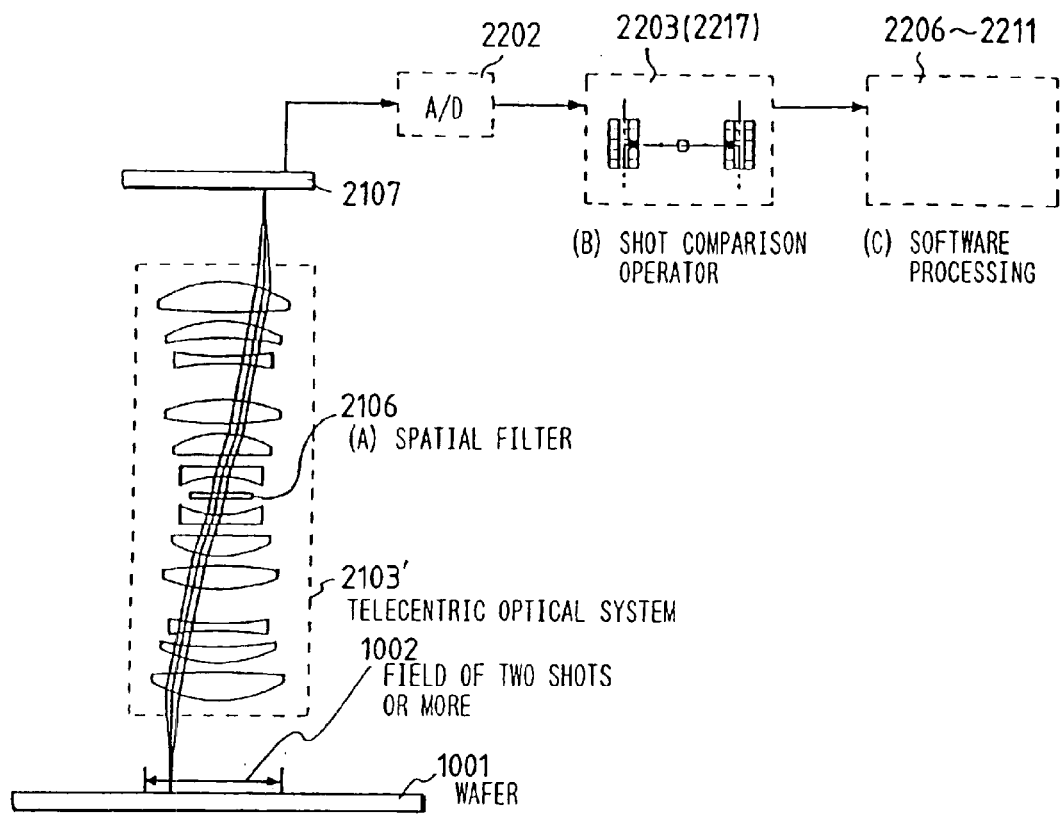

(A) SPATIAL FILTER
(B) SHOT COMPARISON OPERATOR
(C) SOFTWARE PROCESSING 2107
2106
2103' TELECENTRIC OPTICAL SYSTEM
1002 FIELD OF TWO SHOTS OR MORE
1001 WAFER

FIG. 31(b)(1)

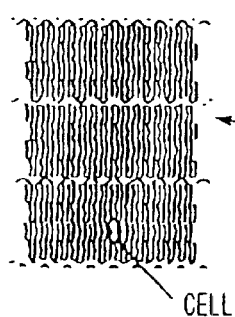

CELL (1) ERASING OF PATTERN USING SPATIAL FILTER

ERASE THE REPEATABILITY OF CELL USING SPATIAL FILTER

FIG. 31(b)(2)

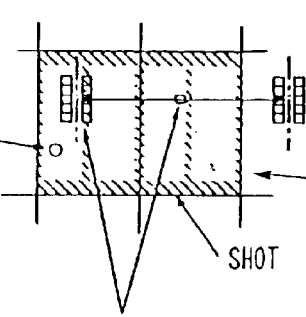

SHOT (2) ERASING OF PATTERN USING SHOT COMPARISON OPERATOR

ERASE USING THE REPEATABILITY OF TWO SHOTS

FIG. 31(b)(3)

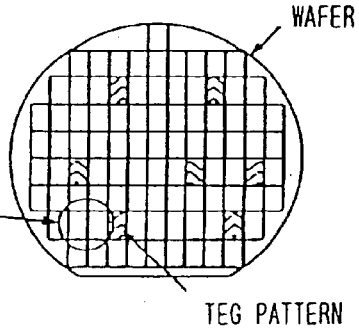

WAFER
TEG PATTERN (3) ERASING OF TEG PATTERN USING SOFTWARE

ERASE USING COORDINATE-MATRIX DATA

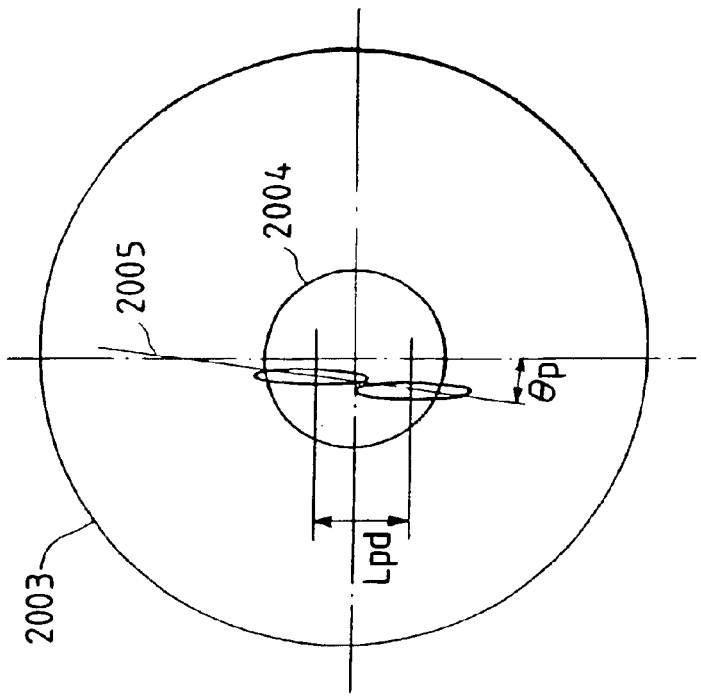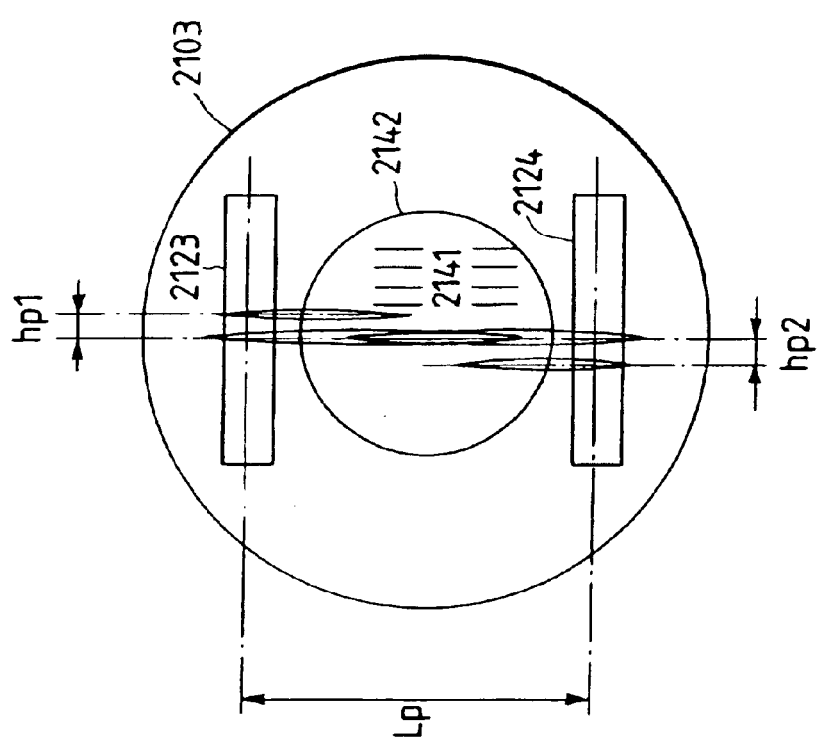

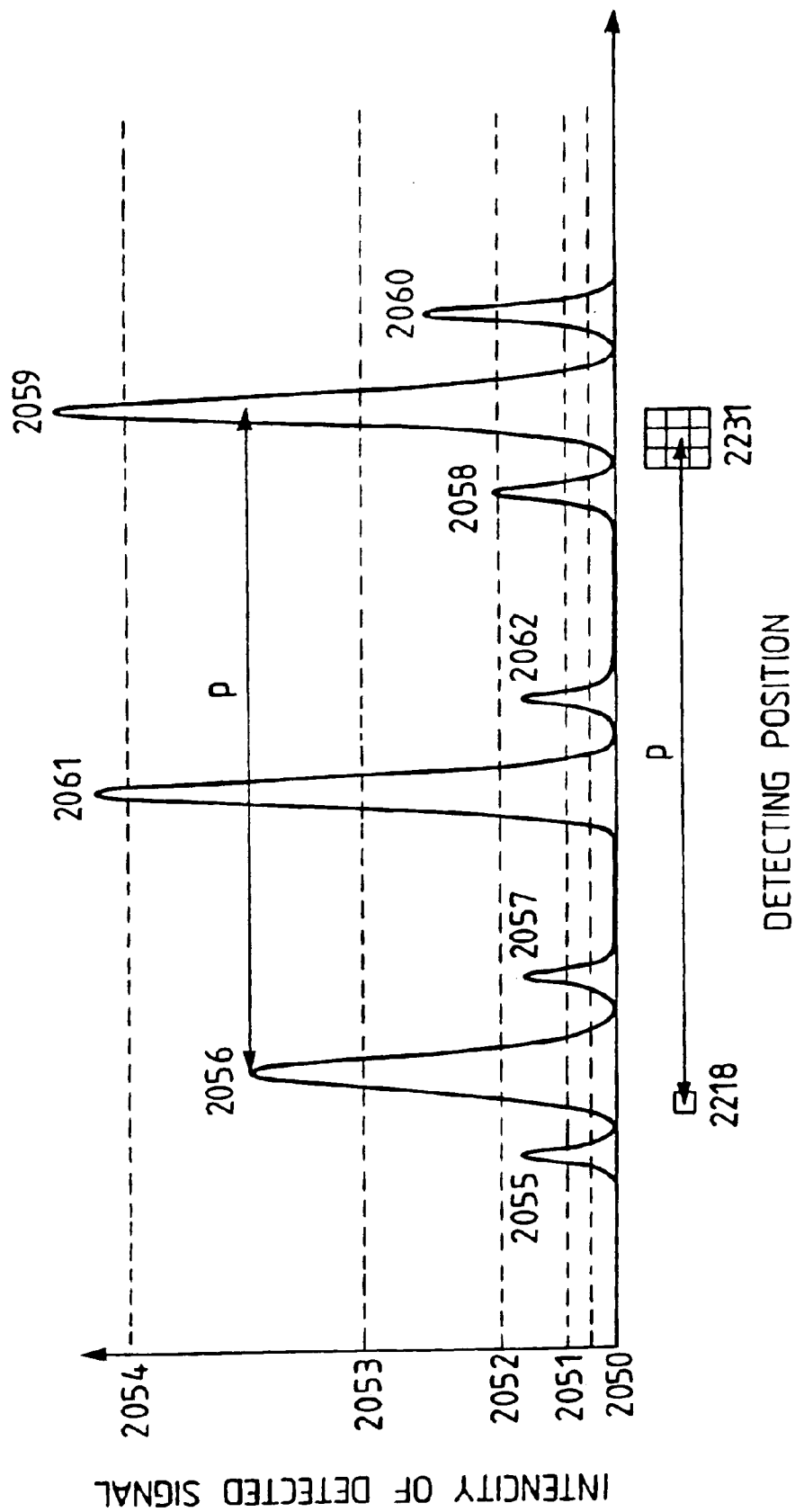

METHOD AND APPARATUS FOR ANALYZING THE STATE OF GENERATION OF FOREIGN PARTICLES IN SEMICONDUCTOR FABRICATION PROCESS

CROSS-REFERENCE TO RELATED APPLICATIONS

This application is a continuation application of U.S. application Ser. No. 08/535,577, filed Sep. 28, 1995, which is a continuation application of U.S. application Ser. No. 08/046,720, filed Apr. 16, 1993, now U.S. Pat. No. 5,463,459, which is a continuation-in-part of U.S. application Ser. No. 07/679,317, filed Apr. 2, 1991, now U.S. Pat. No. 5,233,191 and U.S. application Ser. No. 07/778,363, filed Oct. 17, 1991, now U.S. Pat. No. 5,274,434. U.S. application Ser. No. 07/778,363 being a continuation-in-part application of U.S. application Ser. No. 07/679,317.

BACKGROUND OF THE INVENTION

The present invention relates to a method and apparatus for analyzing the state of generation of foreign particles in a semiconductor fabrication process, more particularly, detecting and analyzing foreign particles generated in a mass production starting line and a mass production line of the said process and taking an appropriate countermeasure, or a foreign particle inspecting apparatus for inspecting foreign particles on a semiconductor substrate.

In the conventional semiconductor fabrication process, if foreign particles are present on a semiconductor substrate (wafer), they will cause defects such as defective insulation of wiring and short-circuit. Further, in the case where a fine foreign particle is present in a semiconductor substrate provided with very fine semiconductor elements, such foreign particle will cause breakdown of an insulating film of a capacitor or a gate oxide film. Foreign particles are generated by various causes and in various conditions; for example, they are generated from an operating portion of a conveyance system, generated from the human body, or result from reaction in a processing apparatus using a process gas, or are already incorporated in chemicals, materials, etc.

A conventional method for detecting such foreign particles on a semiconductor substrate is disclosed in Japanese Patent Laid Open No. 89336/87, which method comprises radiating a laser beam onto the semiconductor substrate, detecting a scattered light from foreign particles if deposited on the substrate, then comparing the result with the result of inspection of the same type of a semiconductor substrate conducted just before, thereby eliminating a false information based on pattern and permitting a foreign particle inspection of high sensitivity and high reliability. Also in Japanese Patent Laid Open No. 135848/88 there is disclosed a method which comprises radiating a laser beam onto a semiconductor substrate, detecting a scattered light from foreign particles if deposited on the substrate, and then analyzing the detected foreign particles using an analyzing technique such as laser photoluminescence or secondary X-ray analysis (XMR).

In the above conventional methods, distinction is made between a mass production starting line and a mass production line in a semiconductor fabrication process, and an inspection apparatus used in the mass production starting operation is applied as it is to the mass production line, so it is necessary in the mass production line to detect the generation of foreign particles and take a countermeasure as soon as possible. However, the conventional inspection apparatus is a Stand-alone type and the semiconductor substrate which has been processed in the fabrication line is carried to the installed place of the inspection apparatus and inspected there for foreign particles. Thus, it takes time for conveyance of the semiconductor substrate and for the inspection of foreign particles, so that it is difficult to increase the inspection frequency up to a sufficient value.

In the prior art, in addition to the large scale of equipment, a long time is required for the inspection, so for realizing a real-time monitor using such conventional apparatus, it is necessary to arrange a large number of large-sized apparatus, but actually this has been difficult. Actually it has been possible to inspect at most one or several lots or one sheet of a semiconductor substrate a day. In such a frequency of foreign particle inspection, it cannot be said that the generation of foreign particles is detected sufficiently rapidity. Such inspection in the prior art has been remote from the ideal real-time sampling in the mass production line. Further, for decreasing the number of steps in the mass production line and for diminishing equipment, it has been necessary to provide a required and sufficient number of monitors in a required and sufficient number of places. This has also been a subject to be attained.

One of main mass production starting operations for LSI is an operation of clearing up the cause of generation of such foreign particles and taking a countermeasure. In this connection, detecting foreign particles and analyzing the kind of element, etc. is an important clue to clear up the cause of their generation. On the other hand, in the mass production line, it is necessary to detect the generation of foreign particles and take a countermeasure as soon as possible. As time elapses from the generation of foreign particles up to the detection thereof, the number of defects generated increases and hence the yield lowers. Therefore, in order to maintain a high yield, it is absolutely necessary to shorten the time elapsed from the generation of foreign particles until the detection thereof. In other words, in order to maximize the effect of the foreign particle inspection, it is necessary to shorten the sampling time in a monitor, and ideally it is desirable to perform a real-time sampling for the mass production line.

SUMMARY OF THE INVENTION

It is the object of the present invention to provide a method and apparatus for analyzing the state of generation of foreign particles in a semiconductor fabrication process of a mass production line, which apparatus is installed at an inlet or outlet of a processing apparatus or in a conveyance system between plural processing apparatus so as to permit detecting the state of generation of foreign particles on a semiconductor substrate in real time.

In one aspect of the present invention, a real-time sampling is realized, and a foreign particle monitoring unit used therein is small-sized so that it can be installed at an inlet or outlet of a processing apparatus in a semiconductor fabrication line or in a conveyance system between processing apparatus. More specifically, according to one aspect of the present invention there is provided an apparatus for analyzing the state of generation of foreign particles in a semiconductor fabrication process, characterized in that, in a semiconductor mass production line provided with plural processing apparatus, a foreign particle monitoring unit for detecting the state of generation of foreign particles on a semiconductor substrate is installed at an inlet or outlet of a predetermined processing apparatus or in a conveyance system between plural processing apparatus to detect the state of generation of foreign particles on the semiconductor substrate in the processing apparatus, the foreign particle monitoring unit including an oblique lighting system constituted by an illumination array, a focusing optical system constituted by a lens array or a group of microlenses, a spatial filter disposed on a Fourier transform plane of the focusing optical system, a detector disposed in a focused position of the focusing optical system, and an erasing means for erasing pattern signals which are produced repeatedly on the substrate, and also provided is a method for such analysis.

In another aspect of the present invention there is provided a foreign particle inspecting apparatus for inspecting foreign particles on a semiconductor substrate, the foreign particle inspecting apparatus including a lighting system for illuminating the semiconductor substrate in a substantially linear shape with plane wave of a short wavelength, a focusing optical system for focusing a reflected light image from the semiconductor substrate thus illuminated by the lighting system, a spatial filter mounted halfway in the focusing optical system so as to intercept a diffracted light from repetitive patterns on the substrate, a detector for detecting the focused light image, an erasing means for erasing a signal which is produced repeatedly on the substrate out of signals detected by, the detector, and a foreign particle detecting means for detecting foreign particles on the substrate on the basis of a signal which had not been erased by the erasing means. In this foreign particle inspecting apparatus, moreover, the present invention is characterized in that the focusing optical system is constituted by a lens array of a refractive index changing type.

In a further aspect of the present invention there is provided a defect detecting apparatus including a lighting system for illuminating a substrate having repetitive patterns of different pitches, linearly using a plane wave light, a focusing optical system for focusing a reflected light image from the substrate thus illuminated by the lighting system, a spatial filter installed halfway in the focusing optical system so as to intercept a diffracted light from repetitive patterns of a small pitch, a detector for detecting a light image obtained through the spatial filter and focused by the focusing optical system, an erasing means which compares signals with each other obtained through the spatial filter and on the basis of repetitive patterns of a large pitch and erases a signal, and a defect detecting means for detecting a defect on the substrate on the basis of a signal provided from the erasing means, and also provided is a defect detecting method associated therewith.

In a still further aspect of the present invention there are provided an apparatus and a method according to the above defect detecting apparatus and method in which the erasing means has a processing means which, in judging whether a signal of one picture element on the detector is defective or not, compares the signal level of one picture element on the detector with the signal level of a picture element present in a corresponding position of adjacent repetitive pattern which has been taken in by the detector and those of plural picture elements present in close proximity to the said corresponding position, and in the case where a picture element of an equal value to the signal level of the said one picture element is present among the signal levels in the said corresponding position or proximate position, judges that the detected signal of one picture element on the detector is a signal from repetitive pattern.

In a still further aspect of the present invention there is provided a defect detecting apparatus including a conveying means for the conveyance of a substrate having repetitive patterns, a lighting system for radiating light of a plane wave linearly to the substrate being conveyed by the conveying means, a focusing optical system for focusing a reflected light image from the substrate thus illuminated by the lighting system, a spatial filter disposed in a focused position halfway of the focusing optical system so as to intercept a diffracted light from repetitive patterns on the-substrate, the spatial filter comprising a plurality of linear shields disposed so as to be variable in their spacing, a detector for detecting a light image obtained through the spatial filter and focused by the focusing optical system, and a defect detecting means for detecting a defect on the substrate on the basis of a signal detected by the detector.

The present invention is an improvement over U.S. Ser. No. 07/778,363.

At the time of starting of mass production in a semiconductor fabrication process, each process and equipment are evaluated by means of an evaluation equipment of high performance which is expensive, for making evaluation and debug of material, process, apparatus and design, and at the time of mass production, the number of processes and equipment in the production line are minimized, particularly the number of inspection and evaluation items is decreased to reduce the equipment cost and shorten the time required for inspection and evaluation. To this end, various considerations are given to permit a smooth and quick evaluation at the time of starting of mass production. For example, sampling is made along this line or a semiconductor substrate is inspected using an improved foreign particle detecting and analyzing system to clear up the cause of generation of foreign particles, then the specification of inspection in the acquisition of materials is changed or a certain measure is taken against a dust generation source on the basis of the result obtained, which result is fed back to each material, process and apparatus to, for example, change the specification of a dust-prone process into a design of elements which strong against the generation of dust. At the same time, such result is utilized in preparing specifications for inspection and evaluation in the mass production line, and where required, a monitor for foreign particles on a semiconductor substrate is mounted in a place where foreign particles are apt to occur, or a specification is prepared to monitor only increase and decrease of specific foreign particles present in a specific place.

By thus separating the mass production starting line and the mass production line from each other, it is made possible to effect an efficient operation of the apparatus for detecting, analyzing and evaluation foreign particles at the time of starting of mass production and hence it is possible to perform the mass production starting work rapidly. Besides, the reduction in weight of the mass production line can be attained by using a minimum required number of monitoring apparatus of a simple structure as the foreign particle inspecting and evaluating apparatus used in the mass production line.

In connection with the above monitoring apparatus used in the mass production line according to the present invention, we have paid attention to the following method in order to realize, using the existing technique, a small-sized, high-speed inspection apparatus having an equal function to that of the conventional large-sized apparatus. First, the repeatability of memory was noted. Heretofore, a method of removing repetitive patterns and detecting defects has been known. This conventional method ensures a detection performance. However, no convenient point has been referred to about such method in realizing the said monitoring apparatus. Further, it is not necessary to monitor all of points on a semiconductor substrate, but it suffices to monitor the upper surface of the substrate at a certain specific ratio. In the manufacture of a memory having lots of repetitive patterns, even a mere monitor of only the repetitive portion of the memory is very effective.

In repetitive patterns, the radiation of a coherent light causes exit of light only in a certain specific direction. More particularly, in the case of memory, light emerging in a specific direction from a repetitive portion can be intercepted using a spatial filter and it is possible to detect, in high sensitivity, foreign particles which are not apt to occur repeatedly. In this case, if liquid crystal is used as the spatial filter, the shape of the spatial filter can be changed as desired by turning on-off of the liquid crystal and therefore it is possible to inspect any repetitive pattern automatically.

The reason why the yield in semiconductor fabrication is improved by the above means is as follows. As a result of a strict experiment for detecting the number of foreign particles on a semiconductor substrate, it turned out that the number of foreign particles increased or decreased suddenly, not gradually. Heretofore, since the number of foreign particles has been considered to increase or decrease gradually, the inspection of foreign particles has been conducted at a frequency of one lot or one sheet a day as noted previously. In such a low inspection frequency, however, a sudden increase in the number of foreign particles will be overlooked, or detection may be made in a little while after the increase, thus resulting in occurrence of a considerable number of defects. That is, in the mass production line, it is necessary to detect the generation of foreign particles and take a countermeasure as soon as possible. With the lapse of time from the generation of foreign particles until detection thereof, the number of defects generated increases and the yield lowers. In other words, a high yield can be ensured by shortening the time elapsed from the time when foreign particles are generated until when the generation is detected. That is, the effect of the foreign particle inspection can be exhibited to the maximum extent by shortening the sampling time in monitor..or ideally by sampling in real time.

In the conventional apparatus, moreover, a semiconductor substrate is pulled out for inspection and in this case foreign particles will newly be deposited on the semiconductor substrate, thus also resulting in lowering of the yield. On the other hand, the foreign particle inspection apparatus according to the present invention permits the inspection without the need of pulling out a semiconductor substrate, so that there will be no lowering of the yield caused by the deposition of foreign particles on the substrate.

BRIEF DESCRIPTION OF THE DRAWINGS

FIGS. 1(a)–1(c) are diagrams showing a relation between detected picture element size and noise level according to the present invention;

FIGS. 7(a)–7(c) are performance diagrams for deciding apparatus specifications according to the present invention;

FIGS. 25(a)–25(c) are construction diagrams showing an example of a detection head illustrated in FIG. 24;

FIGS. 30(a)–30(d) are construction diagrams showing a basic concept of the present invention;

FIGS. 31(a) and 31(b)(1)–31(b)(3) are construction diagrams showing a pattern removing method according to the present invention;

FIGS. 34(a) and 34(b) are construction diagrams showing a rotational deviation detecting system according to the present invention;

FIG. 43 is a diagram explanatory of a signal processing method according to the present invention.

DETAILED DESCRIPTION OF THE PREFERRED EMBODIMENTS

The present invention is an improvement over U.S. Ser. No. 07/778,363 and therefore the contents described in the U.S. Ser. No. 07/778,363 will here be omitted.

In realizing a small-sized, high-speed, foreign particle inspection apparatus, the method using a spatial filter is more suitable than the polarized light detection method shown in the prior art (Japanese Patent Laid Open No. 89336/87). The reason for this conclusion will be stated below with reference to FIGS. 1, 2 and 3.

In the method wherein light is radiated to a sample and scattered light from foreign particles is detected in the scattered light from patterns formed on the sample surface causes noise. The larger the size of a picture element (a minimum unit detected as one signal) in a detector 2006, the larger the said noise, as shown in FIG. 1(c). Since the patterns as a noise source are formed substantially on the whole surface of the sample, the noise becomes larger in proportion to the picture element size.

On the other hand, the larger the number of picture elements, the longer the time required for inspection, so in order to realize a high-speed inspection it is necessary to enlarge the picture element size. Thus, it is necessary to enlarge the picture element size and lower the noise level. As a method for lowering the noise level, a method utilizing polarized light is described in Koizumi et al., "Analysis of Reflected Light from LSI Wafer Pattern," Collected Papers, Instrumentation Automatic Control Society, 17-2, 77/82 (1981). According to this method, scattered light (noise) from pattern can be attenuated by utilizing polarized light. However, the attenuation factor of scattered light in the said method depends on the direction of a detector, as analyzed in the above paper. Therefore, in the case of condensing light rays which have been emitted in various directions, as in the use of a focusing optical system, integration of respective attenuation factors gives values in the range from about 0.1% to about 0.01%.

Figure 2:
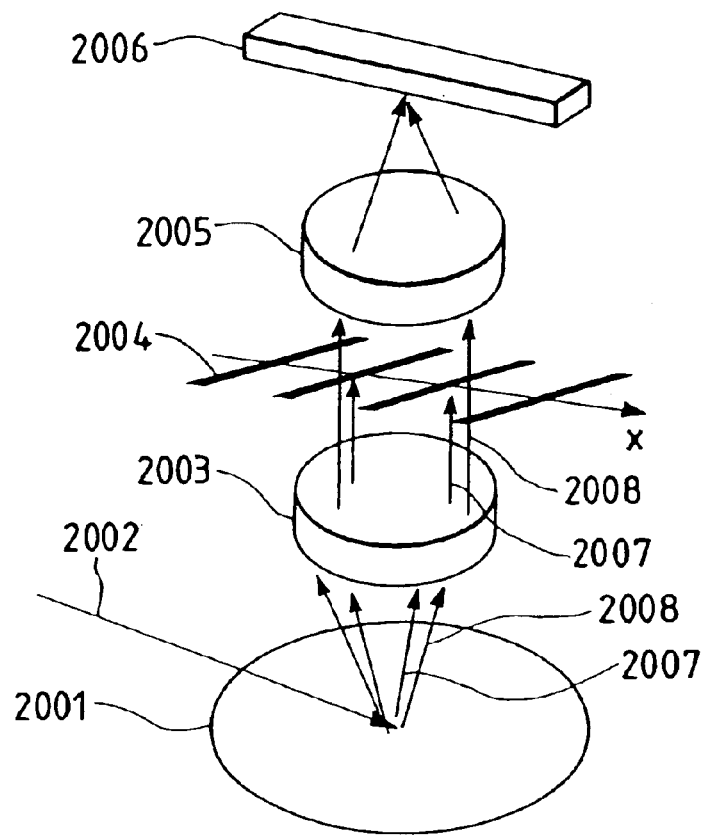
FIG. 2 is a construction diagram of a foreign particle detecting optical system using a spatial filter according to the present invention.
Figure 3:
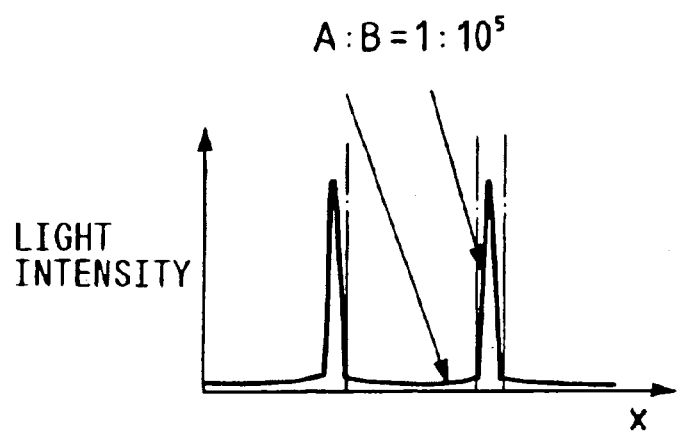
FIG. 3 is a diagram showing a light intensity distribution on a spatial filter surface according to the present invention.

On the other hand, in the method using a spatial filter according to the present invention, it is possible to obtain an attenuation factor in the range from 0.001% to 0.0001%. The reason for this will now be explained with reference to FIGS. 2 and 3. A wafer 2001 with repetitive patterns formed thereon is illuminated with an illuminating light 2002, and the thus-illuminated area is focused on a detector 2006 through lenses 2003 and 2005. FIG. 3 shows an intensity distribution of light reflected from patterns on a Fourier transform plane with a spatial filter 2004 provided thereon. The light from the repetitive patterns is concentrated on a position corresponding to the pattern pitch. As an example of having calculated a ratio of such light concentration, a diffracted light intensity distribution in the use of slits is explained in Hiroshi Kubota, "Applied Optics," (Iwanami). According to the explanation given therein, the larger the number of slits (the number of simultaneously illuminated repetitive patterns in the present invention), the larger the ratio of light concentration. This ratio can be calculated also by using Fourier transform. If the shape of illuminated patterns is a (x, y), the light intensity distribution in the position of the spatial filter is F [a (x, y)]. If the shape of the spatial filter is assumed to be p (u, v), then p (u, v)*F (a (x, y)] represents the light which passes through the spatial filter. If the shape of a figure complementary to the spatial filter is assumed to be $\bar{p}$ (u, v), then $\bar{p}$ (u, v)*F [a (x, y)] represents a light component which is shielded by the spatial filter. The ratio of these two components corresponds to the foregoing attenuation factor. When the number of patterns repeated is 3, the attenuation factor is calculated to be about 0.001%, and when the number of patterns repeated is 5, the attenuation factor is about 0.0001%. With a further increase in the number of repetition, the attenuation factor decreases. Thus, the attenuation factor can be made lower than that in the use of polarized light, and hence it is possible to reduce the pattern noise.

The above calculations are of the case where the pattern shape and other conditions are ideal, and so there is the possibility that they will not always be coincident with the results of actual experiments. However, we have obtained experimental results showing that the attenuation factor lowers by one to three digits in comparison with the method using polarized light and hence it is possible to reduce the pattern noise.

An example of a small-sized foreign particle monitor according to the present invention will now be described with reference to FIGS. 1 to 4. FIG. 1 shows a relation between a detector picture element size in a foreign particle detector and noise level. Attaining high speed and reduction of size is a subject relating to small-sized foreign particle monitors. FIG. 1(a) shows a foreign particle detecting optical system. Scattered light from patterns and foreign particles from a wafer 2001 is detected by a detector 2006 through a detection lens 2003. A detected signal from the detector 2006 is outputted at every picture element in the detector. FIG. 1(b) shows both the case where the size on the wafer corresponding to one picture element in the detector 2006 is small and the case where it is large. If the wafer area is S, data pick-up time in the detector is t, picture element size in the detector is w and the number of picture elements in the detector is n, then detection time T is expressed by the following equation (Equation 1):

$$T = (S \cdot t)/(w \cdot n) \qquad (1)$$

From Equation 1 it is seen that enlarging w and increasing n to effect parallel processing are most effective in realizing high speed and small size. As shown in FIG. 1(c), however, if w is enlarged, the noise level from pattern on the wafer 2001 also increases in proportion to w. Therefore, in order to increase w and maintain the foreign particle detecting performance, it is necessary to reduce the noise level.

In view of this point, the following description is now provided about the effect of using a spatial filter for reducing the noise level from patterns. FIG. 2 is a construction diagram of a foreign particle detecting optical system using a spatial filter, in which a spatial filter 2004 is provided on a Fourier transform plane of a detection lens 2003.

Diffracted light 2007 from a memory pattern having repetitiveness on the wafer 2001 and causing noise passes through the detection lens 2003 and is then shielded by the spatial filter 2004. On the other hand, scattered light 2008 from foreign particles on the wafer 2001 passes through the detection lens 2003, spatial filter 2004 and focusing lens 2005 and is detected by a detector 2006.

FIG. 3 shows a light intensity distribution in x direction of the pattern diffraction light 2007 on the surface of the spatial filter 2004. In the same figure, the ratio in the intensity of the pattern diffraction light 2007 at a light transmitting portion (A) and a light shielding portion (B) of the spatial filter 2004, namely, A:B, is $1:10^5$, and thus the provision of the spatial filter 2004 permits reduction of the pattern noise to $1/10^2$. In the polarizing filter method used in the conventional foreign particle inspection apparatus, the reduction in pattern noise is $1/10^2$, so in comparison with the conventional apparatus, the noise reduction level is improved by $10^3$ and the foreign particle detecting sensitivity is also improved, assuming that both apparatus are the same in the picture element size in detector. Therefore, by setting the target of foreign particle detecting sensitivity to a value below the sensitivity in the conventional foreign particle inspection apparatus, it is made possible to enlarge the picture element size in detector and realize a foreign particle detecting optical system of high speed and small size.

It is a memory pattern having repetitiveness that can be shielded by the spatial filter, so the other portion than the memory pattern portion is made into an invalid data or detection inhibition area using software for example on the basis of design data, i.e. CAD data, exposure data.

Figure 4:
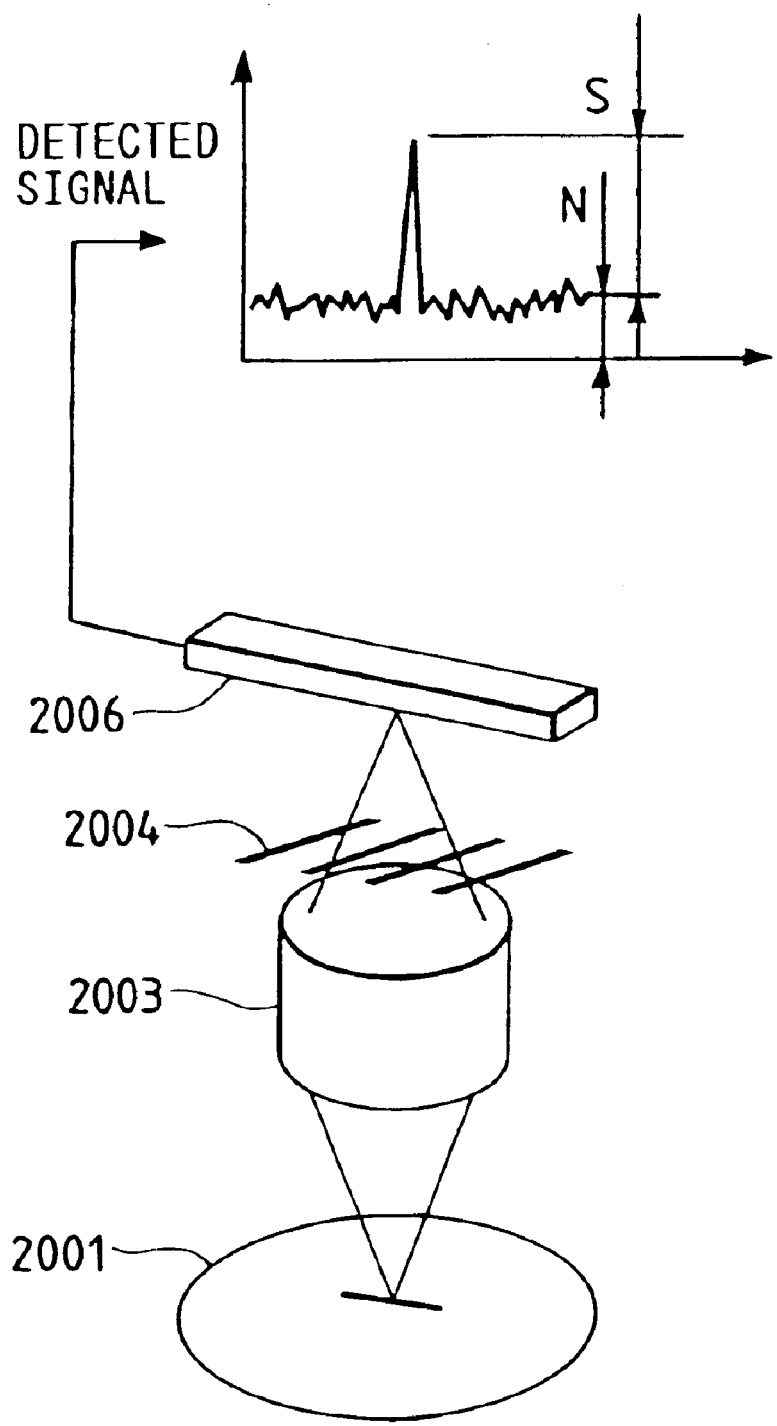
FIG. 4 is a diagram showing a discrimination ratio in the foreign particle detecting optical system according-to the present invention.
Figure 5:
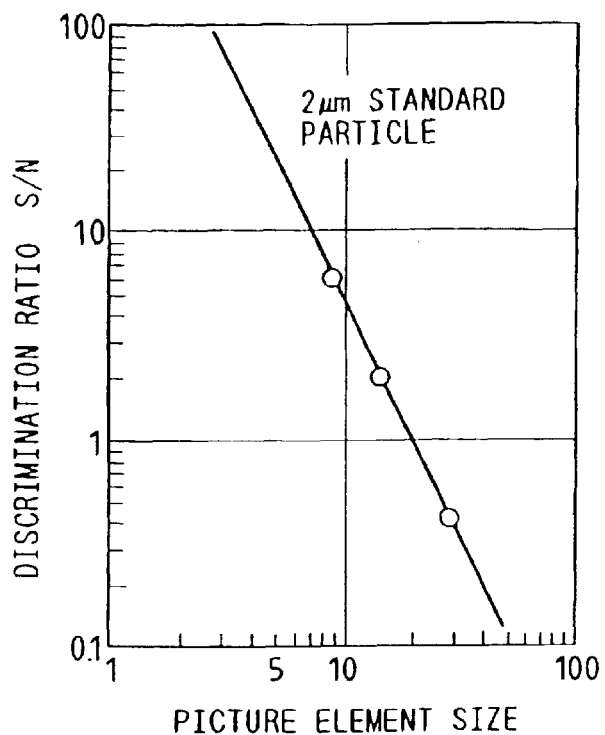
FIG. 5 is a diagram showing a relation between detected picture element size and discrimination ratio according to the present invention.

FIG. 4 shows a discrimination ratio in a foreign particle detecting optical system to which is applied a spatial filter method. Since a detection lens 2003 used in this optical system also serves as a focusing lens, it is not necessary to provide any special focusing lens. In a detected signal distribution from a detector 2006, if a foreign particle detected signal is S and pattern noise is N, a discrimination ratio is represented by S/N. Referring now to FIG. 5, there is illustrated a relation between detector picture element size and discrimination ratio, in which a standard particle of 2 $\mu$m is shown as an example of foreign particle. In order to discriminate a foreign particle stably from pattern, it is necessary that the discrimination ratio be 1 or more. From the same figure, therefore, it is seen that the detector picture element size should be 20 $\mu$m or smaller in order to discriminate and detect the standard 2 $\mu$m particle from pattern.

Figure 6:
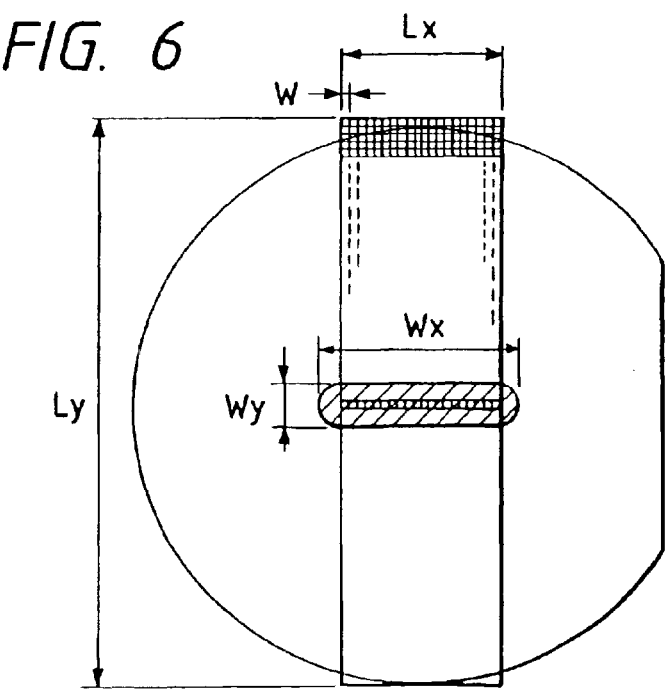
FIG. 6 is a diagram showing an illumination area and a detection area according to the present invention.

Referring next to FIG. 6, there are shown an illumination area and a detection area. If inspection widths are Lx and Ly, picture element size in detector is w and read clock frequency of the detector is f, an inspection time T is expressed as follows (Equation 2):

$$T = (Lx \cdot Ly/w^2) \cdot (1/f) \qquad (2)$$

Further, if illumination power is $P_0$ and illumination widths are Wx and Wy, an effective illumination light intensity P is expressed as follows (Equation 3):

$$P = P_0 \cdot (w \cdot Lx)/(Wx \cdot Wy) \qquad (3)$$

Since Wx≈Lx, Equation 3 can be expressed as follows (Equation 4):

$$P = P_0 \cdot (w \cdot Wy) \qquad (4)$$

From Equations 2 and 4, a total illumination light quantity Pt is expressed as follows (Equation 5):

$$Pt = T \cdot P = P_0 \cdot (Lx \cdot Ly \cdot Wy) \cdot (1/(w \cdot f)) = K_1 \cdot (1/(w \cdot f)) \qquad (5)$$

Therefore, from a foreign particle signal coefficient $K_2$ and Equation 5, a detected signal intensity I is expressed as follows (Equation 6):

$$I = K2 \cdot Pt = K_1 \cdot K_2 \cdot (1/(W \cdot f)) \qquad (6)$$

From Equation 6, 1 becomes a function of w·f.

FIG. 7 is a performance diagram for determining an apparatus specification on the basis of the results obtained above. More specifically, an apparatus specification is determined from three figures respectively showing a relation between picture element size and inspection time, a relation between picture element size and discrimination ratio, and a relation between picture element size x detector clock frequency and detected signal. For example, for realizing an inspection time of 20 seconds, a detector picture element size of 13 $\mu$m will do if the detector clock frequency is set at 2 MHz from the relation of picture element size and inspection time. In this case, from the relation of picture element size and discrimination ratio, a discrimination ratio of 2 $\mu$m foreign particle from pattern is 2 and it is possible to make discrimination from pattern. Lastly, from the relation between picture element size x detector clock frequency and detected signal, a detected signal of 2 $\mu$m foreign particle is 60 mV, determined by the picture element size× clock frequency, and it is possible to detect it by the detector. Thus, on the basis of the three performance diagrams, it is possible to determine specifications of a foreign particle size for detection and inspection time in the apparatus.

Figure 8:
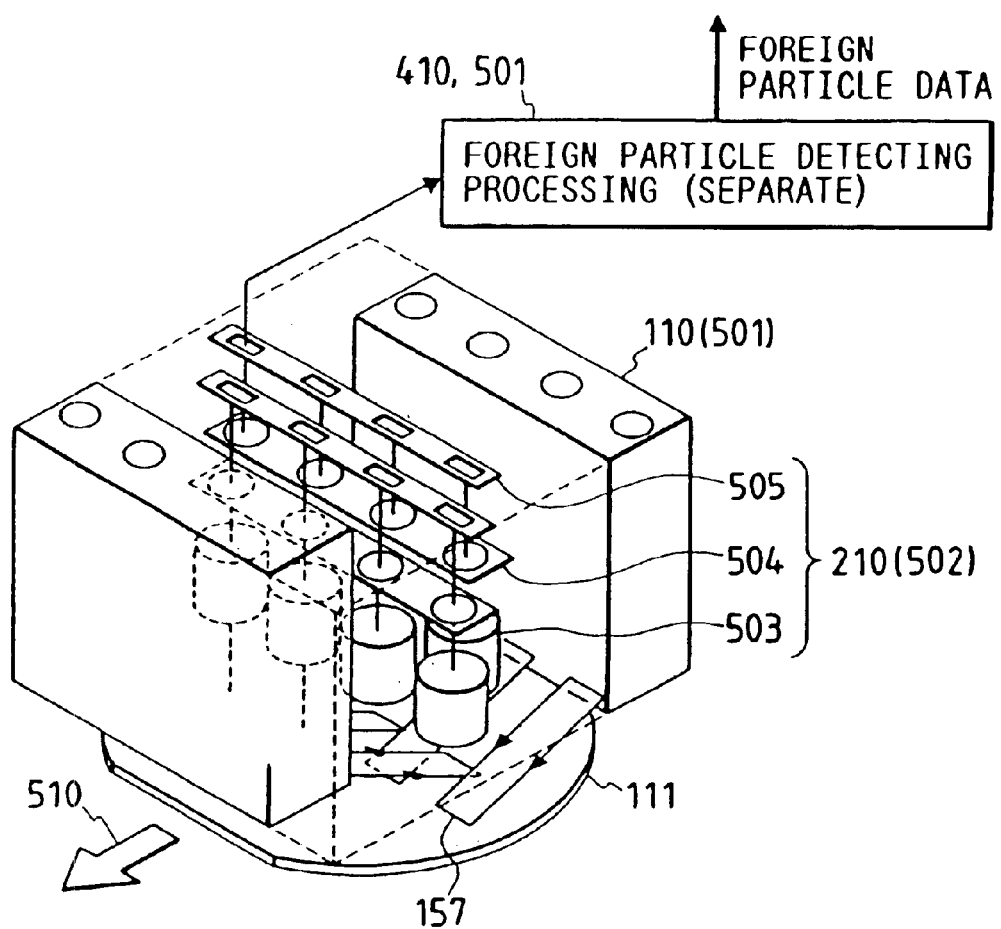
FIG. 8 is a diagram showing an apparatus construction of a foreign particle detecting optical system according to the present invention.

FIG. 8 is a construction diagram of a foreign particle detecting optical system using a spatial filter method. The foreign particle detecting optical system is of a construction wherein the whole surface of a product wafer 111 can be inspected by a uniaxial scan 510 on the wafer. More specifically, the optical system is divided into an illuminating optical system 110 (501) and a detecting optical system 210 (502), which systems each have a unit construction. Description is now directed to the case where the wafer 111 to be inspected is 200 mm in diameter. For example, in the case where inspection is to be made for the entire width of the wafer 111 using eight units, an illumination and detection area 157 of one unit should be 25 mm. Therefore, when the wafer 111 is 150 mm in diameter, it suffices to use six units out of the eight units. The detecting optical system 210 (502) of one unit comprises a detection lens 503, a spatial filter 504 provided on a Fourier transform plane of the detection lens 503, and a linear sensor 505 serving as a detector. In the case where an external size of the detection lens 503 is larger than the detection width, the entire width of the wafer 111 can be covered by such a zig-zag arrangement as shown in FIG. 8. On the other hand, in the case of an external size of the detection lens 503 smaller than the detection width, or when a limited portion on the wafer is to be inspected, that is, in the case of a partial inspection, there may be adopted a linear arrangement. As the spatial filter 504 used herein, there are used two sets of a 4-unit construction in the case of a zig-zag arrangement of the detecting optical system 210 (502), while in the case of a linear arrangement of the optical system 210, there is used one set of an 8-unit construction. A detected signal from the linear sensor 505 is processed in a foreign particle detecting processing (separate) 401, 501 and is outputted as foreign particle data.

The replacement of two sets of spatial filters 504 in the case of a zig-zag arrangement of the detecting optical system 210, or one set in the case of a linear arrangement of the same optical system, should be done between kinds of the wafer 111, but it is possible cope with one kind of wafer using one kind of spatial filter 504, substantially independently of process.

An example of specification in this embodiment will now be shown. The illuminating optical system uses a semiconductor laser of wavelength 780 nm and output 200 mW as an illuminating light source, whereby an area of 26×1 mm² on the wafer is illuminated at an illuminating light incidence angle of 60° from above. In the detecting optical system, a projection lens [50 mm F2.8, detecting magnification: 1× (detecting NA 0.1)] is used as the detection lens. As the detector there is used a CCD linear sensor having a picture element size of 13 $\mu$m, 2,048 picture elements and a drive frequency of 4 MHz, or a CCD linear sensor having a picture element size of 7 $\mu$m, 4,096 picture elements and a drive frequency of 4 MHz and which exhibits a high foreign particle discriminating performance.

Figure 9A:
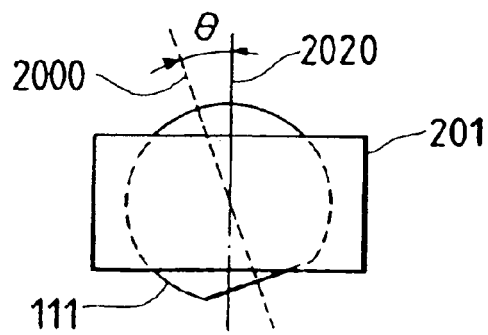
FIGS. 9(a) and 9(b) are diagrams showing an example of influence of a wafer rotational angle upon a pattern noise light according to the present invention.
Figure 9B:
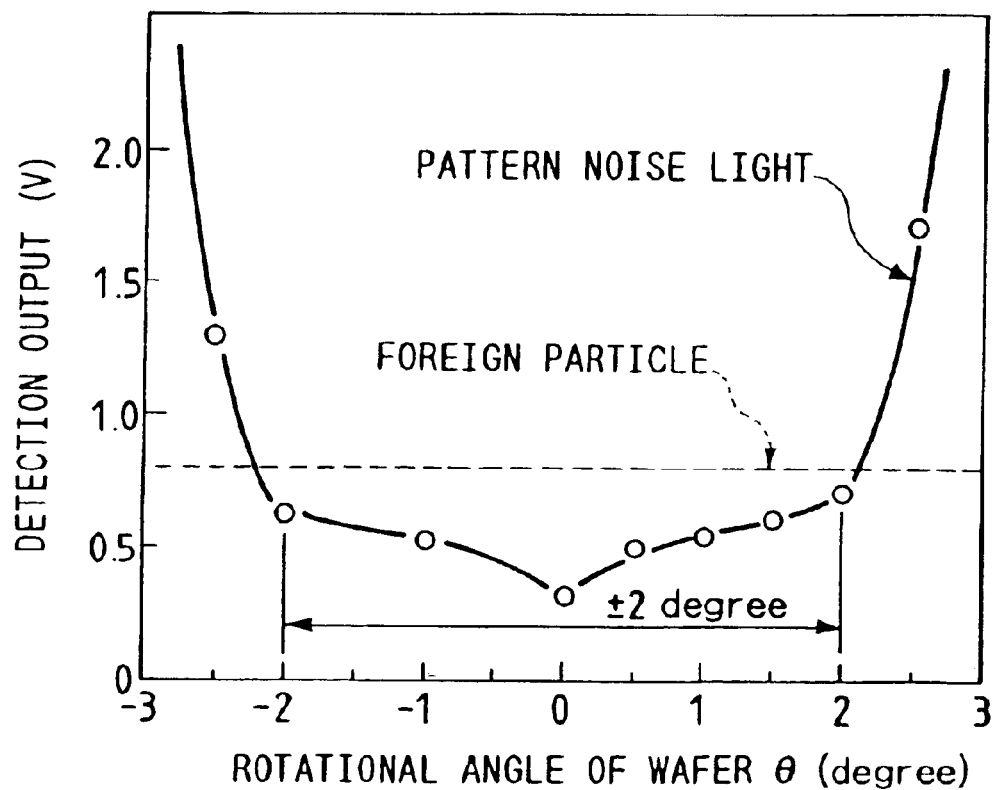

Referring now to FIG. 9, there is shown an example of influence of a wafer rotating angle on pattern noise light. As the wafer 111 rotates, a diffracted light from patterns on the wafer also rotates in accordance with the rotation of the wafer. Therefore, while the wafer 111 rotates with respect to the foreign particle detecting optical system 201, the diffracted light from patterns on the wafer leaks from the light shielding portion of the spatial filter, and hence the leakage light of such diffracted light, namely, pattern noise light, serves as a function of the light shielding width of the spatial filter and the rotational angle of the wafer. The rotational angle θ of the wafer represents an angle between a central line 2020 of the foreign particle detecting optical system 201 and a central line 2000 of the wafer 111. However, as the light shielding width of the spatial filter is made larger, the scattered light from foreign particles diminishes, so it is necessary to determine an optimum width. In the conventional pre-alignment device, the wafer rotating angle can be kept within ±2°, so in view of this point, FIG. 9 also shows an example of change of the pattern noise light caused by rotation of the wafer, assuming that a light shielding width of the spatial filter which permits a foreign particle of, say, 2 $\mu$m to be discriminated from pattern, as a foreign particle detecting performance, is an optimum width.

For obtaining the function as a foreign particle inspecting monitor, it is necessary to use a foreign particle detecting system having as large a focal depth as possible.

As to the focal depth, it is possible to obtain a value larger than a focal depth which is calculated from NA of the detection lens according to the detector picture element size.

If the detector picture element size is sufficiently smaller than the detected foreign particle size, the focal depth, d, depends on the numerical aperture of the detection lens and is expressed as follows (Equation 7) if the light wavelength is λ and the numerical aperture of the detection lens is NA:

$$d=0.5\cdot\lambda/(NA)^2 \quad (7)$$

In Equation 7, if λ=780 nm and NA=0.1, then d=39 $\mu$m. On the other hand, if the detector picture element size is sufficiently larger than the detected foreign particle size, the focal depth depends on the detector picture element size. In this case, if the detector picture element size is assumed to be an equivalent resolution a', a relation thereof to an equivalent numerical aperture NA' is expressed as follows (Equation 8):

$$a'=0.61\cdot\lambda/NA' \quad (8)$$

Further, substitution of NA' in Equation 8 into NA in Equation 7 gives an actual focal depth d. For example, if a'=13 $\mu$m, then NA'=0.037 and d=285 $\mu$m.

Thus, the increase in size of picture element in the detector is effective in enlarging the focal depth of the foreign particle detecting system.

Figure 10A:
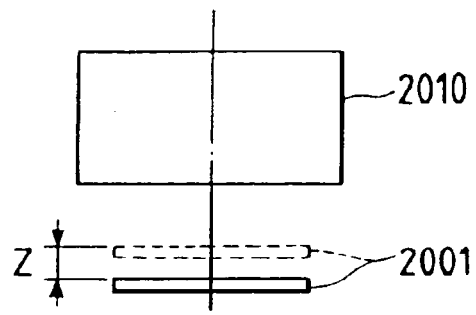
FIGS. 10(a) and 10(b) are diagrams showing an example of changes in a foreign particle detection output caused by changes in a wafer stage height according to the present invention.
Figure 10B:
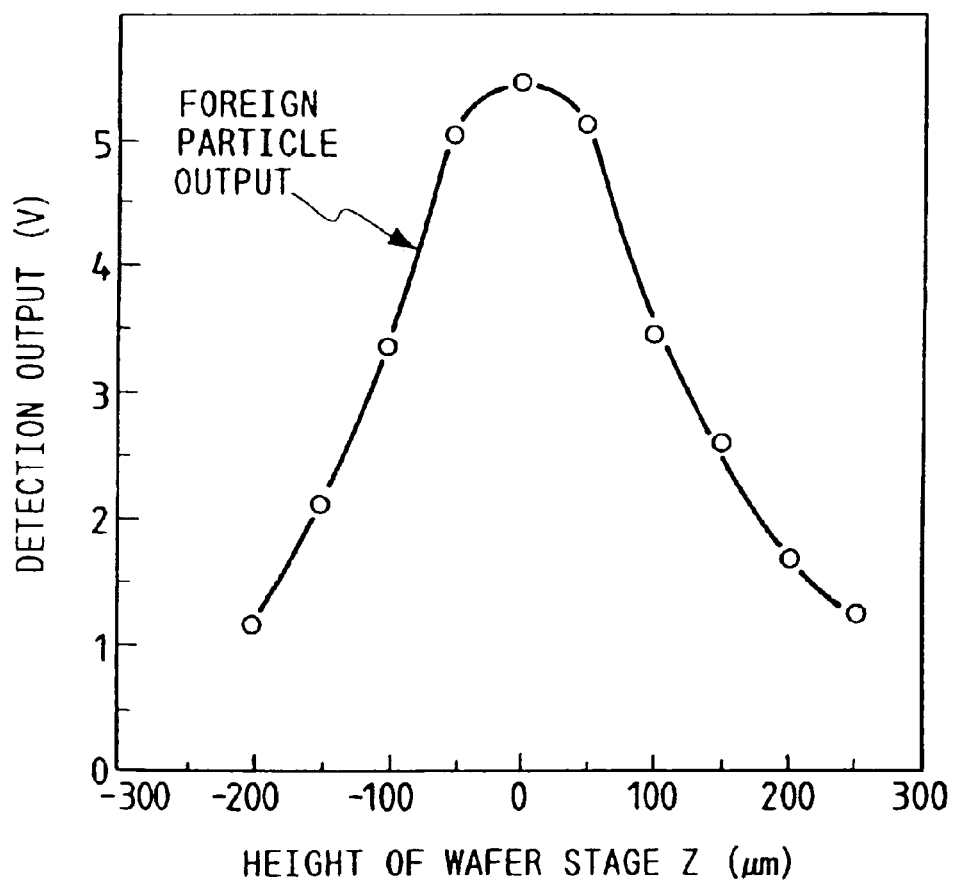

FIG. 10 shows an example of change in the foreign particle detection output caused by a change in height of the wafer stage. In the same figure there are shown changes in the detection output of 5 $\mu$m foreign particle in the case of λ=780 nm, NA=0.1 and detector picture element size 13 $\mu$m. From the same figure, a focal depth is ±70 $\mu$m. This value is an intermediate value between a value (39 $\mu$m) obtained from the numerical aperture of the detection lens and a value (285 $\mu$m) obtained from the detector picture element size. Thus, although the detector picture element size of 13 $\mu$m is not sufficiently large for the foreign particle of 5 $\mu$m, the focal depth is made large.

Thus, by making the numerical aperture of the detection lens small and enlarging the detector picture element size, it is made possible to enlarge the focal depth and hence it becomes possible to make a rough positional control in the height direction of the wafer conveying system.

Reference will now be made to the construction one unit of an illuminating optical system used in this small-sized foreign particle monitoring apparatus. According to this construction, one side on the wafer has a wide inspection area to permit sufficient illumination, while the other side is narrowed to provide a high illuminance, permitting a linear illumination. If the illuminating light source is a spot light source, plane wave or parallel light rays can be created on both sides. Using a collimated light as the illuminating light is advantageous in that the image in the spatial filter position of the detecting optical system can be made sharp and it is possible to enhance the light shielding performance of the spatial filter for pattern and so enhance the foreign particle detecting performance. However, in the case of using, for example, a small-sized semiconductor laser as the illuminating light source, one side of a luminous point becomes longer as the output becomes high. Consequently, a plane wave, or parallel light rays, is not created on one side. In view of this point, two types of illuminating optical systems will be described below, provided that in the linear illumination of the wafer, a longer beam direction is assumed to be y direction and a shorter beam direction, x direction.

Figure 11A:
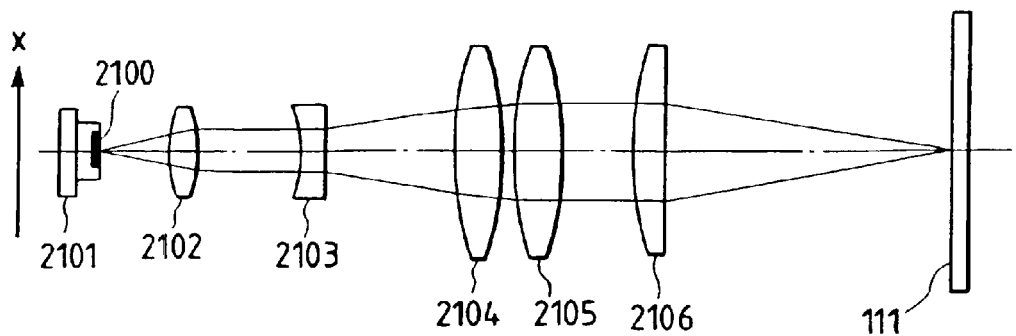
FIGS. 11(a) and 11(b) are side views of a lighting unit according to the present invention.
Figure 11B:
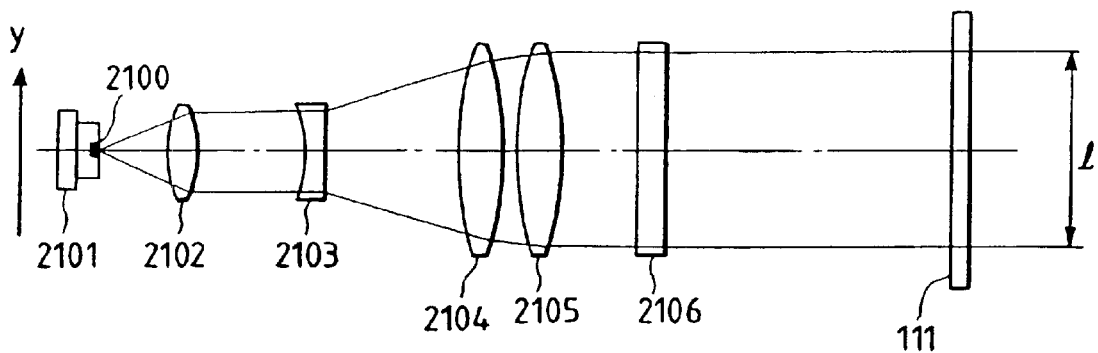

The construction of one type of optical system is illustrated in FIG. 11, in which (a) shows the construction as seen in the x direction and (b) shows the construction as seen in the y direction. A longer direction of a luminous point 2100 of a semiconductor laser 2101 is x direction, while a shorter direction (closer to the spot light source) of the luminous point 2100 is y direction, provided if the illumination on the wafer is P-polarized light illumination, a λ/2 plate is inserted for S-polarized light illumination.

Figure 12A:
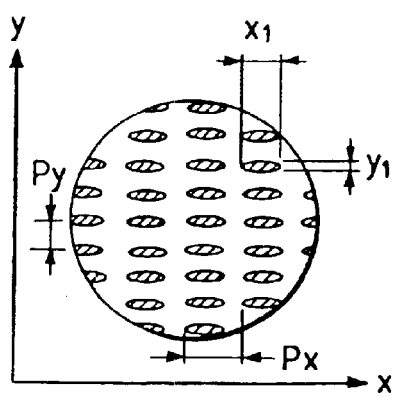
FIGS. 12(a) and 12(b) are plan views of a diffraction pattern on a spatial filter surface according to the present invention.
Figure 12B:
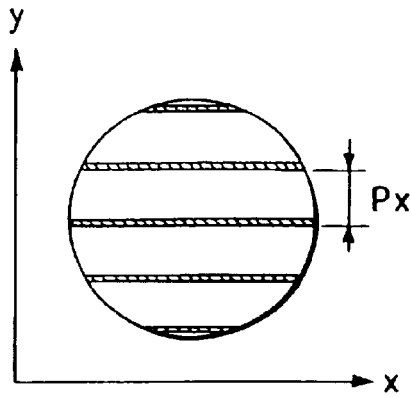
Figure 19:
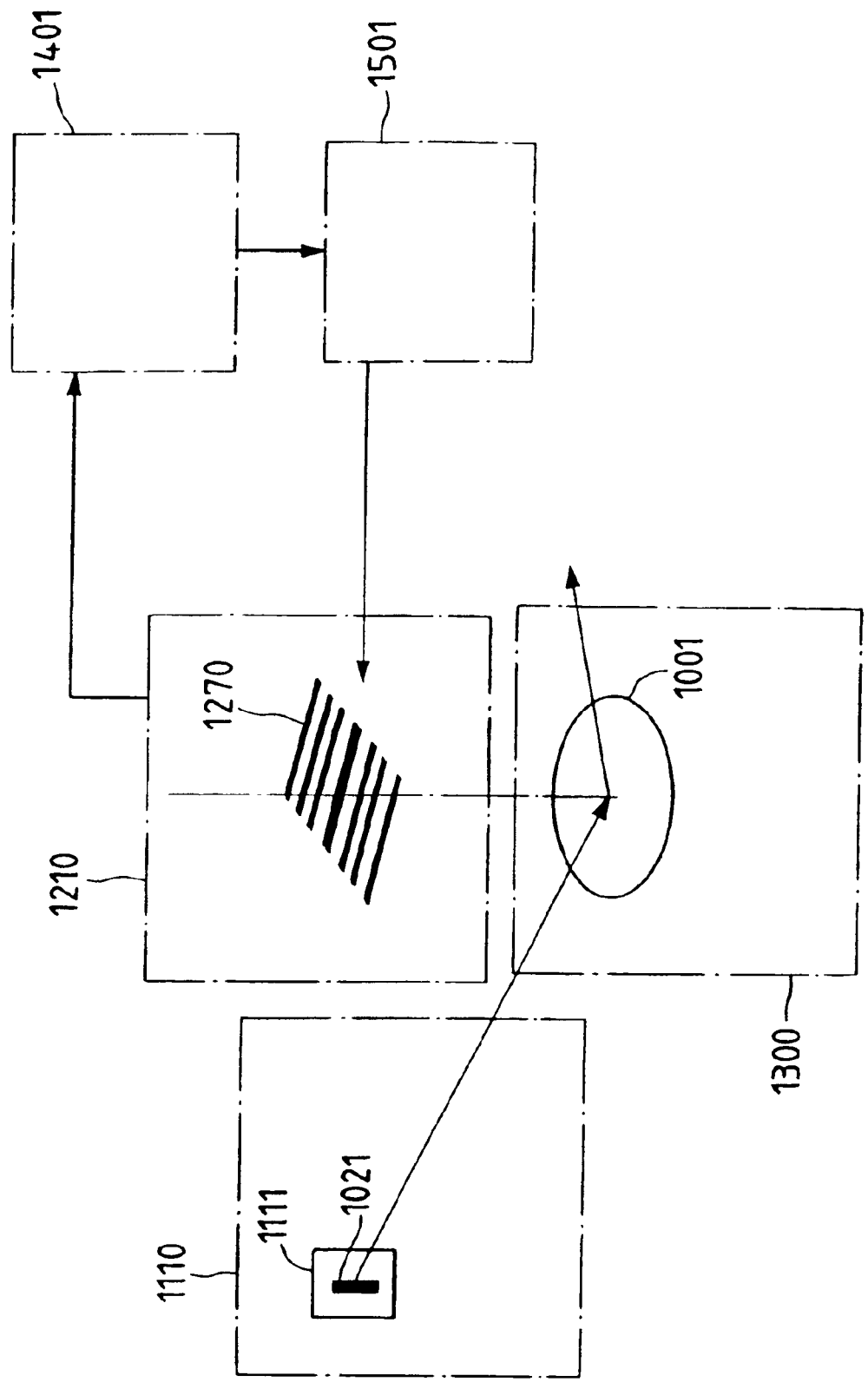
FIG. 19 is a construction diagram showing an embodiment of the present invention using a variable spatial filter.

In the x direction in FIG. 11(*a*), the light emitted from the semiconductor laser 2101 is condensed through lenses 2102 to 2106 and then radiated onto the wafer 111. On the other hand, in the y direction in FIG. 11(*b*), the light front the semiconductor laser 2101 is widened into parallel light rays through lenses 2102 to 2106. According to this method, it is possible to attain a high illuminance of illumination because the light beam in the x direction can be condensed easily. In this method, since the light beam in the x direction is condensed at a certain angle, not parallel light rays, a diffraction pattern in the x direction on the spatial filter surface of the detecting optical system becomes long, but a diffracted light from pattern can be shielded by using such a linear spatial filter as shown in FIG. 19. FIG. 12 is an example of a plan view of patterns on the wafer as viewed on the spatial filter surface of the detecting optical system in the case of using the illuminating optical system illustrated in FIG. 11. The size of one point of a diffraction pattern from patterns on the wafer depends on the numerical aperture of illumination in the x direction and x1=several mm, while in the y direction, y1=several μm, because of parallel light rays. Thus, a sharp light is obtained only in the y direction. In the case where the pitch Py in the y direction is shorter than the pitch Px in the x direction in some particular direction of the wafer, as shown in FIG. 12(a), the light shielding rate of the spatial filter becomes high and the detection output from foreign particles drops. In view of this point, by rotating the wafer 90°, the diffraction patterns from the patterns on the wafer are changed into those shown in FIG. 12(b), in which the pitch in the y direction is the same as the pitch Px in (a) of the same figure and thus it is possible to improve the light shielding performance of the spatial filter. Thus, by presetting the direction of the wafer so that the longer pitch of diffraction patterns is positioned in the y direction, it is made possible to further improve the detection output from foreign particles. Such an optimum direction of the wafer can be inputted as data in advance. Once an optimum direction of the wafer is detected in view of the diffraction pattern direction, and thereafter the portion above the said optimum direction is used.

Figure 13A:
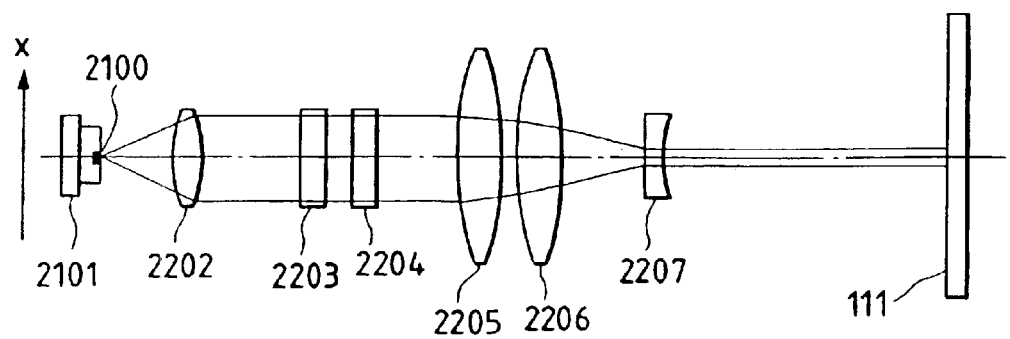
FIGS. 13(a) and 13(b) are side views of a lighting unit according to the present invention.
Figure 13B:
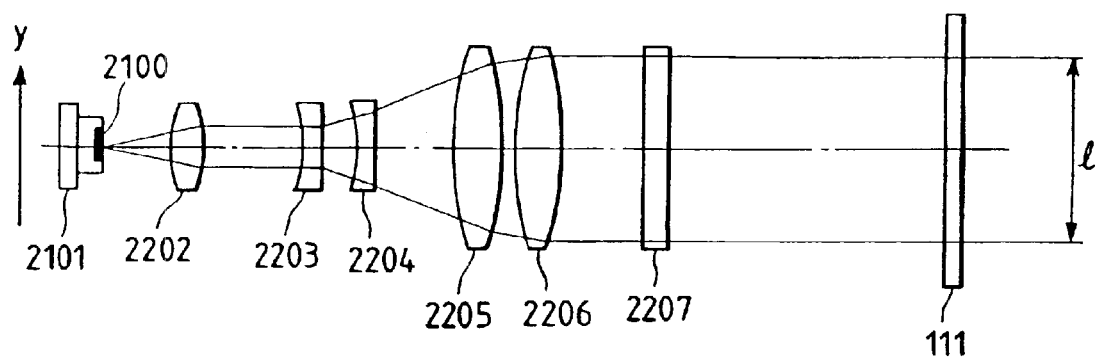

The construction according to the second method referred to above is illustrated in FIG. 13, in which (a) shows the construction as seen in x direction, while (b) shows the construction as seen in y direction. A shorter direction (closer to the spot light source) of a luminous point 2100 of a semiconductor laser 2101 is x direction, while a longer direction of the luminous point 2100 is y direction, provided if the illumination on the wafer is P-polarized light illumination, a λ/2 plate is inserted for S-polarized light illumination.

In the x direction in FIG. 13(a), the light emitted from the semiconductor laser 2101 is condensed into parallel light rays using lenses 2202 to 2207. In the y direction in (b) of the same figure, the light from the semiconductor laser 2101 is widened and radiated onto the wafer 111, using lenses 2202 to 2207, provided parallel rays cannot be obtained because the luminous point 2100 in the x direction is as long as several ten μm. The light from the light source 2100 is focused in the position of a spatial filter 2015 through lenses 2202 to 2207 and a focusing lens 2014. Adjustment is made so that an overall focusing magnification is 1X or so because an optimum value is several ten μm below the light shielding performance of the spatial filter.

Figure 14:
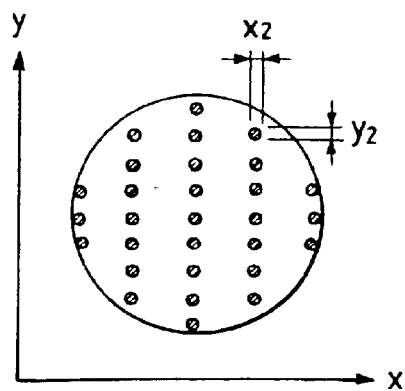
FIG. 14 is a plan view of a diffraction pattern on a spatial filter surface according to the present invention.

FIG. 14 is an example of a plan view of diffraction patterns from patterns on the wafer as viewed on the spatial filter surface of the detecting optical system in the case of using the illuminating optical system shown in FIG. 13. The size of one point of a diffraction pattern from patterns on the wafer is x2=100 μm or so in the x direction because of a collimated beam, while in the y direction it is y2=several ten μm because of being proportional to the magnitude of the illuminating light source. Thus, a relatively sharp light is obtained in both x and y directions independently of the direction of the wafer, and it is possible to improve the light shielding performance of the spatial filter.

Another example of a foreign particle detecting optical system using the polarized light detection method in the small-sized foreign particle monitor according to the present invention will be described below with reference to FIGS. 15 and 16.

The polarized light detection method permits discrimination and detection of foreign particles from all the patterns on the whole wafer surface without making limitation to memory patterns.

Figure 15:
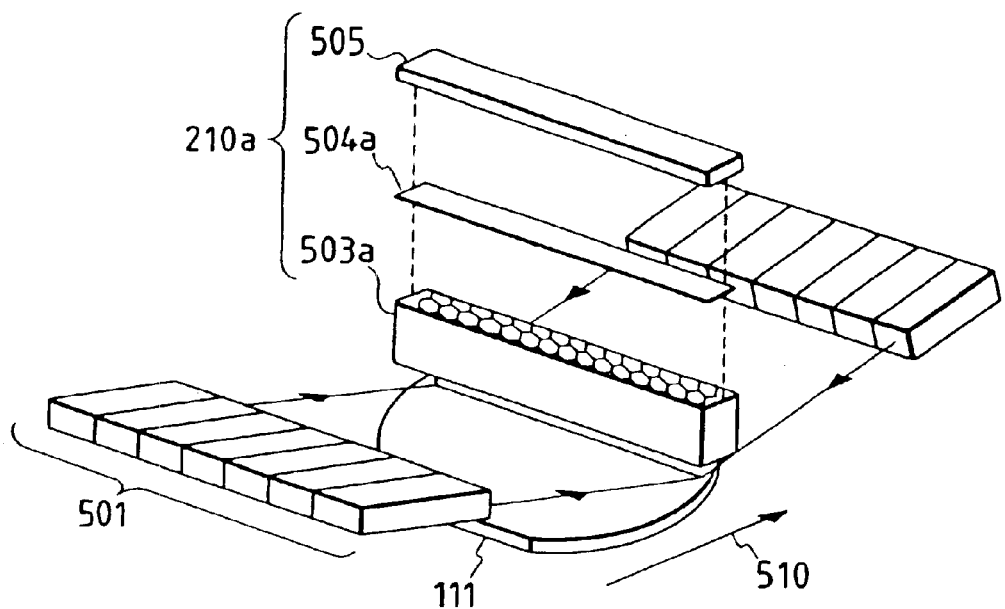
FIG. 15 is a construction diagram of a foreign particle detecting optical system using polarized light for detection according to the present invention.

FIG. 15 is a construction diagram of a foreign particle detecting optical system using a lens array of a refractive index varying type as a detection lens, which optical system comprises an oblique illuminating optical system 501 and a detecting optical system 210a. As shown in the same figure, the oblique illuminating optical system 501 is constituted by at least one illumination array, while the detecting optical system 210a comprises a lens array 503a of a refractive index varying type as a detection lens, a polarizing plate 504a as a polarizing element, and a detector 505 disposed in a focusing position of the refractive index varying type lens array 503a. A linear illumination for illuminating the entire width of the wafer is obtained by the illumination array to make detection over the whole wafer width. Therefore, the whole surface of the wafer 111 can be inspected by a uniaxial scan 510 on the wafer. The illumination array 501 is set at an illumination angle of several degrees higher with respect to the horizontal direction, and the upper surface of the wafer 111 is illuminated with a linearly polarized light (S-polarized light) so that a magnetic field vector is perpendicular to the incidence surface in the illumination. Scattered light from patterns and foreign particles on the wafer 111 passes through the lens array of a refractive index varying type, then only P-polarized light (a linearly polarized light of a component wherein a magnetic field vector is parallel to the incidence surface in the illumination) is allowed to pass, through the polarizing plate 504a, thereby diminishing the scattered light from patterns, while emphasizing the scattered light from foreign particles, for detection in the detector 505.

Figure 16:
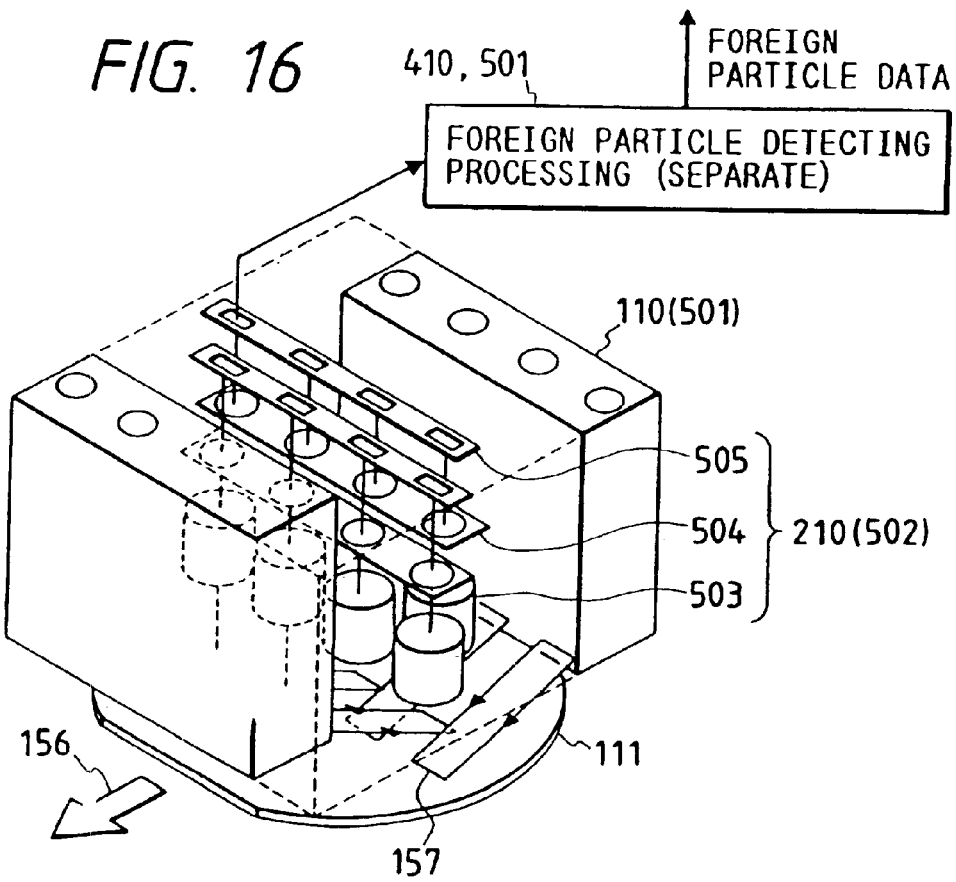
FIG. 16 is a diagram showing an apparatus construction of a foreign particle detecting optical system using polarized light for detection according to the present invention.

FIG. 16 is a construction diagram of a foreign particle detecting optical system using ordinary lenses as detection lenses. The foreign particle detecting optical system is of a construction wherein the whole surface of a product wafer 111 can be inspected by a uniaxial scan 510 on the wafer. To this end, the optical system is divided into an illuminating optical system 110 (501) and a detecting optical system 210 (502), which systems each have a unit construction. Description will now be provided about the case where the wafer to be inspected to 200 mm in diameter. For example, to inspect the entire width of the wafer 111, an illumination and detection area 157 of one unit should be 25 mm. Therefore, when the wafer to be inspected is 150 mm in diameter, it suffices to use six units out of the eight units. The detecting optical system 210 of one unit comprises a detection lens 503, a polarizing plate 504a and a linear sensor 505 as a detector. In the case where an external size of the detection lens 503 is larger than the detection width, the entire width of the wafer 111 can be covered by such as zig-zag arrangement as shown in FIG. 16. On the other hand, in the case of an external size of the detection lens 503 smaller than the detection width, or when a limited portion on the wafer is to be inspected, that is, in the case of a partial inspection, there may be adopted a linear arrangement. Illumination by the illumination unit 110 (501) is made at an angle of several degrees higher with respect to the horizontal direction, and the upper surface of the wafer 111 is illuminated with a linearly polarized light (S-polarized light) so that a magnetic field vector is perpendicular to the incidence surface in the illumination. Scattered light from patterns and foreign particles on the wafer 111 passes through the detection lens 503, then only P-polarized light (a linearly polarized light of a component in which a magnetic field vector is parallel to the incidence surface in the illumination) is allowed to pass through the polarizing plate 504a, thereby diminishing the scattered light from patterns, while emphasizing the scattered light from foreign particles, for detection in the linear sensor 505. A detected signal from the linear sensor 505 is processed in a foreign particle detecting processing (separate) 410, 501 and is then outputted as foreign particle data.

Figure 17:
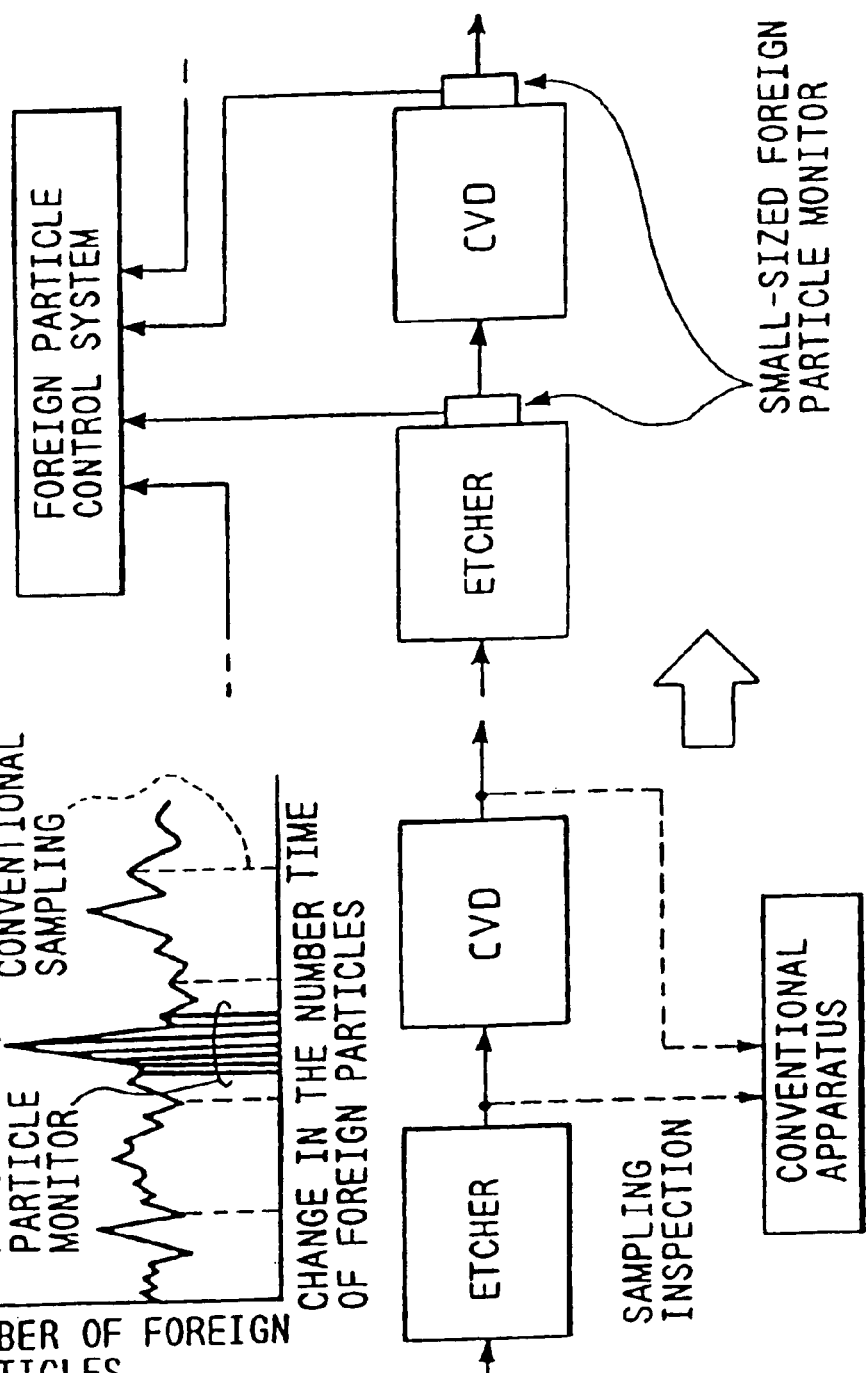
FIGS. 17(a)–17(c) are diagrams showing in what position the present invention lies and also showing functions.

FIG. 17 shows in what position the present invention lies, as well as functions. One of main mass production starting operations for LSI is an operation of clearing up the cause of generation of foreign particles and taking a countermeasure. In this connection, detecting foreign particles and analyzing the kind of element, etc. is an important clue to clear up the cause of their generation. On the other hand, in the mass production line, it is necessary to detect the generation of foreign particles and take a countermeasure as soon as possible. As time elapses from the generation of foreign particles up to the detection thereof, the number of defects generated increases and hence the yield lowers. Therefore, in order to maintain a high yield, it is absolutely necessary to shorten the time elapsed from the generation of foreign particles until the detection thereof. As a result of a strict experiment for detecting the number of foreign particles on a wafer, it turned out the number of foreign particles increased or decreased not gradually but suddenly. FIG. 17(a) shows how the number of foreign particles on a product wafer generated in a processing apparatus such as a CVD apparatus changes with the lapse of time. FIG. 17(b) shows a conventional apparatus. The conventional apparatus is a stand-alone type and a wafer which has been processed in a mass production line taken out of the mass production line and is carried to the installed place of the inspection apparatus and inspected there for particles, that is, subjected to a sampling inspection off line. Thus, it takes time for conveyance of the wafer and for the inspection of foreign particles. Consequently, the inspection frequency or sampling is one lot, or several lots, or one sheet a day, as shown in (a) of the same figure, and a limit has been encountered in the number of sheets capable of being inspected. In such a way of sampling, a sudden increase in the number of foreign particles may be overlooked, or detection may be made in a certain time elapsed after the increase, thus resulting in the generation of a considerable number of defects (lots of defects). In such a sampling method, it cannot be said that the generation of foreign particles is sensed sufficiently quickly. In view of these points, as shown in FIG. 17(c), a small-sized foreign particle monitor 101 as a smaller version of the foreign particle monitoring apparatus is disposed at inlets or outlets of processing apparatus 103, 104, or in a conveyance system located between the processing apparatus so as to detect the foreign particles of a substrate in the fabrication line, i.e. on lines, and foreign particle data from the monitor 101 are taken into a foreign particle control system 128, whereby the control of foreign particles can be done in sheet form. Thus, by using the small-sized foreign particle monitor 101, it is made possible to shorten the sampling time in the monitor, perform a real-time sampling in sheet form and obtain a maximum effect of the foreign particle inspection.

The following five items are mentioned as functions of such foreign particle monitor. (1) The size is small to the extent of permitting the mounting of the monitor to the conveyance system of the processing apparatus; (2) it is possible to conduct a high-speed inspection in sheet form of wafer; (3) the price is low to an extent capable of being an option in each processing apparatus so as to permit a foreign particle control for each processing apparatus; further, because of a monitor, (4) it is easy to make setting, and (5) a maintenance-free construction can be provided.

Figure 18:
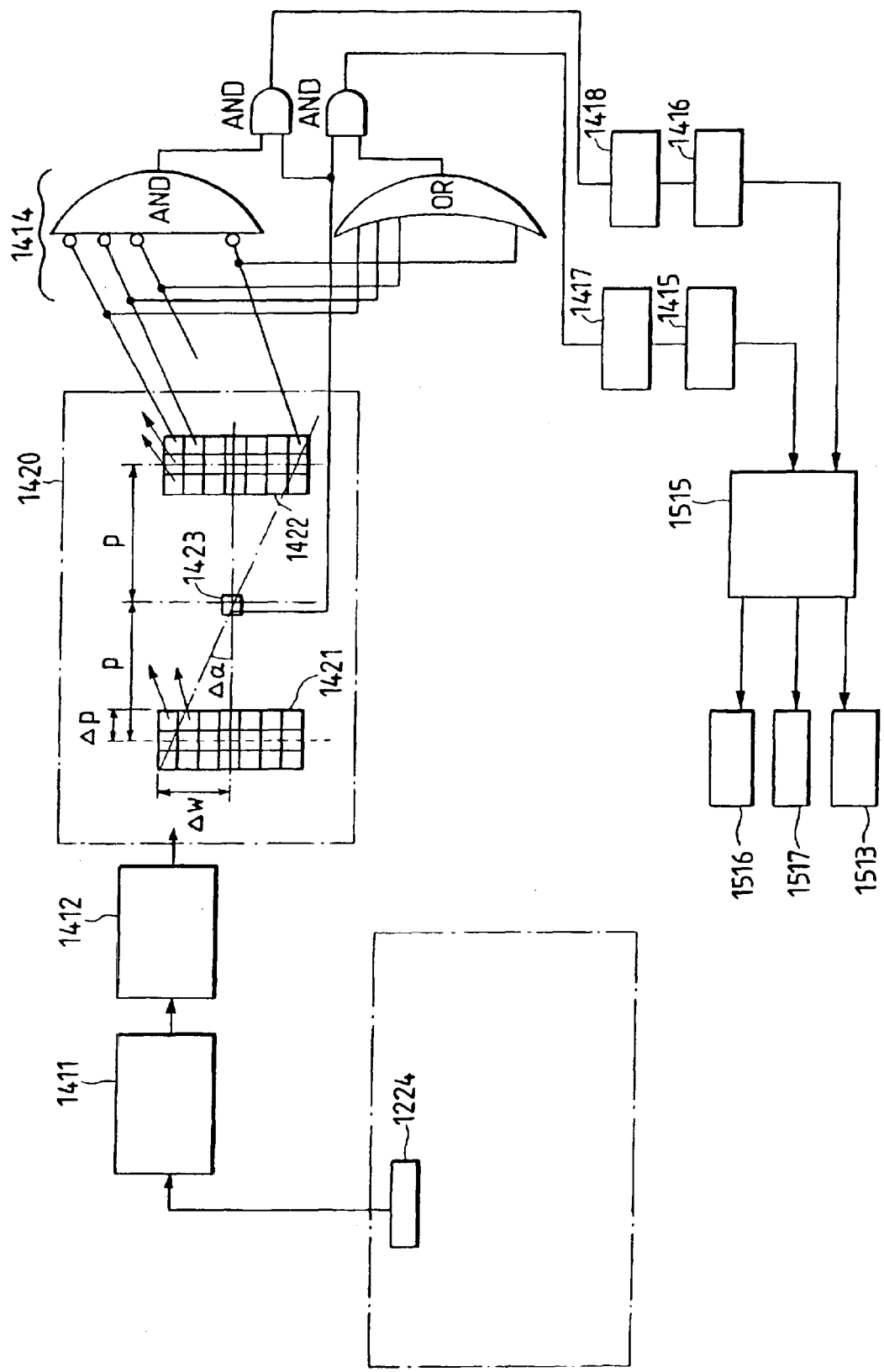
FIG. 18 is a block diagram showing an example of a signal processing system according to the present invention.

A further embodiment will now be described with reference to FIG. 18. FIG. 18 illustrates a foreign particle pattern judging system which fulfils both the function of a signal processing system 1410 and a data processing system 1501. In the data processing system 1501, non-repetitive patterns around chips in a wafer are discriminated and removed by utilizing the repetitiveness of the chips. This function is attained also by the circuitry shown in FIG. 18.

This embodiment involves an image take-out circuit 1420 as a substitute for a two-dimensional image take-out circuit 1413. The image take-out circuit 1420 comprises take-out portions 1421, 1422 and a to-be-judged portion 1423. The take-out portions 1421 and 1422 are disposed relative to the to-be-judged portion 1423 so that an image in a position spaced by a chip pitch p on a sample can be taken out. Since the wafer has a rotational error $\Delta\alpha$ and a chip spacing error $\Delta p$ based on errors such as chip transfer error, focusing magnification error, binary coding error, etc., the image take-out portions 1421 and 1422 have a margin of approximately $\pm\Delta\alpha$ and $\alpha\Delta p$ for the to-be-judged portion 1423. These values can be set experimentally or on the basis of an apparatus fabrication accuracy, but in this embodiment, the picture element size is set at 7 $\mu$m, $\Delta p$ is set at 1.5 picture elements and $\Delta\alpha$ at 0.5°, pitch is assumed to be about 10 mm, and $\Delta w$ ($=\Delta\alpha\cdot p$) is set at 12.5 picture elements. A signal taken out from the take-out circuit 1420 is processed by the signal processing system shown in FIG. 18. In the two-dimensional take-out circuit, the surrounding portion of a taken-out square is ANDed in □ shape in accordance with Equation 1, while the whole area of the take-out portions 1421 and 1422 is ANDed. More specifically, in the two-dimensional take-out circuit, the surrounding portion of the taken-out square is assumed to be P(i, j), while in the take-out portions 1421 and 1422, the whole area taken out is assumed to be P(i, j). With difference found only in the shape of P(i, j), the judgment of pattern is expressed by Equation 2 and that of foreign particle by Equation 3.

In this construction, an FFT circuit 1511 and a repetitive portion eliminating circuit 1512 can be omitted.

Examples of spatial filters will now be described with reference to FIGS. 19 to 22. A spatial filter may be constituted by using a liquid crystal display, but in the case of a liquid crystal display, there can be used only light in a specific polarizing direction, and since the attenuation factor of light is small, it is impossible to sufficiently shield a diffracted light from pattern. In view of these problems, it is better to constitute the spatial filter mechanically using a metallic plate or the like.

Figure 20:
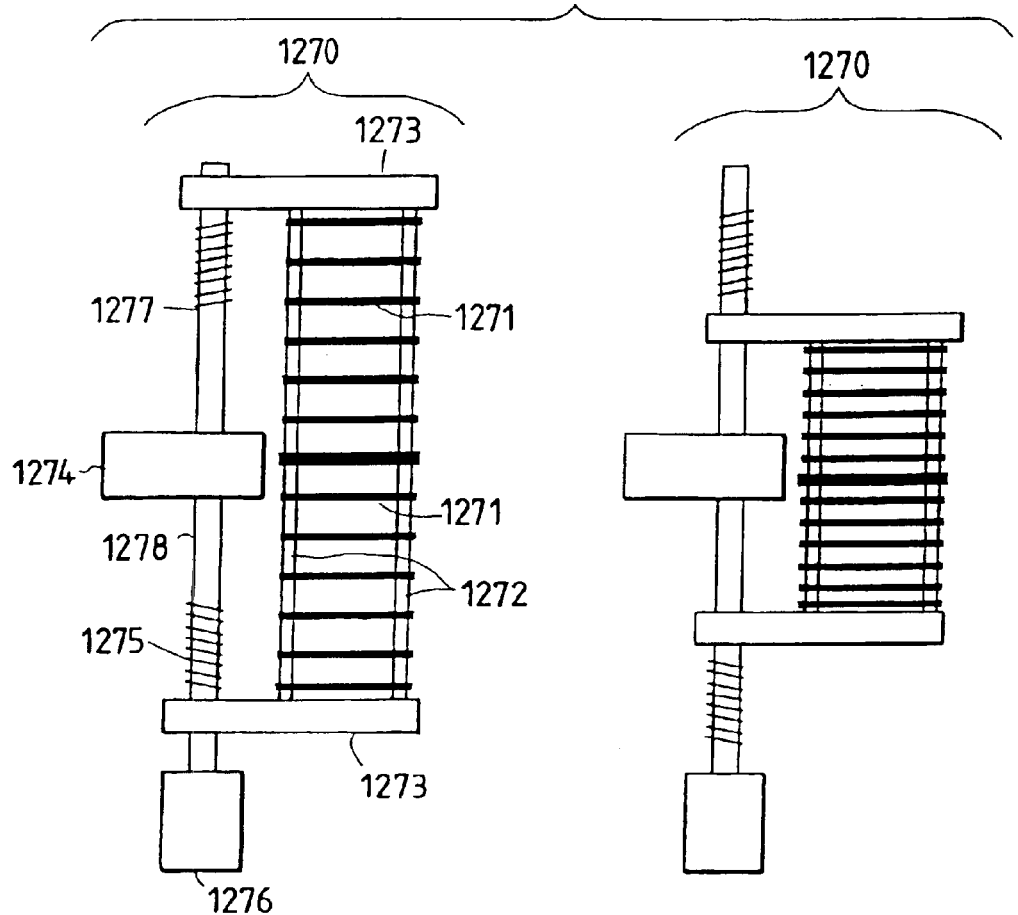
FIG. 20 is a concrete construction diagram of the variable spatial filter shown in FIG. 19.
Figure 21:
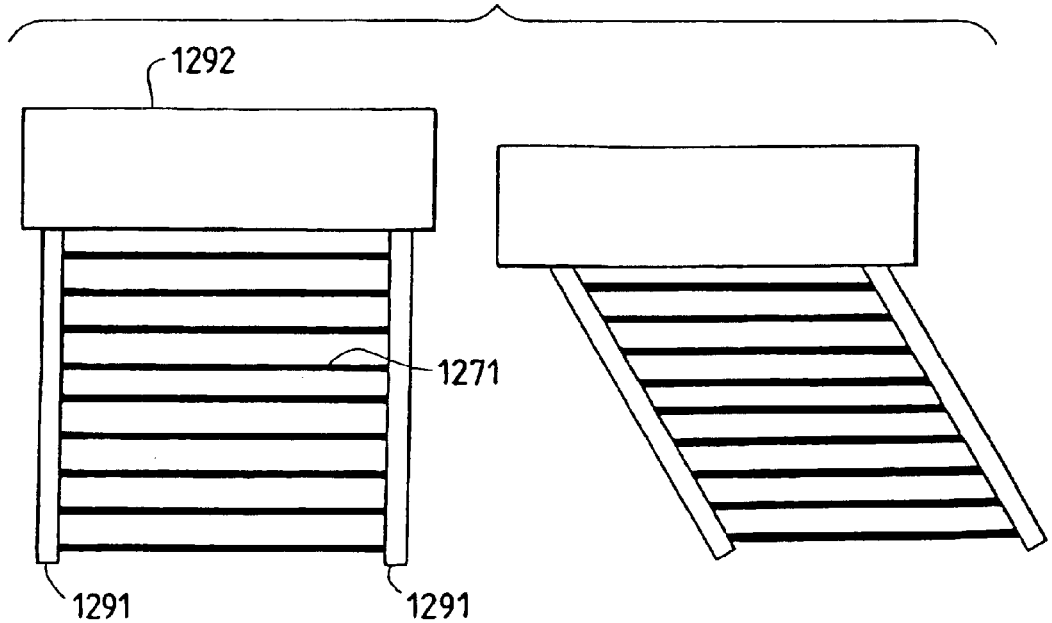
FIG. 21 is another concrete construction diagram of the variable spatial filter shown in FIG. 19.

As illustrated in FIGS. 20 and 21, the spatial filter is constituted by a gathering of linear patterns. (of course, it is desirable that the spatial filter be a gathering of larger spots to shield such a gathering of spots as shown in FIG. 12(a), but even when it is a gathering of straight lines like that shown in this example, the function required for the spatial filter is fully exhibited in addition to its merit of being simple in construction.) These linear patterns' pitch and phase may be matched together. FIG. 19 shows an example of a pitch variable spatial filter 1270 using a metallic plate.

The illustrated embodiment comprises an illuminating optical system 1110, a detecting optical system 1210, a stage system 1300, a signal processing system 1401 and a data processing system 1501. This is the same as in the embodiment shown in FIG. 23.

In the case where a light emitting port 1021 of a semiconductor laser 1111 is disposed so as to be long in the vertical direction, if the illumination system shown in FIG. 11 is used, the rectilinear direction of the spatial filter becomes parallel to the incidence surface of the illuminating light beam, as illustrated in FIG. 19. In this case, all that is required for positioning the spatial filter is merely matching the pitch of linear patterns with a central linear pattern as a reference. To this end, a pitch varying mechanism for the spatial filter can be constituted easily.

The pitch variable spatial filter 1270 shown in FIG. 19 is constructed as in FIG. 20. As illustrated therein, the spatial filter 1270 comprises a plurality of linear patterns 1271 formed of a material high in light transmitting rate such as, for example, a metal, a metal oxide or a plastic material, spring-like support members 1272, support members 1273, a fixing means 1274, a screw 1275 and a screw driving means 1276. The screw 1275 has right-hand threads formed in its portion 1277 and left-hand threads formed in its portion 1278. The pitch between adjacent linear patterns 1271 can be changed-by rotating the screw 1275 through the screw driving means 1276. In the operation of the screw driving means 1276, the pitch between adjacent linear patterns 1271 is controlled in accordance with a calculated value on the basis of a cell pitch d detected simultaneously with a chip pitch p at the time of introduction of the wafer. The spring-like support members 1272 may be formed of rubber.

It is difficult to change the pitch of the spatial filter 1270 in a wide dynamic range. This is because, for example in the case of making the pitch into one tenth, it is necessary that the screw 1275 should have a length ten times as large as the length required as the spatial filter. In view of this point, plural spatial filters 1270 may be disposed one upon another. In this case, the pitch can be changed small by operating the foregoing pitch varying mechanism in the stacked state of the filters, and the pitch can be changed large by shifting the spatial filters from each other. Of course, both such operations may be done at a time.

It is desirable that a central linear pattern 1279 of the spatial filter 1270 be formed thicker than the other linear patterns. This is because a diffracted light at the central portion, namely, a zero-order diffracted light is high in intensity and has a wide intensity distribution, so a wide linear pattern is required for shielding the diffracted light to a satisfactory extent.

Although one example of a drive mechanism is referred to herein, this constitutes no limitation in working the present invention. There may be adopted another drive mechanism if only it has a construction capable of driving the linear patterns 1271 high in shielding performance. As a concrete construction, there may be used such a construction as shown in FIG. 21. In the construction illustrated therein, linear patterns 1271 are supported by links 1291, and the links 1291 are varied their inclination by means of a link driving mechanism 1292 to thereby change the pitch.

The direction of the wafer may be set so that the spatial filter pitch can be made large, that is, in a small direction of the pattern pitch d on the wafer.

Figure 22:
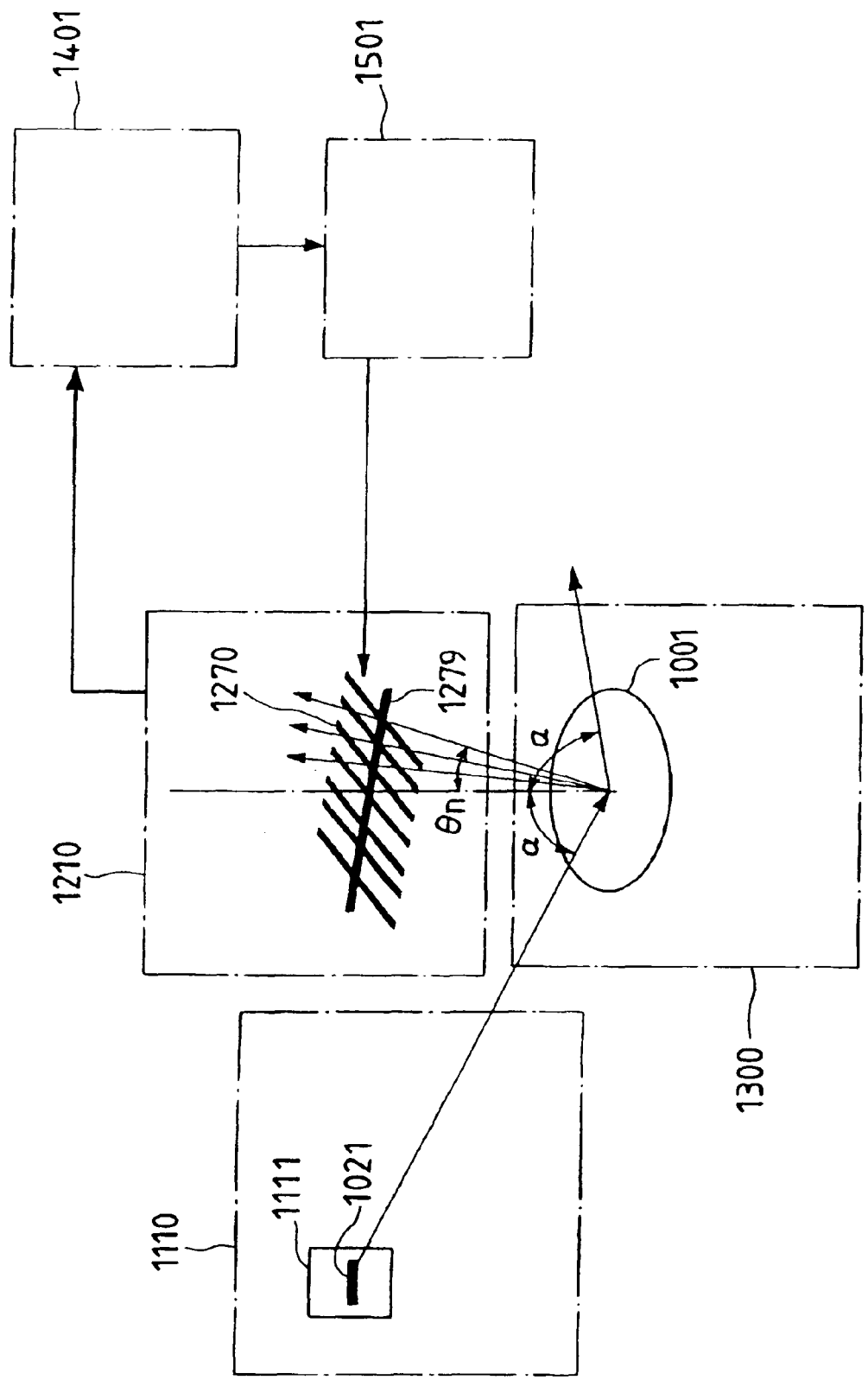
FIG. 22 is a construction diagram showing another embodiment of the present invention using a variable spatial filter.
Figure 23:
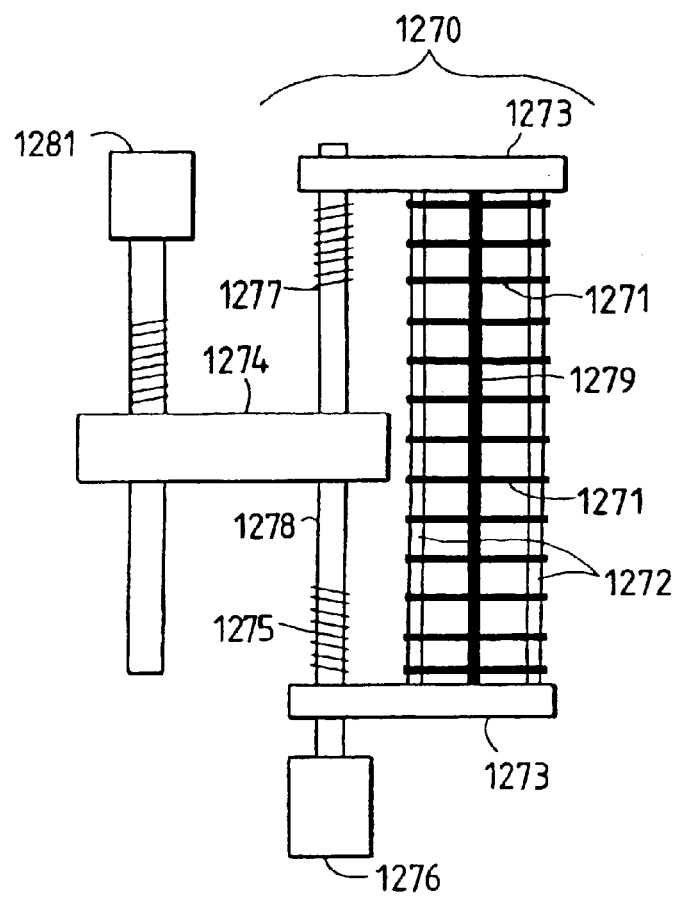
FIG. 23 is a concrete construction diagram of the variable spatial filter shown in FIG. 22.

As shown in FIGS. 22 and 23, in the case of using the optical system illustrated in FIG. 12 as the illuminating optical system 1110, it is necessary that a rather thick, linear spatial filter 1279 be disposed centrally in parallel with the incidence surface in illumination and linear patterns be disposed perpendicularly thereto. In this case, it is necessary to adjust pitch and phase for positioning of the spatial filter. If the incidence angle in illumination is a, an exit angle of a linear diffraction pattern is θn, the wavelength of illuminating light is λ and a basic pattern pitch on the wafer is d, the following equation is established:

$$\sin(\alpha-\theta n)=n\cdot\lambda/d \qquad (9)$$

Therefore, it is necessary to establish a pitch varying mechanism which satisfies Equation 9. More specifically, the pitch variable space filter 1270 is disposed in a 90° turned direction, and in addition to the adjustment of the pitch, there is made adjustment of the phase by moving the whole of the pitch variable spatial filter 1270 in a direction perpendicular to the linear patterns 1271. This phase adjustment is performed by a phase adjusting means 1281. In this construction, it is desirable that a light shielding plate which is rather thick, about one to three times as thick as a linear pattern, be disposed in a central position of the spatial filter in parallel with the incidence surface in illumination.

The thickness of a linear pattern is preferably determined experimentally, but in point of design, it should be set at a value 10% to 20% larger than the size of image on the spatial filter of the light from the light source 1111 in the illumination system. But when the accuracy of the spatial filter adjusting mechanism is considered, it is necessary to provide a still larger margin.

Figure 24:
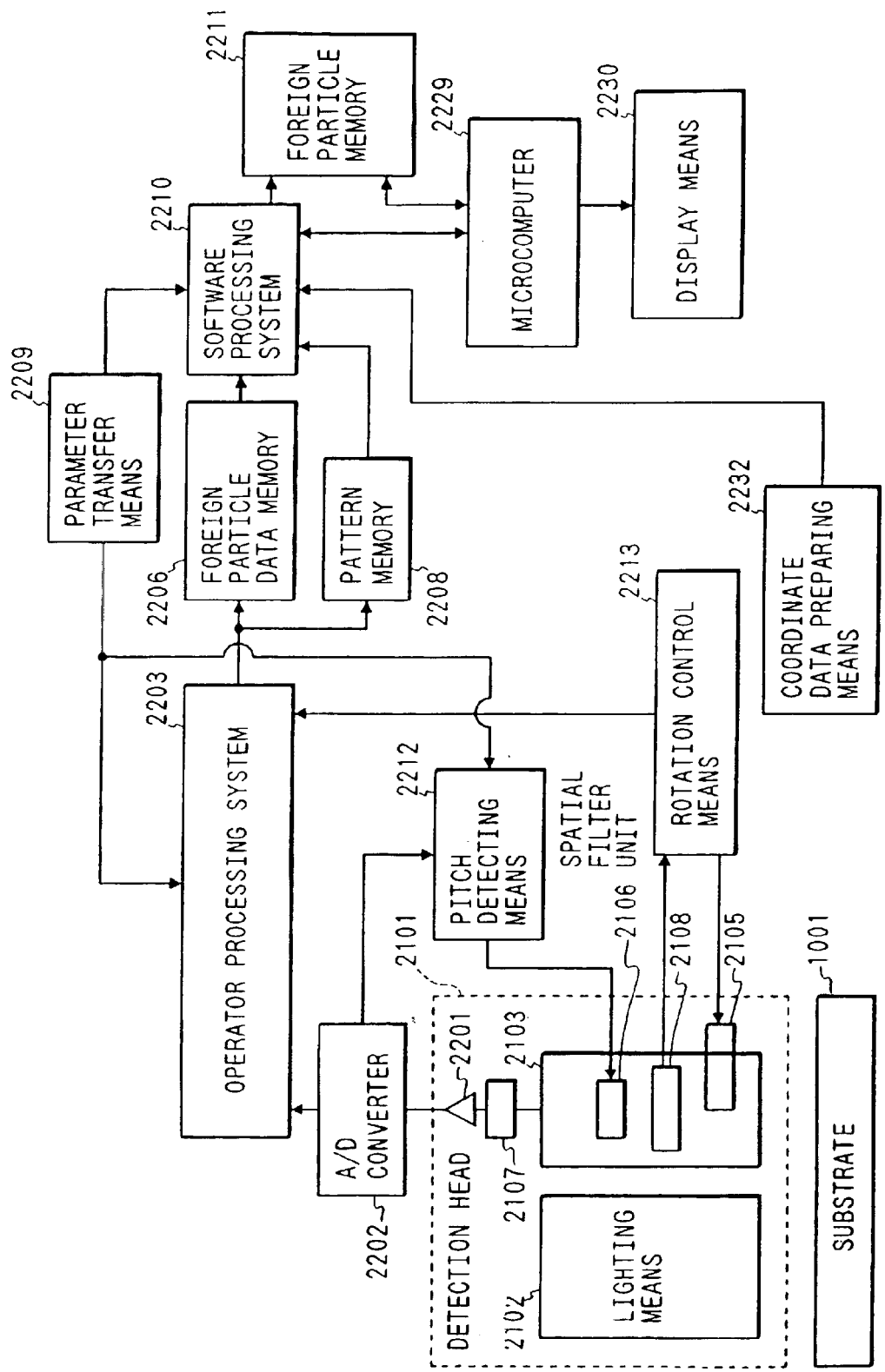
FIG. 24 is a block diagram of an apparatus embodying the present invention.

Although the construction of FIG. 24 is depicted in a 6-channel parallel fashion, no limitation is made to such 6-channel structure. This point is determined according to specifications such as wafer size and inspection time.

Although description has been made above about the spatial filter mechanism in the case of constituting an illuminating optical system using the optical system shown in FIGS. 11 and 12, even in the case of using another illumination system not described here, the light shielding rate can be improved by using a mechanical spatial filter, so it is possible to shield a diffracted light from patterns efficiently and hence possible to improve the foreign particle detecting sensitivity.

In the case where the spatial filter pitch and width are to be made still finer, the mechanical construction referred to herein will be insufficient in point of accuracy. In this case, a variable spatial filter can be fabricated using a method introduced as "Micromechanism."

The above construction is advantageous in that the trouble of replacing the spatial filter for each product can be omitted because the spatial filter pitch can be changed automatically upon receipt of data such as chip pitch and cell pitch of product.

Alternatively, a spatial filter may be fabricated for each product and replaced automatically. In this method, three filters are disposed on one substrate and replaced.

According to the present invention, by introducing the foreign particle inspecting apparatus into a line, it is made possible to inspect all of the wafers passing along the line and hence possible to make a real-time detection of an increase in the number of foreign particles. Consequently, the occurrence of a large quantity of defective products caused by the generation of foreign particles can be prevented and it is thereby possible to improve the yield.

According to the present invention, moreover, by monitoring foreign particles using only a monitoring apparatus of a simple structure in a mass production line of a semiconductor manufacturing process, the production line can be reduced in weight to permit reduction of the manufacturing cost. Further, since the monitoring apparatus permits a real-time foreign particle inspection, it is possible to minimize the incorporation of defects and there can be made a great contribution to the improvement of product yield.

Another concrete example of constructor of an on-line monitor according to the present invention will be described below with reference to FIGS. 24 to 30.

As shown in FIG. 24, this embodiment comprises detection head 2101, a pitch detecting means 2212, an operator processing system 2203, a foreign particle data memory 2206, a pattern memory 2208, a software processing system 2210, a parameter transfer means 2209, a foreign particle memory 2211, a coordinate data preparing means 2232, a microcomputer 2229 and a display means 2230, the detection head 2101 comprising a lighting means, a detecting optical system 2103, a rotation matching mechanism 2105, a spatial filter unit 2106, a detector 2107, a rotation detecting means 2108, an operational amplifier 2201 and an A/D converter 2202.

As shown in FIG. 25, the lighting means 2102 comprises a semiconductor laser 2112, collimator lenses 2113, concave lenses 2114, a beam expander consisting of receiver lenses 2115, a cylindrical lens 2116 and a mirror 2118. The detecting optical system comprises Fourier transform lenses 2110, a spatial filter unit 2106, a rotation detecting means 2108 and Fourier transform lenses 2111.

Figure 26:
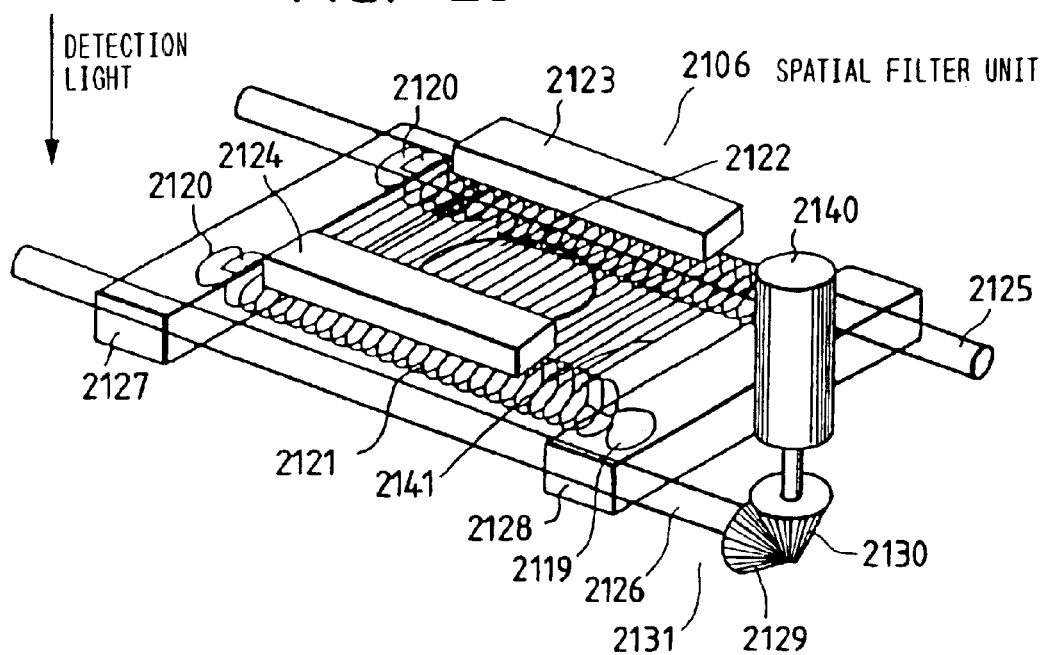
FIG. 26 is a perspective view of a spatial filter mechanism illustrated in FIG. 24.

Further, as shown in FIG. 26, the spatial filter unit 2106 comprises coil springs 2121, 2122, plural linear spatial filters 2141, coil spring supports 2119, 2120, a guide 2125, 2126, a screw 2126 having a right-hand threaded portion 2127 and a left-hand threaded portion 2128, worm gears 2129, 2130, and a motor 2140. The spatial filter unit 2106 is provided with rotation detectors 2123 and 2124.

Figure 27:
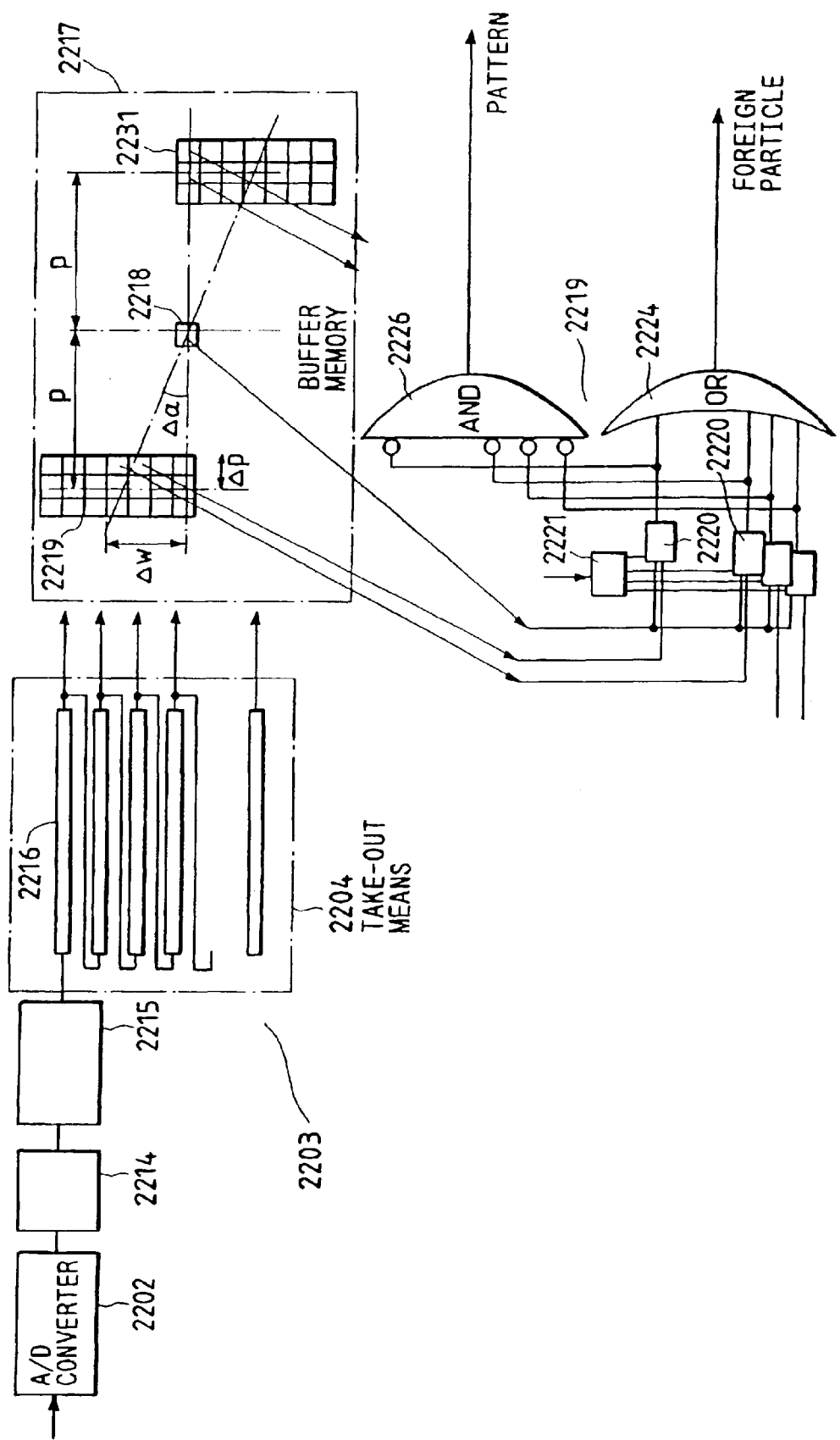
FIG. 27 is a construction diagram showing an operator processing section illustrated in FIG. 24.

As shown in FIG. 27, the operator processing system 2203 comprises a four-picture element adding means 2214, an octal coding means 2215, a take-out means 2204 consisting of plural line memories 2216, a buffer memory 2217, a decision picture element take-out means 2218, operator take-out means 2219, 2231, a comparator group consisting of plural foreign particle comparison circuits 2220, a threshold setting circuit 2221, an OR circuit 2224 and an AND circuit 2226.

Figure 28:
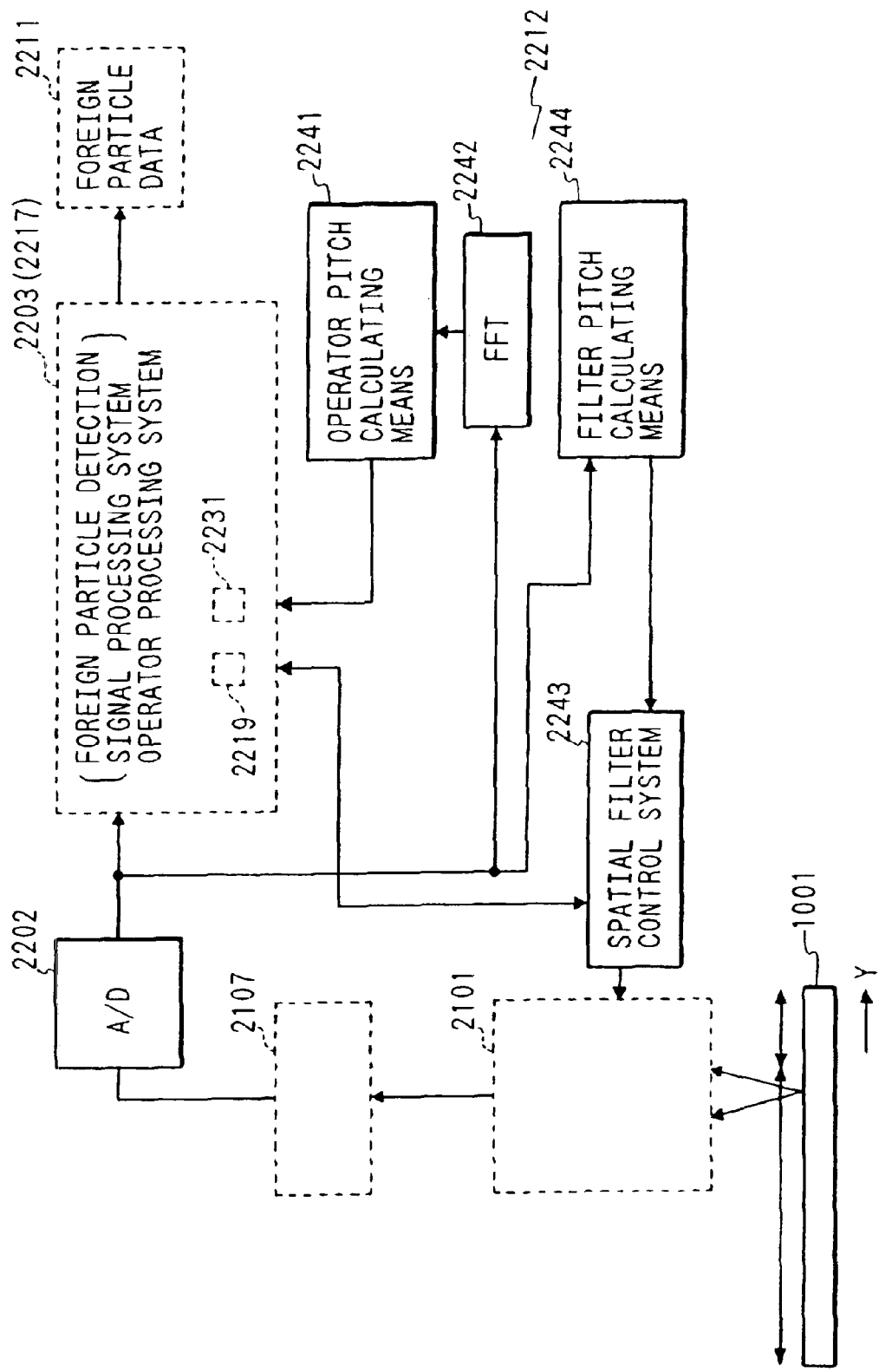
FIG. 28 is a block diagram showing a parameter detecting system illustrated in FIG. 24.

Further, as shown in FIG. 28, the pitch detecting means 2212 comprises an FFT circuit 2242, an operator pitch calculating means 2241, a filter pitch calculating means 2244 and a spatial filter control system 2243.

Figure 40:
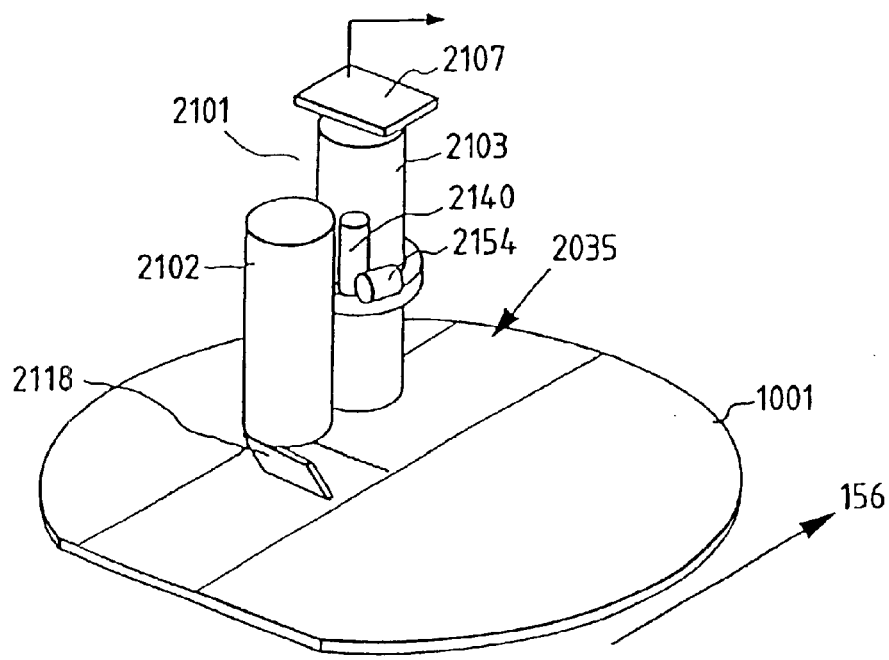
FIG. 40 is a perspective view showing a method of utilizing a detection head according to the present invention.

The rotation matching means 2105 as shown in FIG. 24 comprises a rotation guide, a rotation bar, a spring, a piezoelectric element 2154 as shown in FIG. 40, a piezoelectric element controller and a base.

(Relation)

The substrate 1001 is illuminated by the lighting means 2102 and scattered or diffracted light from foreign particles, defects or patterns on the substrate surface is taken in and subjected to an optical filtering processing in the spatial filter unit 2106, then detected by the detector 2107 in the detecting optical system 2103. The detected signal is amplified into a signal of large impedance difficult to incorporate a noise component therein by means of the operational amplifier 2201 in the detection head 2101, which signal is then converted into a digital signal by the A/D converter 2202. This digital signal is transferred to the operator processing system 2203. A rotating direction of the substrate 1001 is detected by the rotation detecting means 2108 and pre-matching of rotational direction is made for the substrate 1001 by the rotation matching mechanism 2105 which is controlled by the rotation control means 2213. Since the detecting optical system 2103 has a sufficiently large focal depth, an automatic focusing operation is basically not necessary if only the conveyance of the substrate 1001 is performed with a mechanical accuracy by means of a conveyance system (not shown). More particularly, when the numerical aperture is 0.08, using a wavelength of about 800 nm, the focal depth is about ±100 microns. Of course, even if there is used an automatic focusing mechanism, there will arise no problem.

In the pitch detecting means 2212, a pattern repetition pitch and a chip pitch on the substrate 1001 are measured from a detected signal. In the operator processing system 2203, pattern information is eliminated by utilizing the repetitiveness of chip pitch on the basis of data such as chip repetition pitch which have been transferred by the parameter transfer means 2209. The result is stored in the foreign particle data memory 2206, large foreign particle data memory 2207 and pattern memory 2208. Further, pattern information such as a test element group not having repetitiveness between chips is eliminated on the basis of information such as repetitive chips of a position coordinate chip in a test element group which has been transferred by the parameter transfer means 2209, and is stored in the foreign particle memory 2211. Coordinate data are prepared by a coordinate data 2232 and stored if necessary simultaneously with foreign particle information. These processings are controlled by the microcomputer 2229 and displaced by the display means 2230.

In the lighting means 2102, as shown in FIG. 25, the light from the semiconductor laser 2112 is collimated as plane wave by means of collimator lenses 2113, concave lenses 2114 and receiver lenses 2115, then passes through the cylindrical lens 2116 and mirror 2118 and illuminates the upper surface of the substrate 1001. In this illumination, as shown in the same figure, the light collimated only in x direction by the cylindrical lens 2116, while in the y direction it is condensed on the substrate. In the detecting optical system 2103, the light beam which has been subjected to Fourier transform in the Fourier transform lens 2110 is then subjected to an optical filtering processing in the spatial filter unit 2106, and an image on the substrate is focused on the detector 2107 by means of the Fourier transform lens 2111.

In the spatial filter unit 2106, as shown in FIG. 26, the pitch between linear spatial filters 2141 of black color extending between the coils of the coil springs 2121 and 2122 is changed by the coil spring supports 2119 and 2120 which move with rotation of the screw 2126 having right- and left-hand threaded portions 2127, 2128 while being guided by the guide 2125. Power is fed by the motor 2140 through the worm gears 2129 and 2130.

An inclination in the rotating direction of the substrate 1 relative to the detection head 2101 is measured by the rotation detectors 2123 and 2124 which are mounted on the spatial filter unit 2106. For ease viewing, this FIG. 26 is drawn so that detection light is incident from an upward direction.

In the operator processing system 2203, shown in FIG. 27, picture elements 2×2 around a detected signal are added and averaged by the four-picture element adding means 2214. This processing aims at stable detection by averaging, but since the detection performance (detection sensitivity) itself is somewhat inferior, so there is provided a by-pass means to permit by-passing where required. The thus-added signal is octal-coded by the octal coding means 2215 for log scaling and is then stored in the buffer memory 2217 as a two-dimensional image data through the take-out means 2204 which comprises plural line memories 2216. Thereafter, a necessary data are taken out from among such two-dimensional image data by the decision picture element take-out means 2218 and operator take-out means 2219, 2231, and are sent to the comparator circuit 2219. The detector 2107 employs a one-dimensional linear sensor so as to permit a high-speed detection by high-speed stage scan. It is the line memories 2216 and buffer memory 2217 that convert the data from the detector 2107 into a two-dimensional image. Every time a signal is provided as one picture element from the detector 2107, the whole image shifts by one picture element in x direction. This is a so-called pipeline processing. A foreign particle signal is extracted in accordance with a later-described logic through a comparator group consisting of plural foreign particle comparison circuits 2220, threshold setting circuit 2221, OR circuit 2224 and AND circuit 2226.

In the pitch detecting means 2212 shown in FIG. 28, a Fourier transform processing for detected image is performed by the FFT circuit 2242, and on the basis of the result obtained, an operator pitch is calculated by the operator pitch calculating means 2241 and a spatial filter pitch calculated by the filter pitch calculating means 2244, then these calculated values are transmitted to the spatial filter control system 2243 and operator take-out means 2219, 2231.

(Principle)

The following description is now provided about the principle of the PRES (Parameter Reduction Spatial) filter of the present invention.

Figure 29B:
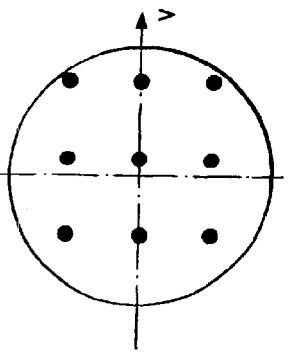
FIGS. 29(a)–29(c) are construction diagrams showing a conventional method.

Heretofore there has been developed a technique of detecting foreign particles or defects having non-repetitiveness by using the repetitiveness of pattern on the wafer surface. However, even in the case pf patterns having repetitiveness, diffraction patterns are different in shape depending on the period of repetition and the shape of basic pattern. Therefore, it has been necessary to change the shape of spatial filter as a light shielding plate in conformity with the shape of repetitive patterns concerned. As such, a spatial filter changing method there has been proposed a method using a photographic plate, which method, however, has required much time or a large-scale equipment for preparing spatial filters according to repetitive patterns. More specifically, it is assumed that when illumination is made using a coherent light or plane wave in an oblique direction as shown in FIG. 29(a), such diffraction patterns as shown in FIGS. 29(b) and (c) are observed in a Fourier transform position. In this case, upon change in the pitch of patterns on the substrate, not only diffraction pattern pitches pu, pv, but also the entire phase changes. Further, when the basic shape of patterns on the substrate changes, the arrangement of spot patterns which form the diffraction patterns changes. That is, since there are many parameters which depict a Fourier transform plane-shaped diffraction pattern, it has so far been difficult to cope with each pattern shape.

Figure 29C:
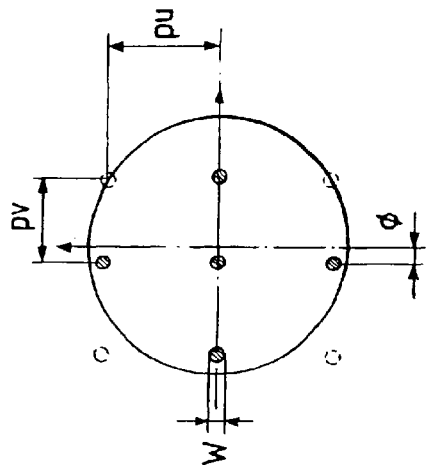
Figure 29A:
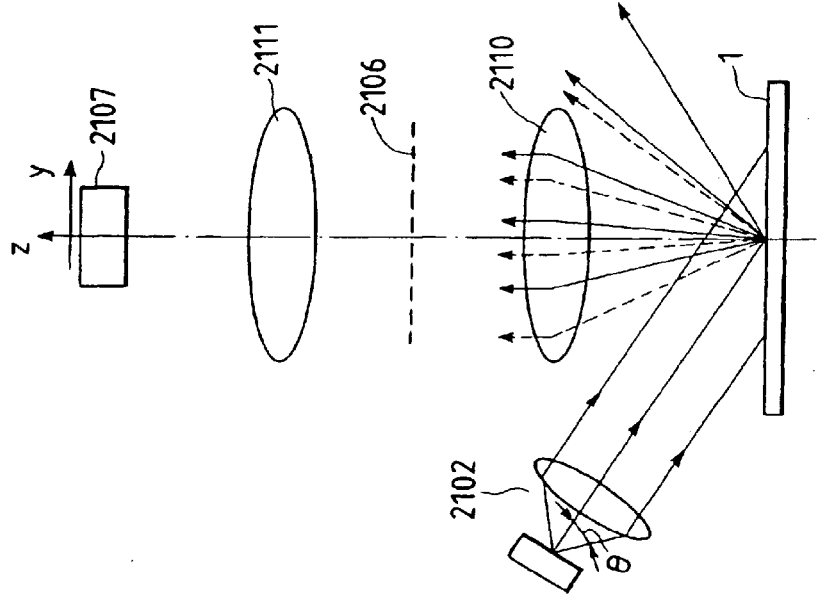

Now, consideration will here be given to the case where, not using such a plane wave as shown in FIGS. 29, but as shown in FIGS. 30(a) and (d), light is condensed on a sample 1001 in y direction, while in x direction, illumination is made using a coherent or plane wave. In this case, image is not formed in v-axis direction on the Fourier transform plane, but there is obtained a diffraction pattern of a shape compressed in the u-axis direction. Eventually, the spatial filter 2106 is compressed to a one-dimensional parameter only in u-axis direction. In this case, the pitch p in u-axis direction of the compressed diffraction pattern is in accordance with the pitch in x-axis direction of the illuminated area on the substrate surface. The thickness w of the diffraction pattern on each line is determined by a numerical aperture $\sin \beta$ of a front-side Fourier-transform lens 2110 for the Fourier transform plane, more particularly, by both the numerical aperture on the exit side of the lighting system 2102 and that of the front-side Fourier transform lens 2110. Thus, the thickness w is determined depending on the lighting system 2102 and the Fourier transform lens 2110, not influenced by the patterns on the substrate 1001 to be inspected. In some case, however, the numerical aperture in illumination is changed, or the width of the linear spatial filter 2106 may be variable.

Actually, moreover, for realizing high-speed inspection, a one-dimensional image sensor capable of making a continuous scan for stage (not shown) is suitable as the detector 2107. In the case of using such one-dimensional image sensor, illumination in the shape of a one-dimensional sensor, namely, a rectilinear shape on the surface of the sample 1001, is suitable for improving the illumination efficiency. For realizing such illumination, it is necessary to condense light at least in one direction. That is, a unidirectional coherent illumination is very effective also in improving the efficiency of the illumination intensity.

Heretofore, as set forth above, there are various shapes of patterns on the substrate and it has been considered to provide spatial filters respectively for those various patterns. According to the present inventions however, when viewed from a different viewpoint, it can be considered that such spatial filters are a function of only the pitch p. It follows that spatial filters having multi-dimensional parameters have been compressed to a one-dimensional structure. Thus, by compressing the dimension of the parameters of spatial filters, it is made possible to simplify the spatial filters to cope with all the repetitive patterns.

The above construction is applicable to all kinds of objects to be inspected in which not only foreign particles or defects present on a wafer or a liquid crystal display but also a portion having non-repetitiveness should be detected from each pattern having repetitiveness. More particularly, the above construction is applicable to semiconductor masks, reticles, micromachining parts using a semiconductor process, other micromachining parts and printed circuit boards. In the present invention, such objects are inspected at high speed by realizing illumination of a high illuminance while using the spatial filtering technique without replacing spatial filters for each object.

(Spatial Filter Control and Operator Pitch Control)

With reference to FIGS. 31(a) and 31(b)(1)–31(b)(3), description is now directed to 31(b)(1) a pattern erasing method using the spatial filter 2106, 31(b)(2) a pattern erasing method using a shot comparison operator in the operator pitch processing system 2203, and 31(b)(3) a TEG pattern erasing method using software in the software processing system 2210 (2206 to 2211). According to the construction of the present invention, the repetitiveness of cells not larger than several hundred microns in pitch is pattern-erased using the spatial filter 2106; the repetitiveness of several hundred micron pitch or more based on 31(b)(2) shot comparison operator in the operator processing systems 2203 (2217) is pattern-erased using the repetitiveness between adjacent chips (as the case may be between shots which interval means a single exposure); and as to chips (TEG patterns) not having repetitiveness, data are erased to omit inspection using coordinate-metric data in the software processing system 2210 (2206 to 2211). There are parameters respectively necessary in such erasing operations. In the case of erasing using the spatial filter 2106, a spatial filter pitch is necessary; in the case of erasing using the repetitiveness between chips, a chip-to-chip pitch is necessary; and in the case of erasing chips (TEG patterns) not having repetitiveness, chip position information is necessary. Therefore, it is desirable that the detection head 2101 of the present invention can detect at least two chips at a time. That is, it is necessary that the field size of the detecting optical system 2103 in the detection head be at least a two-chip length. Of course, this is merely to say that it is desirable for the field size to satisfy the said condition. If a positional relation of plural detection heads 2102 is known exactly in advance and this positional relation is memorized in the parameter transfer means 2209, further if this comparing processing is performed between the plural detection heads 2101 in the operator processing system 2203 for example, it is not necessary for the field size to be a two-chip length or more. However, when the accuracy required for the optical system (detection head) 2101 and the complicatedness of the circuitry for data processing in the operator processing system 2203 and the software processing system 2210, are considered, it is desirable for the field size to have a two-chip size or larger. Although explanation has been given here on the assumption that the field size is a two-chip size or larger, in the case where two or more chips are written on a reticle used as a mask, at the time of transfer of pattern onto the wafer, patterns called test element group (TEG) patterns are in many cases written between those chips, and for erasing also these patterns, using the foregoing repetition pitch, it is necessary to use the pitch (stored in the parameter transfer means 2209) between shots (patterns printed by a single exposure, the patterns on the reticle). Of course, this method is not always necessary, and even if the TEG patterns formed in one shot are erased in a subsequent processing, there will be no problem.

These pieces of information are measured in advance in correspondence to the substrate 1001 and stored in the parameter transfer means 2209. From among these stored pieces of information, parameters corresponding to the substrate are selected and fed back to the foreign particle defect inspection apparatus of the present invention (to the operator processing system 2203 through the software processing system 2210 and the parameter transfer means 2209). In the case of using this method, therefore, it is necessary to identify the substrate. For the purpose of this identification, a number or symbol corresponding to each substrate is described on the substrate. Operations may be performed through a procedure comprising reading such symbol before the inspection, checking production number, lot number and kind on the basis of the symbol thus read, then grasping a process concerned from the data of the place where the foreign particle inspection apparatus of the present invention is installed, and setting them in the pitch detecting means 2212 through the parameter transfer means 2209 to set a pitch of the spatial filter 2106 as well as threshold value.

In realizing the foreign particle defect inspecting method of the present invention, it is not always necessary to obtain parameters as explained above send them to the apparatus of the present invention in the manner described above. Rather, there also is the case where it is desirable for the parameters to be obtained independently by the apparatus of the present invention, as will now be explained. Although in the above method it is necessary to know the values of input parameters in advance, such operation is not necessary in the case of obtaining them independently by the apparatus of the invention, nor is it no longer required to read the symbol described on the substrate.

In the present invention, as explained above, since foreign particles deposited on a substrate having complicated background patterns or defects thereon are extracted and detected distinguishedly from the back ground patterns, there is used a three-stage pattern eliminating function. According to this function, a portion which has been judged to be a pattern is discarded without being regarded as an object to be inspected. More specifically, repetitive patterns having a pitch of several hundred microns or less are erased by the spatial filter 2106, while repetitive patterns having a pitch of several hundred microns or larger are erased using the repetitiveness between chips and on the basis of parameters provided through the parameter transfer means 2209, in the operator processing system 2203. Further, as to chips not having repetitiveness, related data are erased to avoid inspection in the software processing system 2210, etc. on the basis of coordinate-matrix data stored in the parameter transfer means 2209.

The reason why such pattern-formed area is eliminated from the object of inspection is as follows. Between adjacent chips there are formed patterns having the same shape and emitting the same quantity of light in the same direction. Therefore, by comparing detected intensities of light rays from these two patterns, it ought to become possible to inspect foreign particles or defects even in an area where there are formed patterns incapable of being erased by the spatial filter 2106. However, particularly in the case of detecting scattered light from these patterns, the intensity of the detected light is apt to become unstable, and so if the elimination of patterns by comparison is executed, false information (a pattern information not corresponding to a foreign particle is detected as a foreign particle) increases. Therefore, in some case it is rather effective to exclude the pattern-formed area from the object of inspection. More particularly, with stability in mind, in the case of detecting scattered light, a decision should be made as to whether an area with complicated patterns formed therein should be excluded from the object of inspection or detected intensities of light rays from adjacent chip patterns should be compared with each other for the inspection of foreign particles.

(How to Obtain Parameters)

Figure 32:
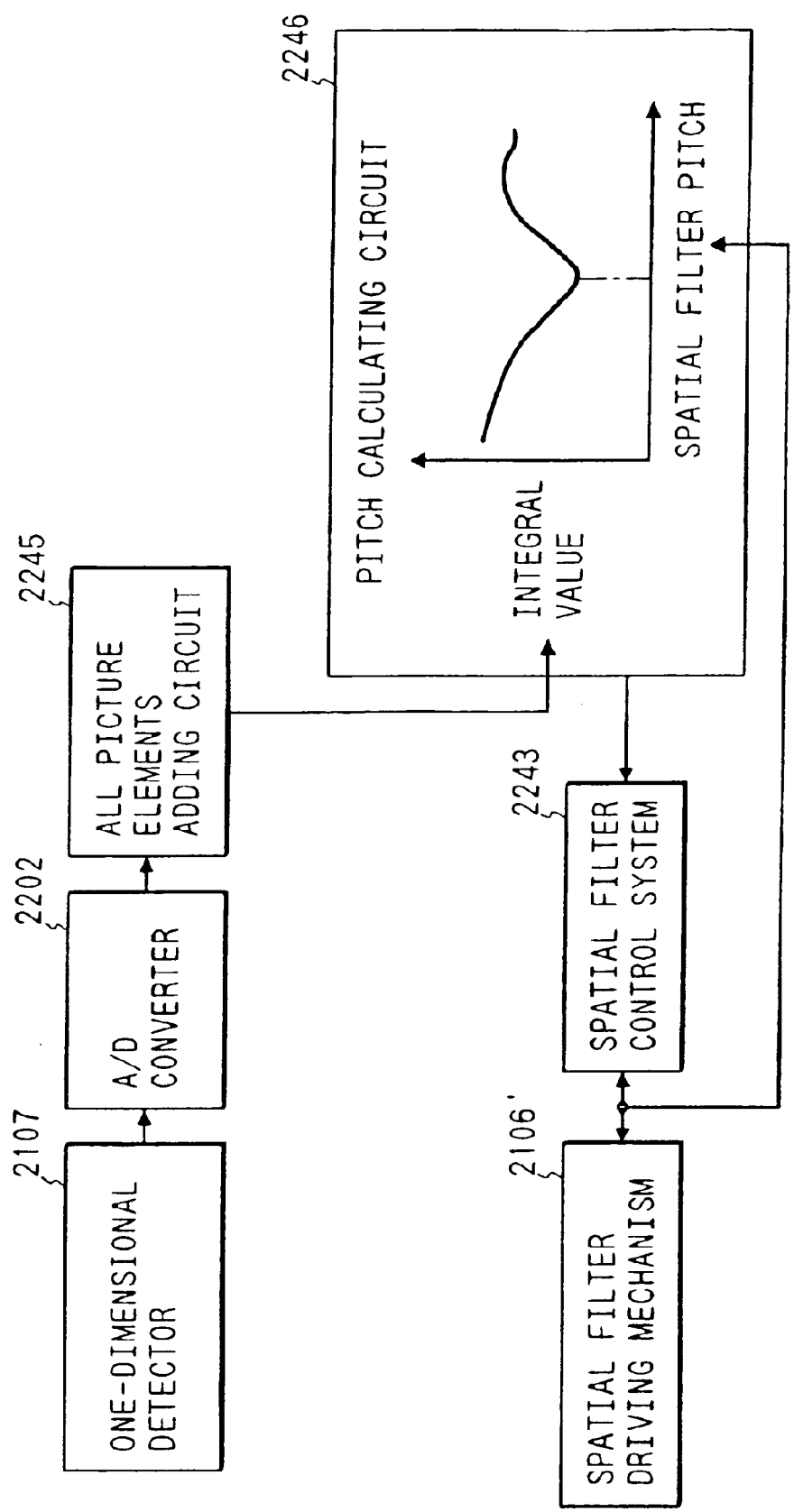
FIG. 32 is a block diagram showing another example of a parameter detecting system according to the present invention.

A concrete method for obtaining parameters will now be described with reference to FIG. 32. When the wafer 1001 has been conveyed to the position in which the detecting optical system 2101 can take in repetitive patterns on the wafer, the spatial filter control system 2243 causes the pitch of the spatial filters 2106 to be changed from a maximum position to a minimum position. At this time, with respect to the signals which have been taken in the one-dimensional detector 2107, all the values of picture elements are added together by an all picture elements adding circuit 2245, and a pitch in a position in which the thus-added value is the smallest relative to changes of pitch is selected by a pitch calculating circuit 2246. This value is sent to a spatial filter driving mechanism 21061 and the spatial filter 2106 is set to a predetermined pitch.

In selecting a pitch of the spatial filter 2106, calculation can be made also by executing the analysis shown in FIG. 28 even without changing the spatial filter 2106 as above. When the wafer 1001 has been conveyed to a position in which the detecting optical system 2101 can take in repetitive patterns on the wafer, a signal detected by the detector 2107 is analyzed for frequency by the FFT circuit 2242, and on the basis of the result of this frequency analysis there is selected a spatial filter pitch by the spatial filter pitch calculating means 2244 so as to provide a spatial frequency which is a peak in the frequency region. This value is sent to the spatial filter driving mechanism 2106' through the spatial filter control system 2243, and the spatial filter 2106 is set to a predetermined pitch. For this frequency analysis, fast Fourier transform is most desirable from the standpoint of processing speed, etc., but no limitation is made to fast Fourier transform. There may be adopted another method such as, for example, Hadamard transform, frequency analysis by integration, or auto-correlation function calculation. In the frequency analysis method, not only the spatial filter pitch but also the chip-to-chip pitch (operator pitch) for the method of eliminating components incapable of being removed by the spatial filter is subjected to an arithmetic processing by the operator pitch calculating means 2241. As to this chip-to-chip pitch, it is desirable to use a maximum one among those calculated by frequency analysis and those smaller than half of the visual field of the detecting optical system. This is because in many cases the maximum pitch corresponds to a shot-to-shot pitch which will be described below.

After parameter values for inspection have been set as above, inspection is executed.

The method described above involves a problem such that the initial portion of the wafer 1001 being conveyed cannot be inspected for foreign particle. On the other hand, it has an effect such that the inspection apparatus can be made independent with respect to the other signal transfer system.

(Telecentric Optical System)

According to the construction of the present invention, as explained above, repetitive patterns of a several hundred micron pitch or smaller are erased by the spatial filter 2106, while repetitive chips having a several hundred micron pitch or larger are erased by using the repetitiveness between chips, and further, as to chips not having repetitiveness, related data are erased to avoid inspection. For erasing detected chip pattern signals by utilizing the repetitiveness between chips, there is adopted a construction in which detected signals from chips are compared with each other, and when the difference is larger than a certain value, it is detected as a foreign particle. That is, this construction is based on the premise that scattered or diffracted light rays from patterns in adjacent chips are equal in intensity. Therefore, it is necessary to detect light rays from corresponding positions of adjacent chips stably. However, a diffracted light from pattern has directivity, so in the case where the visual field is wide and lens viewing angles from various positions in the visual field are greatly different, this directivity results in different light intensities according to positions in the visual field.

The telecentric optical system 2103' is of a technique developed to make main light rays from various points on the wafer 1001 parallel with each other and thereby prevent changing in the focusing magnification even in the event of deviation of the focal position. By using the telecentric optical system 2103' in the present invention, the intensities of detected light rays from various points of the wafer can be maintained constant stably. According to the present invention, since it is possible to make illumination in the same direction at all points of the wafer 1001 and make detection in the same direction from all points, even When diffracted or scattered light from pattern has directivity, there is obtained the same intensity of detection light if only the pattern shape is the same.

Thus, changing the magnification is for changing the picture element size. If the picture element size is enlarged, the inspection speed can be increased eventually because the area detected as one signal becomes larger, but it becomes difficult to detect a small foreign particle or defect because the resolution of the detection system is deteriorated. Conversely, if the picture element size is made small, the resolution becomes high to permit inspection of a smaller defect or foreign particle, but the inspection time becomes longer. Of course, in this case, it is necessary to make the resolution of the optical system also high.

Figure 33B:
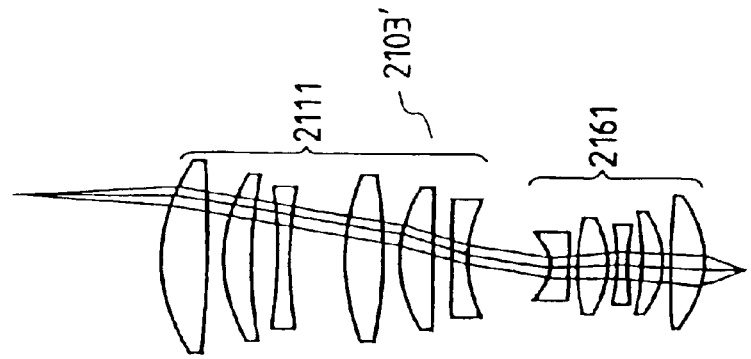
FIGS. 33(a) and 33(b) are construction diagrams of detection lenses according to the present invention.
Figure 33A:
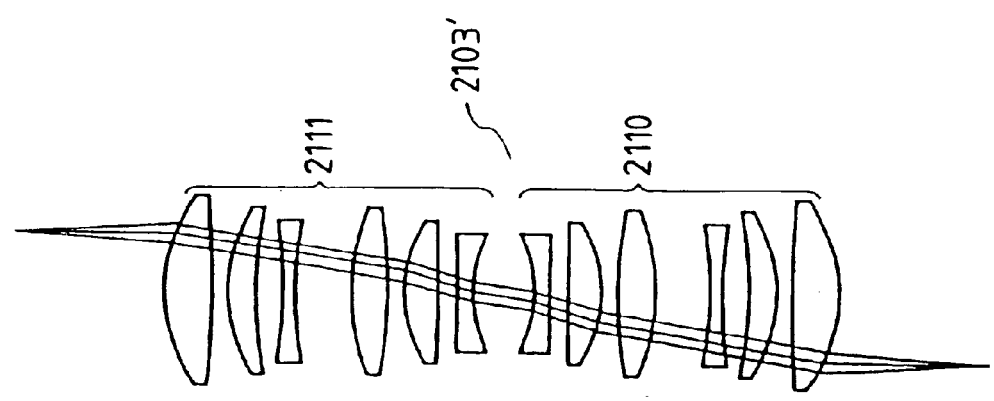

A lens replacing mechanism will now be described with reference to FIG. 33. In the illustrated embodiment there is used a telecentric optical system 2103' of a 1:1 focusing magnification, as described above. Being telecentric is important for attaining the effect of the present invention to a satisfactory extent. It is not necessary that the magnification be 1:1 as shown in FIG. 33(*a*). Therefore, it is also possible to use an optical system of another magnification. In realizing such optical system of another magnification, it is possible to make the change of magnification by replacing one (the object-side lens is most suitable) of the two groups of Fourier transform lenses 2110 and 2111 disposed on both sides of the spatial filter into Fourier transform lenses 2161. With this construction, it is no longer necessary to replace the image-side lenses 2111 and detector 2107 and eventually it becomes possible to provide optical systems of different magnifications inexpensively.

Thus, it can be expected that the telecentric optical system 2103' or an optical system in which main light rays from various points on the substrate 1001 pass through the center of the pupil (the spatial filter 2106 disposed plane) of the detecting optical system 2103 will exhibit a significant effect when used in the foreign-particle defect inspection apparatus using the spatial filter 2106. However, not only in the case of using the spatial filter 2106, but also in the application to a foreign particle defect inspection apparatus not using the spatial filter 2106, there arises an effect such that a high intensity can be detected stably. A significant effect can be obtained particularly in the case of using an optical system having a large visual field.

(Basic Concept of PRES Filter)

In the PRES filter according to the present invention, as set forth above, the greatest effect can be exhibited by using both a telecentric type detection lens and an illumination system which is coherent only in one axis, but a combined use thereof is not always necessary in realizing an apparatus for inspecting defects such as foreign particles, using the spatial filter 2106, which is the original object of the present invention. The reason why only one side is made coherent in illumination is that coherence is needed in using the spatial filter and that only one side is sufficient. Further, since one side is not coherent, the illumination light beam can be condensed on an object and thus it is possible to enhance the illumination intensity. Conversely speaking, if only there is obtained a sufficiently high illumination light intensity, the illumination may be coherent in both x and y directions. That is, the essence of the present invention resides in that spatial filtering becomes possible by matching the rotational direction of the substrate (wafer) 1001 in the case of the spatial filter 2106, in a one-dimensionally compressed state.

Of more importance is that in order to obtain one parameter of the spatial filter in the case of oblique illumination using the lighting means 2102, the linear spatial filter 2106 should be made parallel to the incidence surface in the illumination, and the use of illumination which is coherent only on one side is not intended. That is, it is the essence of the invention to take matching among the incidence surface in the illumination, the longitudinal direction of the linear spatial filter and the repetitive direction of patterns on the substrate (wafer).

When it is not necessary to make the number of parameter to be obtained into one, it is not necessary, either, to make the linear spatial filter parallel to the incidence surface in the illumination, and spatial filters capable of coping with all patterns can be constituted by matching pitch and phase or matching pitch and rotational direction, using linear spatial filters. Further, for illumination from above, there also is an effect such that only the direction of spatial filters and the repetitive direction of patterns on the substrate (wafer) may be matched together because the incidence surface in illumination and the direction of linear spatial filters are always coincident with each other.

In all of the above cases, however, there arises the necessity of performing such direction matching operation if a rectilinear shape of beam is used for illumination or a one-dimensional sensor is used as the detector 2107. However, this matching operation is for obtaining uniformity of illumination or for eliminating a large cycle of repetition by utilizing chip-to-chip repetition, and it is not necessary in erasing a small cycle of pattern information by spatial filters.

Also as to the telecentric optical system 2103', although both-side telecentric optical system has been shown above, it is not always necessary for both sides to be telecentric. At least the object side should be telecentric. Being telecentric is not an essential condition if only main light rays of the lighting system 2102 at various points on the substrate, namely, zero-order diffracted light beams from various points on the substrate, pass through the center of the pupil plane (the spatial filter mounted plane) of the detecting optical system. Even in such a construction, it is possible to avoid variations in the pattern output based on the distribution of zero-diffracted light rays from patterns at various points. However, this method is somewhat deteriorated in performance as compared with the foregoing telecentric optical system because the incidence direction of illumination light to patterns differs. In some particular object, however, there also is-the case where this method is satisfactory.

Further, even without allowing main light rays in the illumination system at various points on the substrate, namely, zero-order diffracted light rays from various points on the substrate, to pass through the center of the pupil plane (the spatial filter mounted plane) of the detecting optical system, an apparatus for inspecting defects such as foreign particles, using spatial filters, which is the original object of the present invention, can be realized also by using the ordinary high field lens.

(Method for Measuring θ in Advance)

In the case of the inspection apparatus described above, it is necessary that the inspection apparatus be matched to the angle of wafer or substrate. More specifically, it is necessary to set the detector and illumination optical axis perpendicularly or in parallel with the repetitive direction of patterns formed on the substrate. For the execution of this setting operation, it is necessary to detect a substrate angle during conveyance of the substrate with a high accuracy using an angle detecting mechanism and, on the basis of the result obtained, turn the whole of the detecting optical system with the substrate face normal line as an axis to make the pattern direction coincident with the detector direction.

Figure 35:
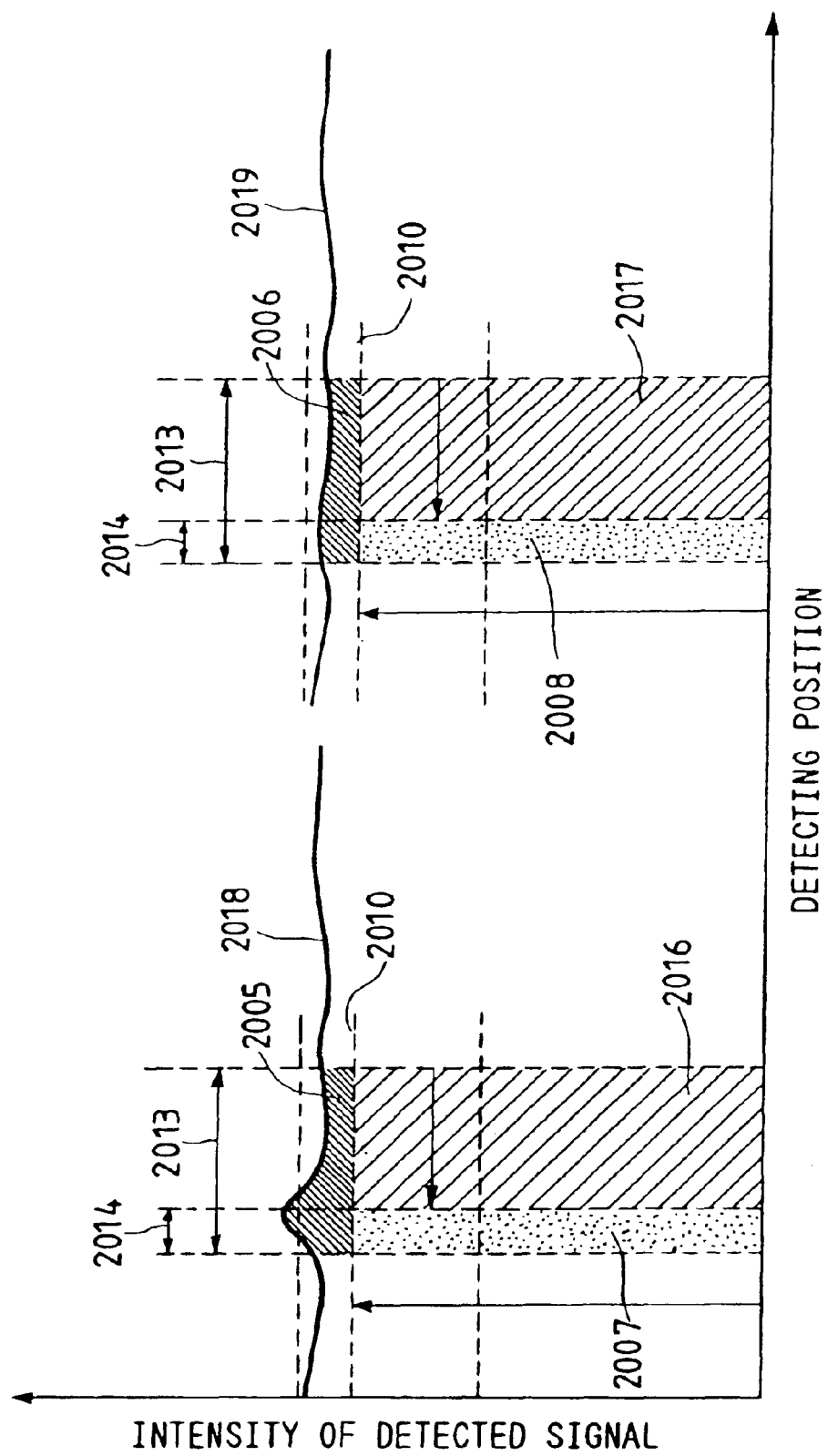
FIG. 35 is a schematic diagram showing the effect of a comparative inspection using an optical method according to the present invention.

A concrete construction is shown in FIG. 34. FIG. 34(*a*) illustrates the arrangement of a spatial filter unit 2106 formed on a Fourier transform plane and rotational direction detectors 2123, 2124, in which the detecting optical system 2103 is seen from the substrate side. A linear spatial filter 2141 and a diaphragm 2141 for restricting the pupil size is also shown. The detecting optical system 2103 is formed to have a somewhat large numerical aperture, and diffraction patterns from the substrate 1001 with parameters compressed protrude to the outside of the diaphragm 2142 and are detected by the detectors 2123 and 2124. Therefore, if zero-order diffracted light out of the diffraction patterns is detected and a variation in its peak positions is detected, a rotational direction of the detection head in the detecting optical system relative to the substrate is measured. More specifically, it is assumed that the spacing between the two detectors 2123 and 2124 is Lp and that the distance between diffracted light peak positions detected, from the center of the detector 2123 is hp1 and that from the center of the detector 2124 is hp2. A diffracted light under deviation of the rotational position exhibits such a shape as shown in FIG. 35(*b*) on the Fourier transform plane, so a rotational angle θp is generally expressed by the following equation (Equation 13). FIG. 34(*b*) is a view in which a spherical surface including the Fourier transform plane is seen in the direction of the Fourier transform plane. In the same figure, a circle 2003 represents light rays on the said spherical surface and the substrate surface, while a circle 2004 represents light rays on the said spherical surface and the pupil face 2142, and a dot 2005 represents an intersecting point between zero-order diffracted or reflected light of the illumination light and the aforesaid spherical surface:

$$\sin \theta p = hp1/Lp \quad (10)$$

Strictly speaking, the diffracted light pitch Ldp is unknown, so by re-measuring the distance between diffracted light peak positions, in a rotated position by a known, very small rotational angle θk, and setting up a simultaneous equation using hp11 and hp21, there can be calculated Lpd and θp. According to another method, adjustment is made while rotating θ so that both hp1 and hp2 become zero.

In rotating the detecting optical system 2103 in a direction easier to detect, it is not always necessary to rotate the whole of the optical system 2101, but the spatial filter 2106 may be rotated, because the purpose is to erase patterns formed on the substrate 1001, using the spatial filter. In rotating the optical system 2101, it is optional whether several units should be rotated at a time or rotation should be made for each unit.

Of importance in this construction is that a rotation matching with the substrate is taken by moving the detecting optical system 2101 without rotating the stage which supports the wafer or substrate 1001. This can be realized because the construction of the foreign particle detecting apparatus according to the present invention permits detection even when complete perpendicularity to the flowing direction of the substrate 1001 is not obtained. As another important point, the rotation of the substrate 1001 is associated with the rotation of the optical system 2101, and a conveyance system (not shown) for the substrate 1001 is used for scanning of the optical system 2101 relative to the substrate. Thus, two mechanisms are allowed to have two degrees of freedom independently to thereby simplify each mechanism.

It is not always necessary for the angle detecting mechanism 2108 to take such a method as shown in FIG. 34. A pattern direction on the substrate 1001 may be calculated on the basis of images detected by the detector 2107. This is effective in that such mechanisms as the detectors 2123 and 2124 become unnecessary, although a real-time measurement is difficult.

(Rotation Control for Optical System)

It is also possible to correct a rotational error by an electric processing without rotating the optical system 2101 or 2180 on the basis of the result of detection of a rotational error. As shown in FIG. 27, by shifting a square operator which has been taken out from the buffer memory 2217, in the e direction in accordance with a detected rotation error of the wafer, there is created an effect as if the rotation error of the substrate (wafer) were corrected mechanically. This method is effective in that the time required for the correction can be shortened because it is not necessary to move the optical system 2101 or 2180. According to another method using this circuit, the inspection is continued under such condition as minimizes detected foreign particles, which condition corresponds to a rotation error-free state of the substrate 1001 and detection head 2101, while allowing the operators 2219 and 2231 to move in the θ direction at all times, without measuring a rotation error θ. It goes without saying that a high-speed signal processing system is used in this method. Alternatively, even without using a high-speed signal processing system, inspection can be executed as if a rotation error of the substrate (wafer) were corrected mechanically by setting the above-mentioned condition in the manner described above, prior to the inspection.

Of course, the method disclosed herein is not always needed. For example, in the case where the substrate (wafer) 1001 is conveyed after mechanical adjustment of a rotation error of the substrate in a certain allowable range relative to the conveying direction, such as in the introduction into a reductive projection aligner, it is not necessary to use a detection control system as noted previously.

(Log Scale Threshold)

FIG. 35 schematically shows the state of a detected signal obtained in a comparative inspection using an optical processing method such as spatial filters as a preprocessing and that of a detected signal obtained in a comparative inspection using only an electric signal without using such processing. According to the method using the spatial filter 2106, it is possible to eliminate only pattern information without loss of defect information in the pattern portion, but the method based on chip comparison can detect a foreign particle or defect signal only in a dynamic range at the time of photoelectric conversion. That is, in the case where a pattern signal is extremely large and a foreign particle or defect signal is extremely small, the latter signal is burred in the former signal, so it is difficult to detect the foreign particle or defect signal distinguishedly from the pattern signal.

In FIG. 35, detecting positions are plotted along the axis of abscissa, while the intensities of detected signals are read along the axis of ordinate. On the left-hand side there is shown a signal 2018 containing foreign particle or defect information 2004, while on the right-hand side there is shown a signal 2019 not containing foreign particle or defect information for comparison. When a picture element size to be detected as one signal is detected as 2013, there are detected light rays corresponding to hatched areas 2016 and 2017. In this case, since the foreign particle or defect information 2004 is small relative to the total area, the comparison between these two detected signals 2016 and 2017 cannot be made stably, which are burred in noise. For example, even if illumination light intensity is enhanced, it is necessary to use a detector of a large dynamic range in order to permit detection of the foreign particle or defect information 2004. If the picture element size is changed from 2013 to 2014, the detected signals obtained are 2007 and 2008, thus permitting detection of the foreign particle or defect information 2004 in a comparative manner. Reducing the picture element size gives rise to such an effect. Conversely, if it is possible to erase offset stably (in an essential comparison without change into an electric signal or the like) for the detected signals 2018 and 2019, more particularly, if signals can be detected in a cut state above the position of 2010 for example, there are obtained detected signals 2005 and 2006 which are in a level permitting a comparative inspection. In this case, a high-speed inspection using large picture elements becomes possible because the picture element size remains the same as the previous size 2013. If the illumination light intensity for example is enhanced, it becomes possible to detect the defect information 2004 such as foreign particles even by using a detector of a small dynamic range. The method using the spatial filter 2106 according to the present invention aims at detecting information 2004 of a very small foreign particle or defect while using the picture element 2013.

As set forth above, even if internal pattern signals between adjacent chips to be compared can be made extremely stable by giving some consideration to the optical system, a limit is encountered in point of light intensity, that is, the detection in a dynamic range of 1:100 or 1:1000 is the limit. Therefore, if a foreign particle or defect signal is small or pattern signal is large to the extent-of requiring a still larger dynamic range, it is impossible to judge in which signal a foreign particle or defect signal is contained through comparison of signal intensities between adjacent chips. Only when the ratio of a foreign particle or defect signal to a pattern signal is sufficiently large, it is possible to inspect comparatively whether a foreign particle is present or not. If this ratio is small, the presence of a foreign particle may be overlooked, or the number of false data may increase as the threshold value is made smaller to inspect foreign particles.

It is difficult to inspect foreign particles present on patterns, without false information, and the only way for solution to this problem is either eliminating false information or making the foreign particle detecting sensitivity small to permit detection of only large foreign particles. Thus, in the present invention there is used an embodiment in which the pattern-formed area is excluded from the object of inspection. This is intended to eliminate the false information explained above.

Further, in order to make the detection of only large foreign particles possible by reducing the foreign particle detecting sensitivity, it is necessary to conduct a comparative inspection on a log scale as will now be described. Even if patterns having the same shape and emitting the same quantity of light in the same direction are formed on adjacent chips, detected light rays from these two patterns are not completely the same. Therefore, it is quite likely that the light rays from the two patterns will scatter in intensity, and so it is difficult to make comparison. In comparing between a which has been taken out in the operators 2219l, 2231 and p which has been taken out in the operator 2218, by means of plural comparison circuits 2220, it can be judged that the two signals are different from each other, indicating the presence of a foreign particle, if Expression 11 is satisfied:

$$(a-p) > \delta \tag{11}$$

According to this method, however, when the absolute level of signal is high and when there is a scatter which varies at a ratio relative to such absolute quantity, there is an increasing possibility of the so-called false information, that is, judging that there is a foreign particle though actually there is not any foreign particle. In view of this point, when the ratio of two signals satisfies the following Expression 12, it is judged that there is a foreign particle:

$$(a/p) > \delta \tag{12}$$

Actually, however, the division for two signals requires a larger scale of arithmetic circuit, so a threshold value is set in terms of a logarithm, and when the following Expression 13 is valid, it is judged that there exists a foreign particle:

$$\log(a/p) = \log a - \log p > \delta \tag{13}$$

Thus, once a quantization threshold is set using a logarithmic axis according to the Expression 13, the arithmetic operation which originally requires division can be performed in terms of subtraction in the comparators 2220. It is the circuit configuration shown in FIG. 60 that realizes the logic explained above. Such logarithmic processing as explained above can be executed by setting the threshold of the octalizing system 2215 shown in FIG. 27, in terms of a logarithm.

Although in FIG. 27 there is shown a subtraction processing in the comparator circuits 2220 using the logarithmic octalizing processing at the octal coding system 2215 explained above, this method is not always the only method to be used. There may be adopted the above division processing as it is, or any other multi-value coding method than octal coding. If ternary coding is used, foreign particles on all patterns will be discarded without detection, and the use of a larger multi-value coding method permits detection of smaller foreign particles on patterns if only the optical system is stable.

In the threshold setting circuit 2221, the above value δ is set, and in the plural foreign particle comparing circuits 2220, there is made comparison on the basis of the above Expression 11, 12 or 13. Then, with respect to the signals wherein the difference between the operator (picture element) 2218 and the operators (picture elements) 2219, 2231 is above the foregoing threshold value δ, they are ORed in the OR circuit 2224, and "0" is outputted from all the foreign particle comparing circuits 2220, so that repetitive patterns between chips (shots) are erased. When there is a difference above the threshold value 6, an output is developed as "1" from any of the foreign particle comparing circuits 2220, indicating the presence of a foreign particle, and it is stored in the foreign particle data memory 2206. In the plural foreign particle comparing circuits 2220, moreover, a comparison is made on the basis of the above Expression 11, 12 or 13, and when the difference between the operator (picture element) 2218 and the operator (picture element) 2219 and that between it and the operator (picture element) 2231 are all below the foregoing threshold value δ, "0" is outputted from all the foreign particle comparing circuits 2220, and the output values are ANDed in the AND circuit 2226, then the result is detected as repetitive patterns between chips (shots) and stored in the pattern memory 2208.

FIG. 43 shows the state of quantization using the above logarithmic threshold, in which the axis of abscissa represents detecting position, while the axis of ordinate represents detected signal. Logarithmic threshold values 2050, 2051, 2052, 2053 and 2054 are set and signals located at portions spaced by pitch p are compared with each other. Now, switching is made into a multi-value and an allowable range for the judgment of identity at the time of comparison is multiplied by 1 for example, whereby not only pattern signals 2055 and 2058 which are quantized to the same value but also pattern signals 2056, 2059 and 2057, 2060 which are quantized to one different value are judged to be patterns, thus not causing false information. That is, by taking large the ratio of logarithmic threshold values in quantization, the allowable range becomes larger and so it is possible to diminish false information, but on patterns there can be detected only larger foreign particles. Besides, both foreign a particle signals can be detected. Further, since the operator 2231 is spread in the plane direction, it is possible to allow quantization errors in the plane direction.

Thus, there is an essential difference between the erasing of patterns using the spatial filter 2106 and that by comparison of chips. More particularly, according to the method using the spatial filter, internal defects of patterns can be detected emphasizedly, but in the method based on the comparison of chips, since comparison is made after photoelectric conversion and detection of internal foreign particle or defect information of pattern as it is, a large dynamic range is necessary. In the method using the spatial filter, there is obtained a shape as if only defects were emphasized by the comparison of cells using interference.

Figure 37:
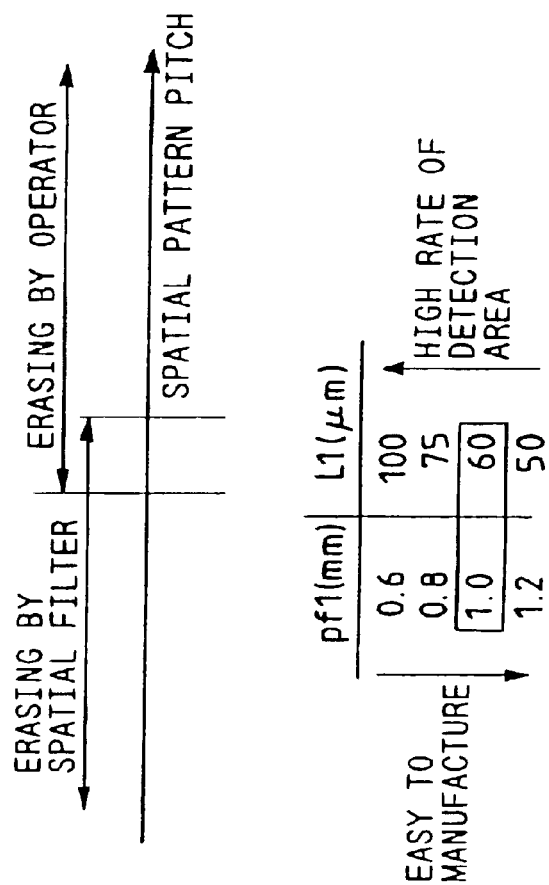
FIG. 37 is a schematic diagram explanatory of conditions for the erasing of pattern according to the present invention.
Figure 36:
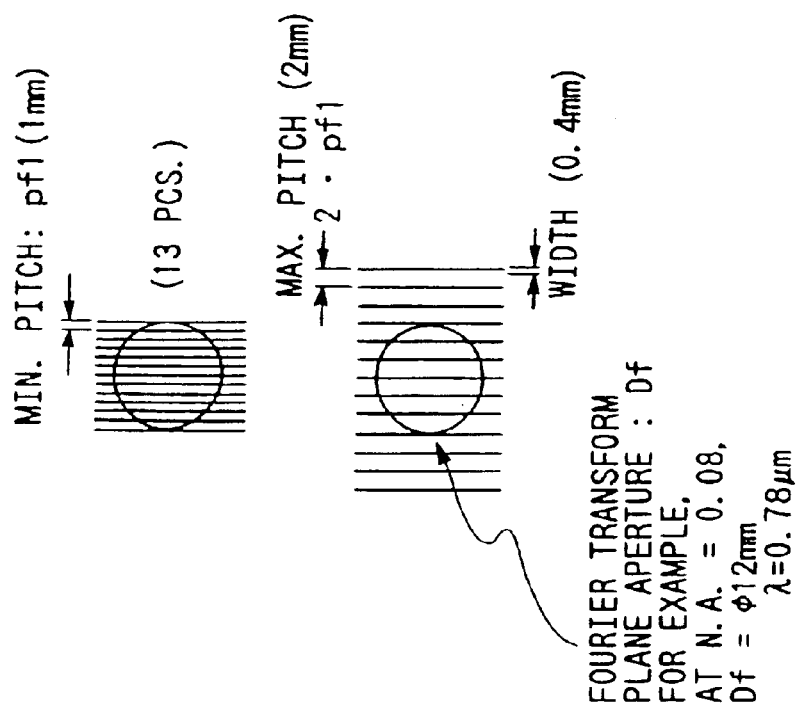
FIG. 36 is a schematic diagram explanatory of the shape of a spatial filter according to the present invention.

In order to erase the patterns of all pitches on the substrate, it is necessary that the maximum pattern pitch capable of being erased by a spatial filter is larger than the minimum pattern pitch erasable by operator, as shown in FIG. 37. Additionally, the larger a pattern pitch L1 erasable by the spatial filter, the higher the detection area ratio on the substrate due to decreased erasing by pixels of operator, but the smaller a pitch pf1 of the spatial filter, thus resulting in being difficult to manufacture spatial filters. Then, an example of PRES filters having variable pitch is shown in FIG. 36, in which the PRES filter are formed so that its pitch can successibly be changed ranging from the minimum pitch pf1 to the maximum pitch 2·pf1.

(Quantization Error in the Plane Direction and that in the Depth Direction)

The method using the chip-to-chip repetitiveness is basically a comparative inspection, but the following construction is used for effecting such comparative inspection stably in the detection of scattered light using a laser light spot source of short wavelength. The operators-for realizing the pattern eliminating method using chip-to-chip repetitiveness are formed of plural picture elements in both x and y plane directions. In the comparison as to whether signals should be judged equal in level or different in level because of presence of a defect or foreign particle in one of the signals, there are used Expressions 11, 12 and 13. By enlarging the sampling of comparative numerical values in the plane direction and the light intensity direction, it is possible to distinguish foreign particles and patterns from each other in a stable manner.

(Image Restoration by Convolution)

Figure 38:
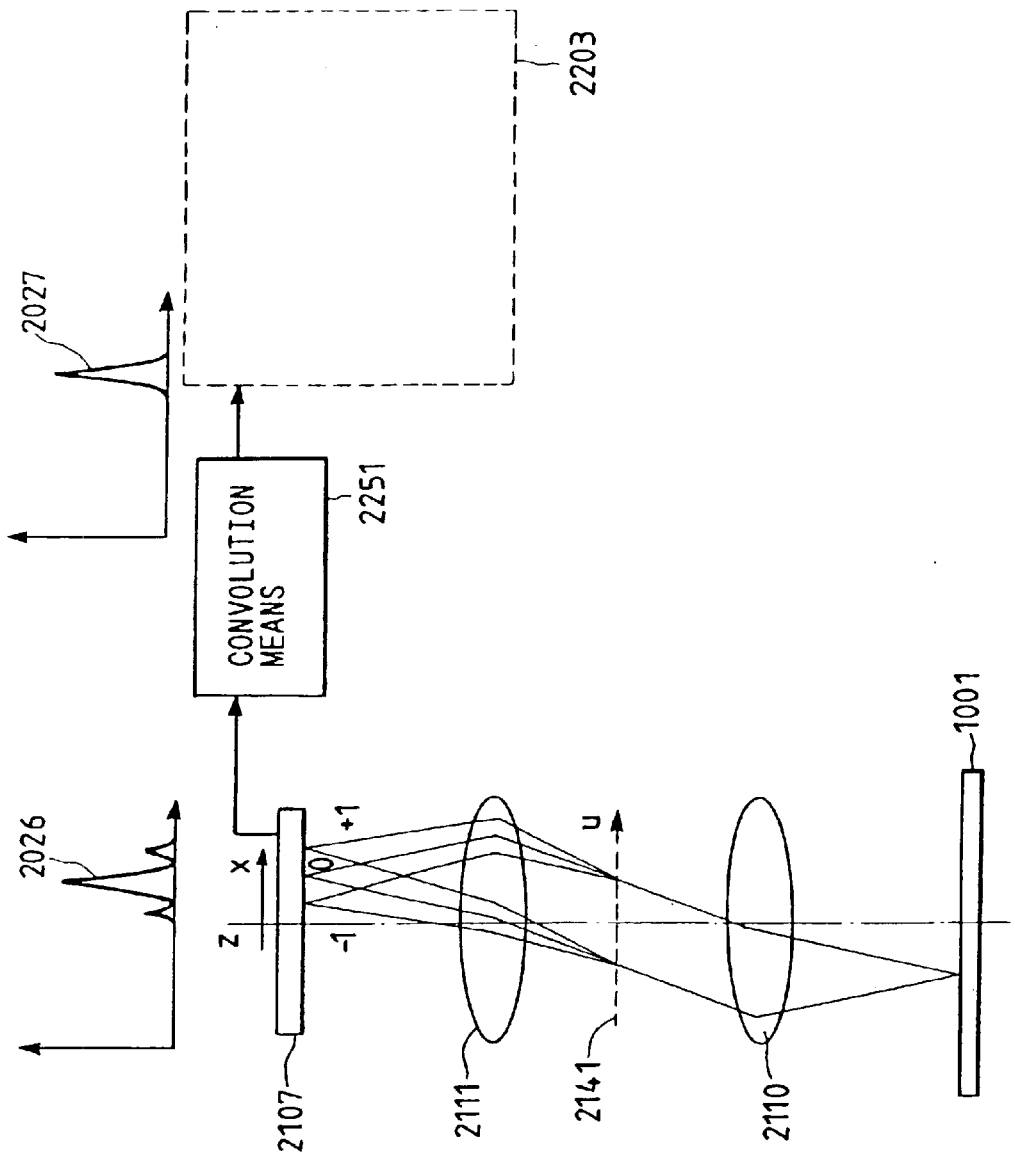
FIG. 38 is a construction diagram explaining how to remove the influence of diffraction in a spatial filter mechanism according to the present invention.

According to the apparatus of the present invention, as shown in FIG. 38, light rays are diffracted by the spatial filters 2141 which are arranged at equal pitches, to form a diffraction pattern on a focusing plane. More particularly, a diffraction image of spot image is formed on the focusing plane. In this image, there appear ±first-order diffracted light rays around zero-order diffracted light. Once there appear such diffracted light rays, there is obtained such a shape as the signal 2026 in which ±first-order peaks appear around the original peak for example, so that the number of foreign particle increases to three, which are detected. In the case of pattern, the portion judged to be pattern and erased or where the detection sensitivity is deteriorated, becomes larger. This can be avoided by narrowing the width of the linear spatial filter. More specifically, when the width of the linear spatial filter is half of the pitch of the spatial filters 2141, the first-order diffracted light is half as large as the zero-order diffracted light, while when the width of the linear spatial filter is one eighth of the spatial filter pitch, the first-order diffracted light decreases to one thirtieth of the zero-order diffracted light. These results have been calculated by Fourier transform of the shape L (u,v) of the spatial filter 2106. In some case, therefore, it is necessary to select an appropriate width of the linear spatial filter 2141 relative to the pitch of the spatial filter. Particularly, in the case where it is necessary to know a small ratio, it is necessary to change the way of light condensation in the position of Fourier transform of the light source illuminated onto the substrate 1001 by the lighting system 2102. This is attained by enlarging the numerical aperture of y-direction component of the incident illumination light on the substrate 1001. In this case, the size of image formed on the Fourier transform plane of illumination is calculated in accordance with a focusing theory of coherent light.

The influence of diffraction referred to above can be avoided also by an image processing method known as Wiener filter. More specifically, as shown in FIG. 38, if the spatial filter shape is L (u,v), the influence of diffraction can be avoided by obtaining the value of 1/L(u,v) in advance, calculating its Fourier transform and then convoluting the result into a detected image by a convolution means 2251. In this way, it is possible to eliminate the light diffracted through the spatial filter Since the value of 1/L(u,v) involves an infinitely diffusing portion, it is necessary to approximate this value to a sufficiently large necessary value. The value of complex number obtained as a result of Fourier transform is approximated so that the magnitude thereof becomes an absolute value of complex number, assuming that numerical values of substantial phase inversion are positive and negative. Also at the time of taking out images for convolution, setting should be made so as to provide a sufficiently effective minimum-size.

(Rotate Wafer in Conformity with Fine Pattern)

Figure 39B:
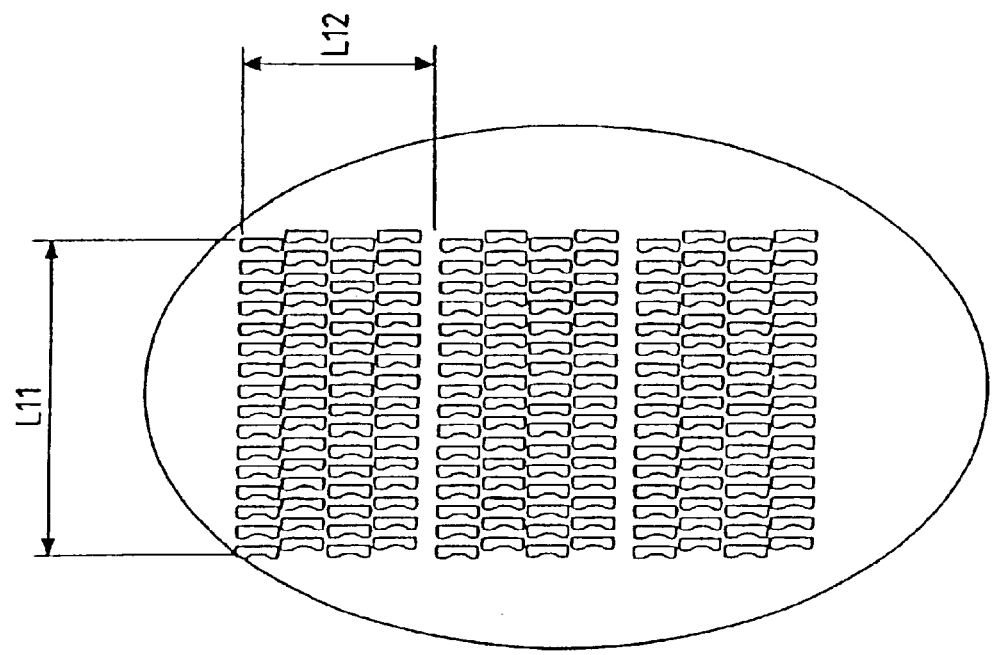
FIGS. 39(a) and 39(b) are schematic diagrams explaining a scanning direction of a sensor according to the present invention.
Figure 39A:
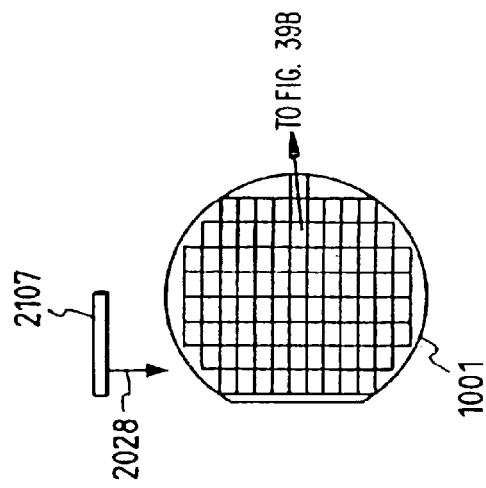

In the above pattern elimination using a spatial filter and repetitive chips, it is desirable that the pitch of patterns eliminated by the spatial filter be small and that the pitch of patterns eliminated by repetitive chips be large. Particularly, in order to reduce the area which is eliminated as pattern, it is preferable that the pitch of patterns eliminated by the method using repetitive chips be large. In inspection, therefore, it is better to decide a rotating direction of the substrate at the time of conveyance in accordance with the shape of patterns formed on the substrate. More specifically, as shown in FIG. 39(b), when there are pattern pitches L11 and L12 incapable of being erased by the spatial filter, it is better to scan in the direction of 2028 so that the direction of the larger pattern pitch L11 coincides with the sensor direction. To this end, there is adopted a construction in which the substrate 1001 (FIG. 39(a)) is rotated 90° prior to inspection.

(High Accuracy Foreign Particle Inspection Apparatus)

In the inspection apparatus using a spatial filter, as explained above, it is not the only object to attain high speed and small size. In just the same construction as above, if the resolution is improved by replacing the object-side Fourier transform lens, as in FIG. 33, more particularly, if it is improved to, say, one micron or so, it is possible to inspect foreign particles or defects having a minimum size of 0.1 to 0.3 micron or so at high speed. If the resolution is improved to 3 microns or so, it is possible to detect foreign particles or defects having a minimum size of 0.3 to 0.8 micron or so at high speed. Such a construction permits satisfactory erasing of pattern signals which cause noise, by utilizing the repetitiveness of patterns, so small foreign particles or defects can be inspected even when using a large picture element size, in comparison with the pattern inspecting apparatus using design data comparison, cell comparison or chip comparison, and hence eventually it is possible to attain a high-speed inspection. Also in this inspection, a pattern portion not having repetitiveness is excluded from the object of inspection. For such portion outside the inspection object, it is necessary to give some consideration, for example, inspecting in another inspection apparatus or executing a visual inspection.

(Utilizing Detection Head)

In the foreign particle or defect inspecting apparatus described above, it is most effective to inspect the substrate 1001 in one direction during conveyance thereof, so for inspecting the whole area of the substrate 1001, it is desirable to arrange plural inspection apparatus (detection heads) in parallel. However, as shown in FIG. 40, even if only a portion 2035 of the substrate is inspected using one unit of detection head 2101, a satisfactory effect is exhibited in many cases. This is because the generation of particles or defects can be fully detected by a partial foreign particle or defect inspection. of course, it is not always necessary to use only one unit. Plural units may be arranged where required.

There also may be adopted a construction wherein the whole substrate area is inspected by x-y scan of the stage, using one or more units of detection heads.

(Dynamic Inspection Conforming to Pattern Shape)

Figure 41:
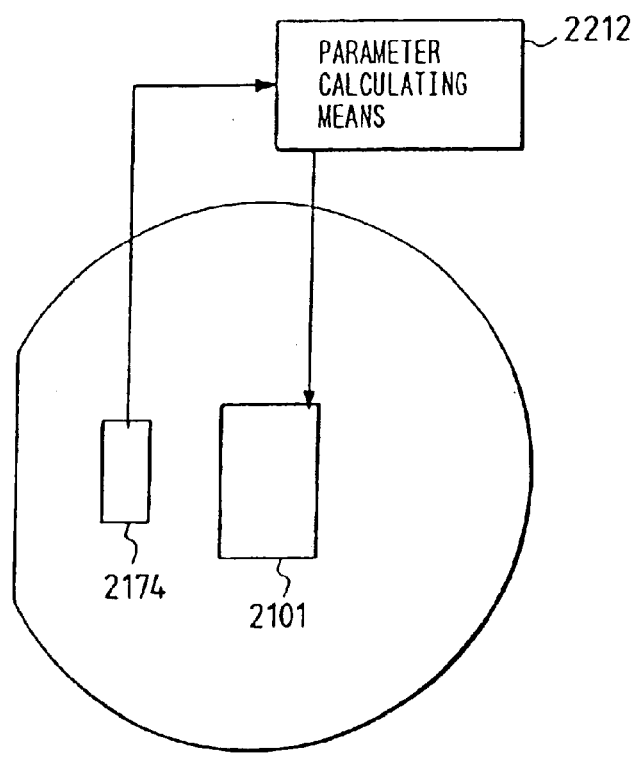
FIG. 41 is a construction diagram showing a pattern pitch measuring means according to the present invention.

FIG. 41 illustrates an inspection apparatus which is applied to the case where the pitch of repetitive patterns changes in the substrate. This apparatus comprises a repetitive pattern pitch detector 2174 and a detection head 2101.

As the substrate is conveyed, first a repetitive pattern pitch is calculated using, for example, the frequency analysis method described in connection with the parameter calculating means 2212, on the basis of a signal detected by the repetitive pattern pitch detector 2174. The pitch thus calculated is transmitted to the detection head 2101, and the spatial filter pitch and operator pitch are changed. In the detection head 2101, inspection is performed at the time when the pitch-calculated portion by the detector 2174 was conveyed to the inspecting position in the head. The inspection proceeds while pitch is calculated at all times. This method permits inspection in the case where the pattern pitch does not change discontinuously. In the event of discontinuous change of the pitch, it is likely that the setting of the pitch will not be performed in time. In such a case, it is necessary to stop the feed of the conveyance system until the setting of the pitch is completed.

(Diffraction Interference by Sine Curve Diffraction Grating)

A pattern inspecting method which combines diffracted light and interference light with each other, will be described below with reference to FIG. 42.

This apparatus is basically the same as the inspection apparatus using a spatial filter described above, and it comprises a lighting system 2102, a detecting optical system 2103, a spatial filter unit 2106 and a detector 2107. As additional components, this apparatus further includes a diffraction grating 2175 formed of a transparent substrate in the spatial filter position and having a phase distribution of a sine curve, and a drive mechanism 2176. In the method described above, a pattern eliminating processing using the repetitiveness of chips is realized by an electric processing system which is illustrated in FIG. 27. As explained above, this method has involved a problem such that foreign particles in patterns capable of being inspected are limited to particularly large ones. Further, as shown in FIG. 35 and explained above, information present in such large background noise can be detected by a method such as photo-processing which permits offset to be eliminated uniformly and surely. In view of this point, it is intended to execute the pattern eliminating processing using the repetitiveness of chips by an optical method, more particularly, an interference method.

Figure 42A:
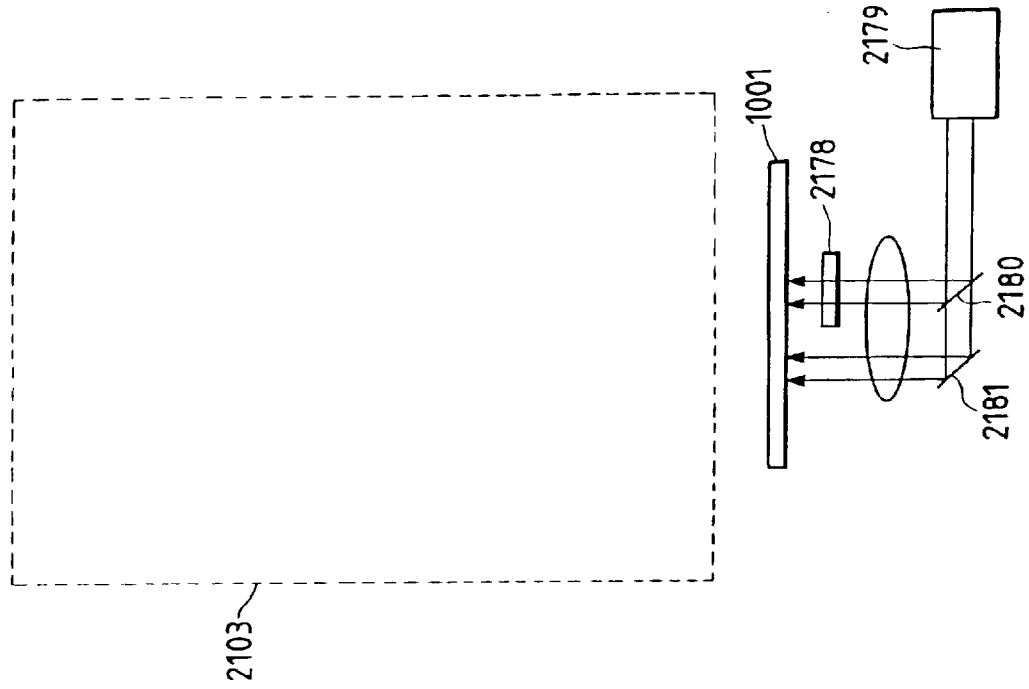
FIGS. 42(a) and 42(b) are construction diagrams showing a pattern removing method using interference according to the present invention.

Although the illumination light shown in FIG. 42 is a transmitted light, it may be a reflected light. In the illumination, a coherent illumination is performed at least uniaxially. In the presence of repetitive patterns 2037 and 2038, main light rays (zero-order diffracted light rays) from those patterns respectively travel along the respective optical axes and form their images on the detector 2107. However, since the diffraction grating 2175 is provided on a Fourier transform plane, the light rays are diffracted and emitted in first-order directions. Of importance in this connection is that since a sine curve (as is also the case with cosine curve) is used as the diffraction grating 2175r the zero-order diffracted light rays disappear (light intensity is zero) and only the ±first-order light rays are emitted. By adjusting the diffraction grating 2175 in the optical axis direction through the drive mechanism, + and −first-order light rays from patterns 2037 and 2038 can be put one upon the other on the detector. Further, by disposing a phase plate 2178 for shifting phase by $\pi$ on the illumination side or in a suitable position of the optical axis, it is made possible to let two light beams interfere with each other on the detector 2107. Eventually, by permitting fine adjustment of the change in phase of the phase plate 2178 so as to make it possible to also correct the phase of intermediate light beams, there can be realized a pattern eliminating processing using the repetitiveness of chips through interference.

Further, if the diffraction grating 2175 and the drive mechanism 2176 are operated so that the interstitial distance of the diffraction grating is changed suitably by changing the wavelength of ultrasonic wave, by means of a refractive index changing mechanism using a surface wave of ultrasonic wave such as SAW, the + and −first-order light rays from the diffraction grating 2175 can be directed in just the same direction and can be put one upon the other on the detector. This method is effective in that a sine curve can be formed automatically on the diffraction grating 2175. It is not necessary to move the diffraction grating 2175 in the optical axis direction. Of course, these means may be combined together.

Although a sine curve is used as the diffraction grating in the above method, this does not constitute any limitation. In the case of comparing patterns 2037 and 2038 which are spaced a sufficiently large distance from each other, it is not necessary to use a sine curve because the influence of zero-order diffracted light rays induced by the absence of sine curve can be prevented.

Figure 42B:
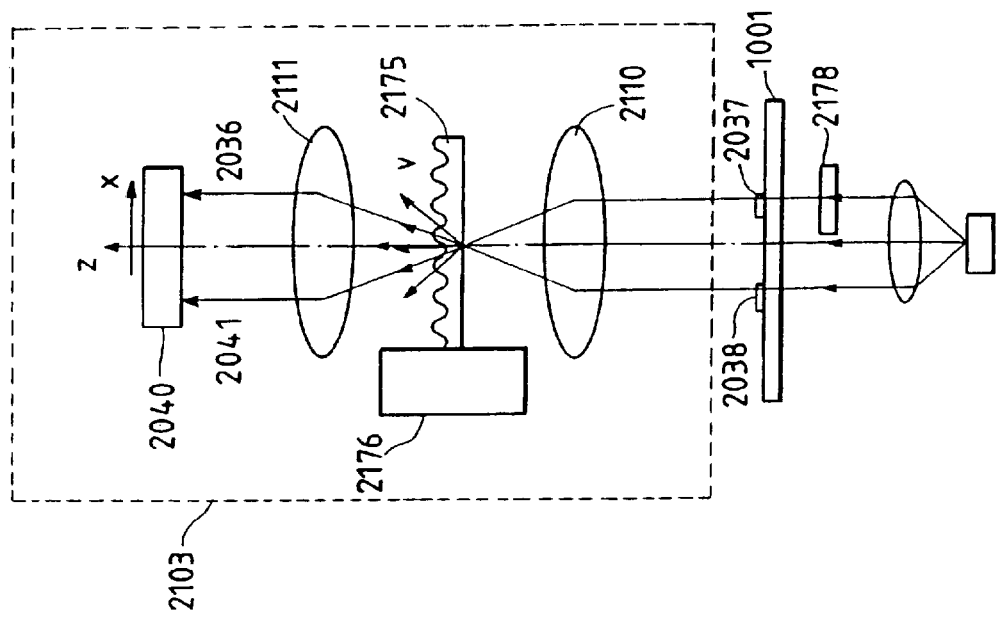

In FIG. 42(b) there is illustrated a construction in which, only the portions spaced apart by a pattern pitch are spot-illuminated for the illumination of patterns. In this construction, a light source 2179 is provided with a scanner, and only portions spaced apart by a pattern pitch are spot-illuminated through a half mirror 2180 and a mirror 2181. According to this construction, an accurate phase shift $\pi$ can be created and hence it is possible to improve the detecting performance.

(Others)

As set forth above, since the above inspection apparatus is for the inspection of foreign particles or defects on the substrate during conveyance, it is necessary that the substrate during conveyance be within a focal depth of the detecting optical system. Therefore, a larger focal depth is preferred to permit inspection even in a conveyance system whose accuracy is not so high. Therefore, for giving preference to the focal depth rather than the detecting resolution, a diaphragm may be disposed in the detecting optical system to enlarge the focal depth.

Although a linear filter is used in the inspection apparatus described above, it is not always necessary to use such a filter. There may be used a filter using a liquid crystal display element, or a reversible light cut filter using silver chloride, or a complex conjugate type non-linear element.

Although in the above embodiment the illumination light is light from information, i.e., reflected light, no limitation is made thereto for obtaining the effect of the present invention. There may be adopted a construction wherein the illumination light is a transmitted light.

Foreign particle or defect information detected by the apparatus of the present invention can be a clue to not only detect a trouble by counting the number of foreign particles or defects but also provide a generation distribution of foreign particles or defects and thereby estimate the cause of generation of such foreign particles or defects. It is desirable that suitable arrangement and number of monitors and sensitivity thereof in the invention be set on the basis of results obtained using a high accuracy inspection apparatus.

Although the illumination system used in the present invention is constructed as the illumination system 2102 independently of the detection system, this illumination system can be omitted by replacing it with a portion of the detection system. More specifically, this point can be attained by disposing a semiconductor laser and a cylindrical lens of an appropriate focal length on the Fourier transform plane of the detecting optical system. As a result, the detection head can be further reduced in size, weight and cost.

According to the present invention, since repetitive information can be omitted at high speed, defects such as foreign particles present as non-repetitive information can be detected at high speed from among repetitive patterns, and as a result, by introducing a small-sized foreign particle monitor into the line, it is made possible to inspect all of the wafers passing along the line. Thus, an increase in the number of foreign particles can be detected in real time. Consequently, the formation of a large quantity of defective products caused by the generation of foreign particles can be prevented and the yield can be improved thereby. That is, according to the present invention, by monitoring foreign particles using only a small-sized monitoring apparatus of a simple structure in a mass production line of the semiconductor manufacturing process, it becomes possible to reduce the weight of the production line and the manufacturing cost; further, since the said monitoring apparatus permits real-time inspection of foreign particles, it is impossible to minimize the incorporation of defects and thereby contribute greatly to the improvement of the product yield. According to the present invention, moreover, by providing a foreign particle inspection system in the mass production starting line and that in the mass production line separately from each other in the semiconductor manufacturing process, and by using a foreign particle inspection apparatus of high accuracy, the detecting, analyzing and evaluating functions required at the time of starting of mass production can be exhibited to a maximum extent, so it is possible to effect feedback to the mass production line smoothly and shorten the mass production starting period. In the mass production line it is possible to effect a high frequency sampling close to total inspection using a minimum number of small-sized foreign particle monitors, whereby it is made possible to obtain products of high quality in high yield.

What is claimed is:

1. A processing method for semiconductor devices in a semiconductor fabrication line, comprising the steps of:

processing a substrate in a first processing apparatus;

transferring the substrate processed in the first processing apparatus to a detecting apparatus without removal of the substrate from the semiconductor fabrication line while continuing fabrication of the semiconductor devices;

detecting foreign particle defects on the substrate transferred to the detecting apparatus utilizing a foreign particle detector having a pitch variable spatial filter to cut a light reflected from a pattern formed on the substrate, wherein a light cutting portion of the pitch variable spatial filter is pitch variable according to the pattern;

sending a detected signal from the detecting apparatus to a foreign particle detecting processing apparatus which is separate from the detecting apparatus;

processing the detected signal sent from the detecting apparatus by the foreign particle detecting processing apparatus;

determining a foreign particle generation condition of the first processing apparatus based on information processed by the foreign particle detecting processing apparatus;

transferring the substrate detecting in the detecting apparatus to a second processing apparatus in the semiconductor fabrication line; and processing the substrate in the second processing apparatus, wherein an amount of the foreign particle defects detected in the detecting step is stored in a memory.

2. A processing method according to claim 1, wherein in the detecting step, detection is performed in a predetermined area of the substrate.

3. A processing method according to claim 1, wherein in the detecting step, detection is completed within a processing time in the processing step.

4. A processing method according to claim 1, further comprising controlling an operation of the semiconductor fabrication line in accordance with the data foreign particle defects detected.

5. A processing method according to claim 1, further comprising obtaining information of distribution of foreign particle defects on the substrate and storing the obtained information in the memory, wherein the step of detecting foreign particle defects is performed in real time.

6. A processing method for semiconductor devices in a semiconductor fabrication line, comprising:

processing a substrate in a first processing apparatus which is a component of the semiconductor fabrication line;

detecting foreign particle defects on the substrate processed in the first processing apparatus utilizing a detecting apparatus including a plurality of illumination optical units and a plurality of detection optical units without removal of the substrate from the semiconductor fabrication line while continuing fabrication of the semiconductor devices and while utilizing a foreign particle detector having a pitch variable spatial filter to cut a light reflected from a pattern formed on the substrate, wherein a light cutting portion of the pitch variable spatial filter is pitch variable according to the pattern;

sending a detected signal from the detecting apparatus to a foreign particle detecting processing apparatus which is separate from the detecting apparatus;

processing the detected signal sent from the detecting apparatus by the foreign particle detecting processing apparatus;

counting an amount of foreign particle defects detected at the detecting step and processed at the processing of the detected signal step; and controlling an operation of the semiconductor fabrication line in accordance with the data of foreign particle defects detected.

7. A processing method according to claim 6, wherein data of the amount of foreign particle defects of the substrate counted in the counting step is stored in a memory.

8. A processing method for semiconductor devices in a semiconductor fabrication line, comprising:

processing a substrate in a processing apparatus which is a component of the semiconductor fabrication line;

detecting foreign particle defects on the substrate processed in the processing apparatus utilizing a detecting apparatus including a plurality of illumination optical units and a plurality of detection optical units without removal of the substrate from the semiconductor fabrication line while continuing fabrication of the semiconductor devices and while utilizing a foreign particle detector having a pitch variable spatial filter to cut a light reflected from a pattern formed on the substrate, wherein a light cutting portion of the pitch variable spatial filter is pitch variable according to the pattern;

sending a detected signal from the detecting apparatus to a foreign particle detecting processing apparatus which is separate from the detecting apparatus;

processing the detected signal sent from the detecting apparatus by the foreign particle detecting processing apparatus;

obtaining information of distribution of foreign particle defects on the substrate from the processed detected signal obtained at the step of processing of the detected signal and storing the obtained information in a memory;

wherein the step of detecting foreign particle defects is performed in real time.

9. A processing method according to claim 8, further comprising a step of determining a foreign particle generation condition of the processing apparatus using information of detecting.

10. A processing method for semiconductor devices in a semiconductor fabrication line, comprising:

processing a substrate in a processing apparatus which is a component of the semiconductor fabrication line;

detecting foreign particle defects on the substrate processed in the processing apparatus utilizing a detecting apparatus including a plurality of illumination optical units and a plurality of detection optical units without removal of the substrate from the semiconductor fabrication line while continuing fabrication of the semiconductor devices and while utilizing a foreign particle detector having a pitch variable spatial filter to cut a light reflected from a pattern formed on the substrate, wherein a light cutting portion of the pitch variable spatial filter is pitch variable according to the pattern;

sending a detected signal from the detecting apparatus to a foreign particle detecting processing apparatus which is separate from the detecting apparatus;

processing the detected signal sent from the detecting apparatus by the foreign particle detecting processing apparatus; and determining a foreign particle generation condition of the processing apparatus using information obtained at the step of processing the detected signal.

11. A processing method according to claim 10, wherein if the foreign particle generation condition of the processing apparatus is determined to be abnormal in the determining step, information of the abnormality is outputted.

12. A semiconductor processing method, comprising the steps of:
detecting foreign particle defects on a substrate by a foreign particle detection means having a pitch variable spatial filter to cut a light reflected from a pattern formed on the substrate, a cutting portion of the pitch variable spatial filter being pitch variable according to the pattern, and the foreign particle detection means being attached to at least one processing apparatus which is a component of a semiconductor fabricating system;
sending a detected signal from the foreign particle detection means to a foreign particle detecting processing apparatus which is separate from the foreign particle detection means;
determining the foreign particle generating condition of at least one of the at least one processing apparatus.

13. A semiconductor processing method according to claim 12, wherein the foreign particle on the substrate is detected during a transfer of the substrate by a transfer unit.

14. A semiconductor processing method according to claim 12, wherein an information of the foreign particle defects is outputted based on detected data of the foreign particle defects on the substrate.

15. A semiconductor processing system, comprising:
at least one processing apparatus to process a substrate, the at least one processing apparatus being a component of the semiconductor processing system;
at least one detecting unit having plural illumination optical units and plural detection optical units, the at least one detecting unit being attached to said at least one processing apparatus and detects foreign particle defects on the substrate with the plural illumination optical units and the plural detection optical units, the at least one detecting unit having a pitch variable spatial filter to cut a light reflected from a pattern formed on the substrate, wherein a light cutting portion of the pitch variable spatial filter is pitch variable according to the pattern;
a foreign particle detecting processing unit which is separate from the at least one detecting unit and receives a detected signal from the at least one detecting unit to process the received detected signal; and
a determining unit to determine a foreign particle generating condition from data of the foreign particle detecting processing unit.

16. A semiconductor processing system according to claim 15, wherein the foreign particle defects on the substrate are detected by the detecting unit attached to said at least one processing apparatus after transferring the substrate by a transfer unit from said at least one processing apparatus.

17. A semiconductor processing system, comprising:
at least one processing apparatus to process a substrate, the at least one processing apparatus being a component of the semiconductor processing system;
a detecting unit which is attached to said at least one processing apparatus and detects foreign particle defects on the substrate with a sensor by cutting a light reflected from a pattern formed on the substrate with a pitch variable spatial filter, wherein a light cutting portion of the pitch variable spatial filter is pitch variable according to the pattern;
a foreign particle detecting processing unit which is separate from the detecting unit and which receives a detected signal from the detecting unit to process the received detected signal; and
a foreign particle control system which receives foreign particle data processed by the foreign particle detecting processing unit.

18. A semiconductor processing system according to claim 17, wherein the foreign particle defects on the substrate are detected by the detecting unit attached to said at least one processing apparatus after transferring of the substrate by a transfer unit from said at least one processing apparatus.

19. A semiconductor processing system according to claim 17, wherein the foreign particle control system outputs information for control of the foreign particles.

20. A semiconductor processing method comprising the steps of:
detecting foreign particle defects on a substrate during processing of the substrate in a semiconductor fabrication line by a foreign particle detecting unit having plural illumination units and plural detection units, the foreign particle detecting unit being attached to one processing apparatus of the semiconductor fabrication line and having a pitch variable spatial filter to cut a light reflected from a pattern formed on the substrate, wherein a light cutting portion of the pitch variable spatial filter is pitch variable according to the pattern;
sending a detected signal from the foreign particle detecting unit to a foreign particle detecting processing unit which is separate from the foreign particle detecting unit; and
determining the foreign particle generation condition of the semiconductor fabrication line in accordance with foreign particle processed data of the foreign particle detecting processing unit.

21. A semiconductor processing method according to claim 20, wherein the semiconductor fabrication line includes a plurality of processing units, each processing unit for performing a single processing of the substrate, the step of detecting being effected by the foreign particle detecting unit attached to the one processing apparatus and after the detection, the substrate is transferred to another processing apparatus which performs a process subsequent to a process of the one processing apparatus.

22. A semiconductor processing method comprising the steps of:
processing a substrate with a first processing apparatus which is a component of a semiconductor fabricating system;
transferring the substrate from the first processing apparatus to a foreign particle detection unit attached to the first processing apparatus;
detecting foreign particle defects on the substrate by the foreign particle detection unit having a pitch variable spatial filter to cut a light reflected from a pattern formed on the substrate, wherein a light cutting portion of the pitch variable spatial filter is pitch variable according to the pattern;
sending a detected signal from the foreign particle detection unit to a foreign particle detection processing which is separate from the foreign particle detection unit; and
transferring the substrate from the foreign particle detection unit to a second processing apparatus which is a component of the semiconductor fabricating system; and processing the substrate with the second processing apparatus.

23. A semiconductor processing method according to claim 22, wherein the foreign particle defects are detected by detecting a predetermined area of the substrate.

24. A semiconductor processing method according to claim 22, wherein the foreign particle defects are detected by a linear image sensor.

25. A semiconductor processing method according to claim 22, wherein the first processing apparatus is an etching apparatus.

26. A processing method for semiconductor devices in a semiconductor fabrication line, comprising:

processing a substrate in a first processing apparatus;

transferring the substrate processed in the first processing apparatus to a detecting apparatus without removal of the substrate from the semiconductor fabrication line while continuing fabrication of the semiconductor devices;

detecting foreign particle defects on the substrate transferred to the detecting apparatus within a processing time in the step of processing utilizing a foreign particle detector having a pitch variable spatial filter to cut a light reflected from a pattern formed on the substrate, wherein a light cutting portion of the pitch variable spatial filter is pitch variable according to the pattern;

sending a detected signal from the detecting apparatus to a foreign particle detecting processing apparatus which is separate from the detecting apparatus;

processing the detected signal sent from the detecting apparatus by the foreign particle detecting processing apparatus;

storing a data of foreign particle defects detected at the detecting step, and processed at the processing of the detected signal step in a memory; and controlling an operation of the semiconductor fabrication line in accordance with the data of foreign particle defects detected.

27. A processing method according to claim 26, wherein in the detecting step, detection is performed in a predetermined area of the substrate.

* * * * *